(12) United States Patent
Suzuki et al.

(10) Patent No.: US 8,535,914 B2
(45) Date of Patent: Sep. 17, 2013

(54) PROBE, PROBE SET AND INFORMATION ACQUISITION METHOD USING THE SAME

(75) Inventors: Tomohiro Suzuki, Sagamihara (JP); Nobuko Yamamoto, Yokohama (JP); Hiroki Sasaki, Tokyo (JP); Kazuhiko Mori, Tokyo (JP)

(73) Assignees: Canon Kabushiki Kaisha, Tokyo (JP); President of National Cancer Center, Tokyo (JP)

( * ) Notice: Subject to any disclaimer, the term of this patent is extended or adjusted under 35 U.S.C. 154(b) by 714 days.

(21) Appl. No.: 11/335,638

(22) Filed: Jan. 20, 2006

(65) Prior Publication Data

US 2007/0264635 A1  Nov. 15, 2007

(30) Foreign Application Priority Data

Jan. 21, 2005  (JP) .................................. 2005-014535

(51) Int. Cl.
  *C12P 19/34*  (2006.01)
  *C07H 21/04*  (2006.01)
(52) U.S. Cl.
  USPC ........................ 435/91.2; 536/24.3; 536/24.33
(58) Field of Classification Search
  USPC .............................. 435/91.2; 536/24.33, 24.3
  See application file for complete search history.

(56) References Cited

U.S. PATENT DOCUMENTS

| | | | |
|---|---|---|---|
| 5,227,470 A | 7/1993 | Kanno et al. | 530/359 |
| 5,374,715 A | 12/1994 | Kanno et al. | 530/402 |
| 5,545,521 A | 8/1996 | Okamoto et al. | 435/5 |
| 5,624,798 A | 4/1997 | Yamamoto et al. | 435/6 |
| 5,670,315 A | 9/1997 | Yamamoto et al. | 435/6 |
| 5,705,346 A | 1/1998 | Okamoto et al. | 435/6 |
| 5,830,643 A | 11/1998 | Yamamoto et al. | 435/6 |
| 5,939,256 A | 8/1999 | Yamamoto et al. | 435/6 |
| 5,939,258 A * | 8/1999 | Croce et al. | 435/6 |
| 6,022,961 A | 2/2000 | Yamamoto et al. | 536/24.3 |
| 6,156,506 A | 12/2000 | Yamamoto et al. | 435/6 |
| 6,297,008 B1 | 10/2001 | Okamoto et al. | 435/6 |
| 6,476,215 B1 * | 11/2002 | Okamoto et al. | 536/25.3 |
| 6,569,671 B1 | 5/2003 | Okamoto et al. | 435/285.1 |
| 6,686,439 B2 | 2/2004 | Kenmoku et al. | 528/272 |
| 6,737,238 B2 | 5/2004 | Suzuki et al. | 435/6 |
| 6,803,444 B2 | 10/2004 | Suzuki et al. | 528/361 |
| 6,861,496 B2 | 3/2005 | Kenmoku et al. | 528/272 |
| 6,933,105 B2 * | 8/2005 | Jin | 435/4 |
| 6,949,339 B1 * | 9/2005 | Macina et al. | 435/6 |
| 6,960,432 B2 | 11/2005 | Okamoto et al. | 435/6 |
| 6,963,397 B2 | 11/2005 | Suzuki et al. | 356/317 |
| 2002/0115072 A1 | 8/2002 | Okamoto et al. | 435/6 |
| 2002/0168648 A1 | 11/2002 | Yamamoto et al. | 435/6 |
| 2003/0134797 A1 * | 7/2003 | Podolsky | 514/12 |
| 2004/0018552 A1 | 1/2004 | Okamoto et al. | 435/6 |
| 2004/0110668 A1 * | 6/2004 | Burgess et al. | 514/12 |
| 2004/0235032 A1 | 11/2004 | Suzuki et al. | 435/6 |
| 2004/0241643 A1 | 12/2004 | Yamamoto et al. | 435/5 |
| 2004/0254737 A1 | 12/2004 | Yamamoto et al. | 702/19 |
| 2005/0037439 A1 * | 2/2005 | Bourner et al. | 435/7.2 |
| 2005/0059069 A1 | 3/2005 | Suzuki et al. | 435/6 |
| 2005/0186595 A1 | 8/2005 | Ishii et al. | 435/6 |
| 2006/0051788 A1 | 3/2006 | Suzuki et al. | 435/6 |
| 2006/0068435 A1 | 3/2006 | Yamamoto et al. | 435/6 |
| 2006/0228711 A1 | 10/2006 | Yamamoto | 435/6 |

FOREIGN PATENT DOCUMENTS

| | | | |
|---|---|---|---|
| JP | 11-187900 | | 7/1999 |
| WO | WO 01/51628 | * | 7/2001 |
| WO | WO 0173027 | * | 10/2001 |
| WO | WO 0173131 | * | 10/2001 |
| WO | WO 0194629 | * | 12/2001 |
| WO | WO 02074156 | * | 9/2002 |
| WO | WO 02085298 | * | 10/2002 |
| WO | WO 03078662 | * | 9/2003 |
| WO | 2005001126 | | 1/2005 |
| WO | WO 200500087 | * | 1/2005 |
| WO | WO 2005054508 | * | 6/2005 |

OTHER PUBLICATIONS

Tomasetto et al., The EMBO J. vol. 9, No. 2, pp. 407-414, May 1999.*
Chan et al., The Journal of Biological Chemistry. vol. 260, No. 5, pp. 2629-2632, 1985.*
Lowe et al., Nucleic Acids Research, vol. 18, No. 7, pp. 1757-1761, 1990.*
Kazuhiko Mori, et al., "Highly specific marker genes for detecting minimal gastric cancer cells in cytology negative peritoneal washings", Biochemical and Biophysical Research Communications, vol. 313, 2004, pp. 931-937.
Kumi Nagao, et al., "Expression of molecular marker genes in various types of normal tissue: Implication for detection of micrometastases", International Journal of Molecular Medicine, vol. 10, 2002, pp. 307-310.

* cited by examiner

*Primary Examiner* — Gary Benzion
*Assistant Examiner* — Cynthia Wilder
(74) *Attorney, Agent, or Firm* — Fitzpatrick, Cella, Harper & Scinto

(57) ABSTRACT

The present invention provides a combination of genes useful for information which can be used for the prediction of postoperative recurrence of gastric cancer and the acquisition of the information, a probe detecting these genes and a primer set for PCR, a method for detecting these genes using the primer and the primer set and a method for obtaining the information which can be used for the prediction of recurrence. Information useful for the prediction of postoperative recurrence can be obtained by determining the presence or absence of gastric cancer cells which show a possibility of postoperative recurrence in a sample such as an peritoneal wash collected from a patient by detecting a particular gene specific to gastric cancer cells or a gene product thereof.

12 Claims, 6 Drawing Sheets

No.113 FABP1

No.114 Maspin

No.114 TFF1

No.118 TFF1

SEQUENCE LISTING

<160> NUMBER OF SEQ ID NOS: 46

<210> SEQ ID NO 1
<211> LENGTH: 54
<212> TYPE: DNA
<213> ORGANISM: Artificial Sequence
<220> FEATURE:
<223> OTHER INFORMATION: probe sequence for TFF1

<400> SEQUENCE: 1
ttcgacgaca ccgttcgtgg ggtcccctgg tgcttctatc ctaataccat    50
cgac                                                     54

<210> SEQ ID NO 2
<211> LENGTH: 60
<212> TYPE: DNA
<213> ORGANISM: Artificial Sequence
<220> FEATURE:
<223> OTHER INFORMATION: probe sequence for TFF2

<400> SEQUENCE: 2
ttgaagtgcc ctggtgcttc ttcccgaact ctgtggaaga ctgccattac    50
taagagaggc                                               60

<210> SEQ ID NO 3
<211> LENGTH: 60
<212> TYPE: DNA
<213> ORGANISM: Artificial Sequence
<220> FEATURE:
<223> OTHER INFORMATION: probe sequence for FABP1

<400> SEQUENCE: 3
cattctgcac gatttccgac accccttga tatccttccc cttctggatg     50
agctcttccg                                               60

<210> SEQ ID NO 4
<211> LENGTH: 53
<212> TYPE: DNA
<213> ORGANISM: Artificial Sequence
<220> FEATURE:
<223> OTHER INFORMATION: probe sequence for CK20

<400> SEQUENCE: 4
gtacgaaacc aacgccccga gggctggtcg cgactacagt gcatattaca    50
gac                                                      53

<210> SEQ ID NO 5
<211> LENGTH: 55
<212> TYPE: DNA
<213> ORGANISM: Artificial Sequence
<220> FEATURE:
<223> OTHER INFORMATION: probe sequence for MUC2

<400> SEQUENCE: 5
cttgaagtcc ccgggcttca ggatgacgtg ctggttgtcg ggccgtttga    50
tgata                                                    55

<210> SEQ ID NO 6
<211> LENGTH: 60
<212> TYPE: DNA
<213> ORGANISM: Artificial Sequence
<220> FEATURE:

<223> OTHER INFORMATION: probe sequence for CEA

<400> SEQUENCE: 6

```
ggttggggtt gctctgatat agcagccctg gtgtagtttc ttcatttcag      50
gaagactgac                                                  60
```

<210> SEQ ID NO 7
<211> LENGTH: 60
<212> TYPE: DNA
<213> ORGANISM: Artificial Sequence
<220> FEATURE:
<223> OTHER INFORMATION: probe sequence for TACSTD1

<400> SEQUENCE: 7

```
gcagggtcta aaagctggtg ttattgctgt tattgtggtt gtggtgatag      50
cagttgttgc                                                  60
```

<210> SEQ ID NO 8
<211> LENGTH: 60
<212> TYPE: DNA
<213> ORGANISM: Artificial Sequence
<220> FEATURE:
<223> OTHER INFORMATION: probe sequence for MASPIN

<400> SEQUENCE: 8

```
gtaatttgta aagttgggtg gataagctat ccctgttgcc ggttcatgga      50
ttacttctct                                                  60
```

<210> SEQ ID NO 9
<211> LENGTH: 60
<212> TYPE: DNA
<213> ORGANISM: Artificial Sequence
<220> FEATURE:
<223> OTHER INFORMATION: probe sequence for PRSS4

<400> SEQUENCE: 9

```
gatgctccgg tgctgaccca ggctgagtgt aaagcctcct accctggaaa      50
gattaccaac                                                  60
```

<210> SEQ ID NO 10
<211> LENGTH: 60
<212> TYPE: DNA
<213> ORGANISM: Artificial Sequence
<220> FEATURE:
<223> OTHER INFORMATION: probe sequence for GW112

<400> SEQUENCE: 10

```
aaccagactt actaaccaat tccaccccccc accaaccccc ttctactgcc     50
tactttaaaa                                                  60
```

<210> SEQ ID NO 11
<211> LENGTH: 60
<212> TYPE: DNA
<213> ORGANISM: Artificial Sequence
<220> FEATURE:
<223> OTHER INFORMATION: probe sequence for ACTB

<400> SEQUENCE: 11

```
cctgtggcat ccacgaaact accttcaact ccatcatgaa gtgtgacgtg      50
gacatccgca                                                  60
```

<210> SEQ ID NO 12

```
<211> LENGTH: 24
<212> TYPE: DNA
<213> ORGANISM: Artificial Sequence
<220> FEATURE:
<223> OTHER INFORMATION: Sequence as PCR primer for a part of TFF1

<400> SEQUENCE: 12
cctttggagc agagaggagg caat                                            24

<210> SEQ ID NO 13
<211> LENGTH: 27
<212> TYPE: DNA
<213> ORGANISM: Artificial Sequence
<220> FEATURE:
<223> OTHER INFORMATION: Sequence as PCR primer for a part of TFF1

<400> SEQUENCE: 13
tcagagcagt caatctgtgt tgtgagc                                         27

<210> SEQ ID NO 14
<211> LENGTH: 24
<212> TYPE: DNA
<213> ORGANISM: Artificial Sequence
<220> FEATURE:
<223> OTHER INFORMATION: Sequence as PCR primer for a part of TFF2

<400> SEQUENCE: 14
ataacaggac gaactgcggc ttcc                                            24

<210> SEQ ID NO 15
<211> LENGTH: 28
<212> TYPE: DNA
<213> ORGANISM: Artificial Sequence
<220> FEATURE:
<223> OTHER INFORMATION: Sequence as PCR primer for a part of TFF2

<400> SEQUENCE: 15
agctgataag gcgaagtttc tttcttgg                                        28

<210> SEQ ID NO 16
<211> LENGTH: 20
<212> TYPE: DNA
<213> ORGANISM: Artificial Sequence
<220> FEATURE:
<223> OTHER INFORMATION: Sequence as PCR primer for a part of FABP1

<400> SEQUENCE: 16
tcatgaaggc aatcggtctg                                                 20

<210> SEQ ID NO 17
<211> LENGTH: 21
<212> TYPE: DNA
<213> ORGANISM: Artificial Sequence
<220> FEATURE:
<223> OTHER INFORMATION: Sequence as PCR primer for a part of FABP1

<400> SEQUENCE: 17
caatgtcacc caatgtcatg g                                               21

<210> SEQ ID NO 18
<211> LENGTH: 25
<212> TYPE: DNA
<213> ORGANISM: Artificial Sequence
<220> FEATURE:
<223> OTHER INFORMATION: Sequence as PCR primer for a part of CK20

<400> SEQUENCE: 18
```

```
acacggtgaa ctatgggagc gatct                                           25

<210> SEQ ID NO 19
<211> LENGTH: 24
<212> TYPE: DNA
<213> ORGANISM: Artificial Sequence
<220> FEATURE:
<223> OTHER INFORMATION: Sequence as PCR primer for a part of CK20

<400> SEQUENCE: 19
cttccagaag gcggcggtaa gtag                                            24

<210> SEQ ID NO 20
<211> LENGTH: 22
<212> TYPE: DNA
<213> ORGANISM: Artificial Sequence
<220> FEATURE:
<223> OTHER INFORMATION: Sequence as PCR primer for a part of CEA

<400> SEQUENCE: 20
aacttctcct ggtctctcag ct                                              22

<210> SEQ ID NO 21
<211> LENGTH: 21
<212> TYPE: DNA
<213> ORGANISM: Artificial Sequence
<220> FEATURE:
<223> OTHER INFORMATION: Sequence as PCR primer for a part of CEA

<400> SEQUENCE: 21
gcaaatgctt taaggaagaa g                                               21

<210> SEQ ID NO 22
<211> LENGTH: 20
<212> TYPE: DNA
<213> ORGANISM: Artificial Sequence
<220> FEATURE:
<223> OTHER INFORMATION: Sequence as PCR primer for a part of TACSTD1

<400> SEQUENCE: 22
tgctggggtc agaagaacag                                                 20

<210> SEQ ID NO 23
<211> LENGTH: 21
<212> TYPE: DNA
<213> ORGANISM: Artificial Sequence
<220> FEATURE:
<223> OTHER INFORMATION: Sequence as PCR primer for a part of TACSTD1

<400> SEQUENCE: 23
ttgagttccc tatgcatctc a                                               21

<210> SEQ ID NO 24
<211> LENGTH: 26
<212> TYPE: DNA
<213> ORGANISM: Artificial Sequence
<220> FEATURE:
<223> OTHER INFORMATION: Sequence as PCR primer for a part of GW112

<400> SEQUENCE: 24
cagaagcccc agtaagctgt ttagga                                          26

<210> SEQ ID NO 25
<211> LENGTH: 26
<212> TYPE: DNA
<213> ORGANISM: Artificial Sequence
<220> FEATURE:
```

```
<223> OTHER INFORMATION: Sequence as PCR primer a part of GW112

<400> SEQUENCE: 25
gcactttgtc actgccatca gatttt                                    26

<210> SEQ ID NO 26
<211> LENGTH: 20
<212> TYPE: DNA
<213> ORGANISM: Artificial Sequence
<220> FEATURE:
<223> OTHER INFORMATION: Sequence as PCR primer for a part of MUC2

<400> SEQUENCE: 26
ccggggagtg ctgtaagaag                                           20

<210> SEQ ID NO 27
<211> LENGTH: 20
<212> TYPE: DNA
<213> ORGANISM: Artificial Sequence
<220> FEATURE:
<223> OTHER INFORMATION: Sequence as PCR primer for a part of MUC2

<400> SEQUENCE: 27
gctctcgatg tgggtgtagg                                           20

<210> SEQ ID NO 28
<211> LENGTH: 20
<212> TYPE: DNA
<213> ORGANISM: Artificial Sequence
<220> FEATURE:
<223> OTHER INFORMATION: Sequence as PCR primer for a part of PRSS4

<400> SEQUENCE: 28
ctgggcacag ttgctgtccc                                           20

<210> SEQ ID NO 29
<211> LENGTH: 20
<212> TYPE: DNA
<213> ORGANISM: Artificial Sequence
<220> FEATURE:
<223> OTHER INFORMATION: Sequence as PCR primer for a part of PRSS4

<400> SEQUENCE: 29
ggccaccaga gtcacgctgg                                           20

<210> SEQ ID NO 30
<211> LENGTH: 20
<212> TYPE: DNA
<213> ORGANISM: Artificial Sequence
<220> FEATURE:
<223> OTHER INFORMATION: Sequence as PCR primer for a part of ACTB

<400> SEQUENCE: 30
tcatcaccat tggcaatgag                                           20

<210> SEQ ID NO 31
<211> LENGTH: 20
<212> TYPE: DNA
<213> ORGANISM: Artificial Sequence
<220> FEATURE:
<223> OTHER INFORMATION: Sequence as PCR primer for a part of ACTB

<400> SEQUENCE: 31
cactgtgttg gcgtacaggt                                           20

<210> SEQ ID NO 32
```

```
<211> LENGTH: 25
<212> TYPE: DNA
<213> ORGANISM: Artificial Sequence
<220> FEATURE:
<223> OTHER INFORMATION: Sequence as PCR primer for a part of MASPIN

<400> SEQUENCE: 32
tccggggtag ttggcagaaa tacag                                          25

<210> SEQ ID NO 33
<211> LENGTH: 25
<212> TYPE: DNA
<213> ORGANISM: Artificial Sequence
<220> FEATURE:
<223> OTHER INFORMATION: Sequence as PCR primer for a part of MASPIN

<400> SEQUENCE: 33
tgcatgtcaa ggaagagatg ggaga                                          25

<210> SEQ ID NO 34
<211> LENGTH: 54
<212> TYPE: DNA
<213> ORGANISM: Artificial Sequence
<220> FEATURE:
<223> OTHER INFORMATION: probe sequence for CEA

<400> SEQUENCE: 34
actgtcggca tcatgattgg agtgctggtt ggggttgctc tgatatagca               50
gccc                                                                 54

<210> SEQ ID NO 35
<211> LENGTH: 60
<212> TYPE: DNA
<213> ORGANISM: Artificial Sequence
<220> FEATURE:
<223> OTHER INFORMATION: probe sequence for CEA

<400> SEQUENCE: 35
catcatgatt ggagtgctgg ttggggttgc tctgatatag cagccctggt               50
gtagtttctt                                                           60

<210> SEQ ID NO 36
<211> LENGTH: 60
<212> TYPE: DNA
<213> ORGANISM: Artificial Sequence
<220> FEATURE:
<223> OTHER INFORMATION: Probe Sequence for CEA

<400> SEQUENCE: 36
gatatagcag ccctggtgta gtttcttcat ttcaggaaga ctgacagttg               50
ttttgcttct                                                           60

<210> SEQ ID NO 37
<211> LENGTH: 54
<212> TYPE: DNA
<213> ORGANISM: Artificial Sequence
<220> FEATURE:
<223> OTHER INFORMATION: Probe Sequence for CEA

<400> SEQUENCE: 37
tgctatatca gagcaacccc aaccagcact ccaatcatga tgccgacagt               50
ggcc                                                                 54

<210> SEQ ID NO 38
```

<211> LENGTH: 60
<212> TYPE: DNA
<213> ORGANISM: Artificial Sequence
<220> FEATURE:
<223> OTHER INFORMATION: Probe Sequence for CK20

<400> SEQUENCE: 38

```
gaactgaggt tcaactaacg gagctgagac gcacctccca gagccttgag          50
atagaactcc                                                      60
```

<210> SEQ ID NO 39
<211> LENGTH: 60
<212> TYPE: DNA
<213> ORGANISM: Artificial Sequence
<220> FEATURE:
<223> OTHER INFORMATION: Probe Sequence for CK20

<400> SEQUENCE: 39

```
tctggaggcc caactgatgc agattcggag taacatggaa cgccagaaca          50
acgaatacca                                                      60
```

<210> SEQ ID NO 40
<211> LENGTH: 52
<212> TYPE: DNA
<213> ORGANISM: Artificial Sequence
<220> FEATURE:
<223> OTHER INFORMATION: Probe Sequence for MUC2

<400> SEQUENCE: 40

```
cggaggtttc gtacgccggc tgcaccaaga ccgtcctcat gaatcattgc          50
tc                                                              52
```

<210> SEQ ID NO 41
<211> LENGTH: 60
<212> TYPE: DNA
<213> ORGANISM: Artificial Sequence
<220> FEATURE:
<223> OTHER INFORMATION: Probe Sequence for Maspin

<400> SEQUENCE: 41

```
tcacgttacc ttgacacata gttttttcagt ctatgggttt agttacttta        50
gatggcaagc                                                     60
```

<210> SEQ ID NO 42
<211> LENGTH: 60
<212> TYPE: DNA
<213> ORGANISM: Artificial Sequence
<220> FEATURE:
<223> OTHER INFORMATION: Probe Sequence for Maspin

<400> SEQUENCE: 42

```
tctagctgac tcgcacaggg attctcacaa tagccgatat cagaatttgt          50
gttgaaggaa                                                      60
```

<210> SEQ ID NO 43
<211> LENGTH: 60
<212> TYPE: DNA
<213> ORGANISM: Artificial Sequence
<220> FEATURE:
<223> OTHER INFORMATION: Probe Sequence for Maspin

<400> SEQUENCE: 43

```
aacacttcgt tcgcagagct tttcagattg tggaatgttg gataaggaat          50
```

```
<210> SEQ ID NO 44
<211> LENGTH: 25
<212> TYPE: DNA
<213> ORGANISM: Artificial Sequence
<220> FEATURE:
<223> OTHER INFORMATION: Sequence as PCR primer for a part of CEA

<400> SEQUENCE: 44
tgcatctgga acttctcctg gtctc                                          25

<210> SEQ ID NO 45
<211> LENGTH: 24
<212> TYPE: DNA
<213> ORGANISM: Artificial Sequence
<220> FEATURE:
<223> OTHER INFORMATION: Sequence as PCR primer for a part of CEA

<400> SEQUENCE: 45
tcacgatgtt ggctaggatg gtct                                           24

<210> SEQ ID NO 46
<211> LENGTH: 20
<212> TYPE: DNA
<213> ORGANISM: Artificial Sequence
<220> FEATURE:
<223> OTHER INFORMATION: Sequence as PCR primer for a part of MUC2

<400> SEQUENCE: 46
ctcctctttg cagcaggagc                                                20
```

PROBE, PROBE SET AND INFORMATION ACQUISITION METHOD USING THE SAME

BACKGROUND OF THE INVENTION

1. Field of the Invention

The present invention relates to a method of analyzing and measuring mRNA of genes which specifically express in gastric cancer cells among red blood cells, lymphoid cells, detached intraperitoneal mesothelial cells and a very small amount of free gastric cancer cells contained in a sample obtained from peritoneal wash and the like specimen from a patient before or immediately after procedures such as removal of gastric cancer. Specifically, the present invention relates to an oligonucleotide probe for detection, a probe set and a support carrying the probe. The present invention also relates to a primer and a primer set for amplifying the genes as well as a method of detecting of a gene using the same. Further, the present invention relates to a method of acquiring information to predict postoperative recurrence of gastric cancer with high sensitivity and high accuracy by measuring the gene expression level peculiar to cancer cells.

2. Related Background Art

In the therapy of cancer, recurrence after surgical or endoscopic resection of primary tumor or radiation therapy, chemotherapy and chemoradiotherapy is an important matter of life-and-death matter for a patient. The death by metastasis/recurrence is overwhelmingly more frequent than the death resulted from primary tumor in the death by carcinoma as a main cause. Accordingly, prediction of recurrence to a patient with cancer from whom the primary tumor has been removed particularly by surgical resection will be not only an important pointer in designing the future of the patient with cancer but also critically important for deciding a treatment plan such as postoperative chemotherapy.

It is usually desired in a patient after resection of gastric cancer to monitor the recurrence for a long term by periodic medical examination mainly by postoperative diagnostic imaging. However, when there is no abnormality in one year or more, the long-term monitoring is not always achieved, and there are many cases in which recurrence suddenly occurs afterwards. In the meantime, observation of cells which can be sampled in abdominal operation before resection, that is check of cancer cells by cytological diagnosis by a pathologist, is also performed. This is, for example, a diagnosis method taken at the time of an operation of gastric cancer (perioperative quick cytological diagnosis). When the existence of free cancer cell is recognized, even though in a small number, in physiologically existing intraperitoneal free cells (mainly, red blood cells, lymphoid cells, detached intraperitoneal mesothelial cells), progression of cancer generally advances, and metastasis and recurrence occur at a high probability. The cytological diagnosis is positioned as an extremely important testing method for cancer not only for inferring the prognosis of a patient but also selecting intraoperative and/or postoperative auxiliary chemotherapies (administration of an anticancer drug, hyperthermia treatment, etc.) from the results thereof.

As commonly performed cytological diagnosis methods, there is a method in which cells applied on a glass slide from peritoneal wash are subjected to Papanicolou staining and the shape thereof is observed (simple cytological diagnosis) and a method in which proteins referred to as tumor markers such as CEA (carcinoembryonic antigen) are subjected to immunostaining (immunological cytological diagnosis). The latter, immunological cytological diagnosis, is slow in spreading because it incurs labor and cost. On the other hand, the former, simple cytological diagnosis, is normally performed in Japan on the occasion of a gastric cancer operation. However, identification of an extremely small amount of cancer cells as few as around 1 to 5 per one piece of glass slide by observation with a microscope is practically almost impossible, and the diagnosis by the shape largely depends on the subjectivity of a pathologist and needs considerable skill in the diagnosis. Besides, pathologists performing the diagnosis are chronically short in number, and the specialized domain is subdivided. Therefore, it is practically difficult to allocate the pathologists who can perform the cytological diagnosis at the same level in the majority of hospitals, and a more objective evaluation method is demanded.

Techniques aiming at discerning various cancer markers at a gene expression level as diagnosis technology to meet with such needs have been suggested. This is, for example, determination by real time polymerase chain reaction of mRNA of CEA which serves as a marker in immunostaining. However, when expression of a single gene is utilized as information, there is variation in the expression level for each case, and it has been pointed out that expression may occur in the background, i.e., in cells other than cancer cells (red blood cells, lymphoid cells, detached intraperitoneal mesothelial cells), and pseudo-positive and pseudo-negative are involved (Nagao K, Hisatomi H, Hirata H, et al. Expression of molecular marker genes in various types of normal tissue: Implication for detection of micrometastases. Int J Mol Med 2, 2002, 10: 307-310). Although this method enables to obtain better results in prognostication of gastric cancer as compared with the above-mentioned cytological diagnosis, diagnosis only with CEA has not been spread.

In addition, it has been reported by K. Mori et al./Biochemical and Biophysical Research Communications 313 (2004) 931-937, that a plurality of genes other than CEA are useful for the prediction of recurrence of gastric cancer.

SUMMARY OF THE INVENTION

Recently, it has been reported that a plurality of genes other than CEA are useful for the prediction of recurrence of gastric cancer by an article (Non-Patent Document 2) of the present inventors. The genes have been narrowed down to ten genes which are recognized to strongly express in gastric cancer cells from the comparison of gene expression profile by microarray. It has been confirmed qualitatively by conventional RT-PCR that six of these genes are recognized to express specifically in cancer cells, and the remaining four genes are recognized to strongly express in gastric cancer cells although they slightly express also in the cells other than cancer cells (red blood cells, lymphoid cells, detached intraperitoneal mesothelial cells). If not a qualitative judgment by RT-PCR but a high sensitive quantification method for mRNAs of these eleven kinds of marker genes including β-actin (ACTB) can be developed, accuracy of various diagnostic procedures can be further improved. The problems to be solved by the present invention are summarized below.

1. In the article of Non-Patent Document 1, the above-mentioned five kinds of genes are separately subjected to RT-PCR and after electrophoresis, presence or absence of PCR product is qualitatively judged by ethidium bromide staining respectively. Data tend to vary in such qualitative PCR separately performed for each gene, and it is practically difficult to obtain a constant sensitivity.

2. Conventional RT-PCR lacks in sensitivity for detecting mRNA expressing in a very small amount of cancer cells. If it is attempted to make up for sensitivity by high cycle PCR of 40 to 50 cycles, noise by generation of inadequate PCR products increases and makes judgment impossible. PCR inherently gives right information only in linear amplification cycles.

3. In the article of Non-Patent Document 2, gastric cancer cells were not confirmed in the peritoneal wash of patients positive in qualitative RT-PCR, and therefore, it was not definite whether the results of PCR was really reflected the existence of free gastric cancer cells or not. In other words, data supporting the prediction of recurrence by RT-PCR are not present.

An object of the present invention is to provide a combination of genes useful for information which can be used for the prediction of postoperative recurrence of gastric cancer and the acquisition of the information, a probe detecting these genes and a primer set for PCR, a method for detecting these genes and a method for obtaining the information which can be used for the prediction of recurrence.

Another object of the present invention is to provide a kit to detect and diagnose gastric cancer simply and accurately.

In addition, another object of the present invention is to provide a gene detection kit which enables to detect the existence of a specific gene in the sample highly accurately.

Another object of the present invention is to provide a method for accurately predicting the recurrence risk of gastric cancer.

Still another object of the present invention is to provide a gene detection probe which can be used for specifically detecting a specific gene.

The probe of the present invention for detecting TFF1, TFF2, FABP1, CK20, MUC2, CEA, TACSTD1, MASPIN, PRSS4, GW112 or ACTB which is a gene specific to gastric cancer cells is a probe which is an oligonucleotide comprising one nucleotide sequence selected from the group consisting of the following nucleotide sequences SEQ ID NO. 1-SEQ ID NO. 11, SEQ ID NO. 34-SEQ ID NO. 43:

```
SEQ ID NO: 1:
TTCGACGACACCGTTCGTGGGGTCCCCTGGTGCTTCTATCCTAATACCAT
CGAC (for TFF1)

(SEQ ID NO: 2:
TTGAAGTGCCCTGGTGCTTCTTCCCGAACTCTGTGGAAGACTGCCATTAC
TAAGAGAGGC (for TFF2)

SEQ ID NO: 3:
CATTCTGCACGATTTCCGACACCCCCTTGATATCCTTCCCCTTCTGGATG
AGCTCTTCCG (for FABP1)

SEQ ID NO: 4:
GTACGAAACCAACGCCCCGAGGGCTGGTCGCGACTACAGTGCATATTACA
GAC (for CK20)

SEQ ID NO: 5:
CTTGAAGTCCCCGGGCTTCAGGATGACGTGCTGGTTGTCGGGCCGTTTGA
TGATA (for MUC2)

SEQ ID NO: 6:
GGTTGGGGTTGCTCTGATATAGCAGCCCTGGTGTAGTTTCTTCATTTCAG
GAAGACTGAC (for CEA)

SEQ ID NO: 7:
GCAGGGTCTAAAAGCTGGTGTTATTGCTGTTATTGTGGTTGTGGTGATAG
CAGTTGTTGC (for TACSTD1)

SEQ ID NO: 8:
GTAATTTGTAAAGTTGGGTGGATAAGCTATCCCTGTTGCCGGTTCATGGA
TTACTTCTCT (for MASPIN)

SEQ ID NO: 9:
GATGCTCCGGTGCTGACCCAGGCTGAGTGTAAAGCCTCCTACCCTGGAAA
GATTACCAAC (for PRSS4)
```

```
SEQ ID NO: 10:
AACCAGACTTACTAACCAATTCCACCCCCCACCAACCCCCTTCTACTGCC
TACTTTAAAA (for GW112)

SEQ ID NO: 11:
CCTGTGGCATCCACGAAACTACCTTCAACTCCATCATGAAGTGTGACGTG
GACATCCGCA (for ACTB)

SEQ ID NO: 34:
ACTGTCGGCATCATGATTGGAGTGCTGGTTGGGGTTGCTCTGATATAGCA
GCCC (for CEA)

SEQ ID NO: 35:
CATCATGATTGGAGTGCTGGTTGGGGTTGCTCTGATATAGCAGCCCTGGT
GTAGTTTCTT (for CEA)

SEQ ID NO: 36:
GATATAGCAGCCCTGGTGTAGTTTCTTCATTTCAGGAAGACTGACAGTTG
TTTTGCTTCT (for CEA)

SEQ ID NO: 37:
TGCTATATCAGAGCAACCCCAACCAGCACTCCAATCATGATGCCGACAGT
GGCC (for CEA)

SEQ ID NO: 38:
GAACTGAGGTTCAACTAACGGAGCTGAGACGCACCTCCCAGAGCCTTGAG
ATAGAACTCC (for CK20)

SEQ ID NO: 39:
TCTGGAGGCCCAACTGATGCAGATTCGGAGTAACATGGAAGGCCAGAACA
ACGAATACCA (for CK20)

SEQ ID NO: 40:
CGGAGGTTTCGTACGCCGGCTGCACCAAGACCGTCCTCATGAATCATTGC
TC (for MUC2)

SEQ ID NO: 41:
TCACGTTACCTTGACACATAGTTTTTCAGTCTATGGGTTTAGTTACTTTA
GATGGCAAGC (for MASPIN)

SEQ ID NO: 42:
TCTAGCTGACTCGCACAGGGATTCTCACAATAGCCGATATCAGAATTTGT
GTTGAAGGAA (for MASPIN)
and SEQ ID NO: 43:
AACACTTCGTTCGCAGAGCTTTTCAGATTGTGGAATGTTGGATAAGGAAT
TATAGACCTC (for MASPIN);
``` complementary sequences thereof; and these nucleotide sequences having one or several nucleotides deleted, substituted or added so as to maintain the probe function.

The probe set of the present invention is a probe set comprising two or more probes for detecting two or more of TFF1, TFF2, FABP1, CK20, MUC2, CEA, TACSTD1, MASPIN, PRSS4, GW112 and ACTB which are genes specific to gastric cancer cells, wherein each of the probes is an oligonucleotide comprising one nucleotide sequence selected from the group consisting of the following nucleotide sequences SEQ ID NO. 1-SEQ ID NO. 11, SEQ ID NO. 34-SEQ ID NO. 43:

```
SEQ ID NO: 1:
TTCGACGACACCGTTCGTGGGGTCCCCTGGTGCTTCTATCCTAATACCAT
CGAC (for TFF1)

SEQ ID NO: 2:
TTGAAGTGCCCTGGTGCTTCTTCCCGAACTCTGTGGAAGACTGCCATTAC
TAAGAGAGGC (for TFF2)

SEQ ID NO: 3:
CATTCTGCACGATTTCCGACACCCCCTTGATATCCTTCCCCTTCTGGATG
AGCTCTTCCG (for FABP1)

SEQ ID NO: 4:
GTACGAAACCAACGCCCCGAGGGCTGGTCGCGACTACAGTGCATATTACA
GAC (for CK20)
```

-continued

SEQ ID NO: 5:
CTTGAAGTCCCCGGGCTTCAGGATGACGTGCTGGTTGTCGGGCCGTTTGA
TGATA (for MUC2)

SEQ ID NO: 6:
GGTTGGGGTTGCTCTGATATAGCAGCCCTGGTGTAGTTTCTTCATTTCAG
GAAGACTGAC (for CEA)

SEQ ID NO: 7:
GCAGGGTCTAAAAGCTGGTGTTATTGCTGTTATTGTGGTTGTGGTGATAG
CAGTTGTTGC (for TACSTD1)

SEQ ID NO: 8:
GTAATTTGTAAAGTTGGGTGGATAAGCTATCCCTGTTGCCGGTTCATGGA
TTACTTCTCT (for MASPIN)

SEQ ID NO: 9:
GATGCTCCGGTGCTGACCCAGGCTGAGTGTAAAGCCTCCTACCCTGGAAA
GATTACCAAC (for PRSS4)

SEQ ID NO: 10:
AACCAGACTTACTAACCAATTCCACCCCCCACCAACCCCCTTCTACTGCC
TACTTTAAAA (for GW112)

SEQ ID NO: 11:
CCTGTGGCATCCACGAAACTACCTTCAACTCCATCATGAAGTGTGACGTG
GACATCCGCA (for ACTB)

SEQ ID NO: 34:
ACTGTCGGCATCATGATTGGAGTGCTGGTTGGGGTTGCTCTGATATAGCA
GCCC (for CEA)

SEQ ID NO: 35:
CATCATGATTGGAGTGCTGGTTGGGGTTGCTCTGATATAGCAGCCCTGGT
GTAGTTTCTT (for CEA)

SEQ ID NO: 36:
GATATAGCAGCCCTGGTGTAGTTTCTTCATTTCAGGAAGACTGACAGTTG
TTTTGCTTCT (for CEA)

SEQ ID NO: 37:
TGCTATATCAGAGCAACCCCAACCAGCACTCCAATCATGATGCCGACAGT
GGCC (for CEA)

SEQ ID NO: 38:
GAACTGAGGTTCAACTAACGGAGCTGAGACGCACCTCCCAGAGCCTTGAG
ATAGAACTCC (for CK20)

SEQ ID NO: 39:
TCTGGAGGCCCAACTGATGCAGATTCGGAGTAACATGGAAGGCCAGAACA
ACGAATACCA (for CK20)

SEQ ID NO: 40:
CGGAGGTTTCGTACGCCGGCTGCACCAAGACCGTCCTCATGAATCATTGC
TC (for MUC2)

SEQ ID NO: 41:
TCACGTTACCTTGACACATAGTTTTTCAGTCTATGGGTTTAGTTACTTTA
GATGGCAAGC (for MASPIN)

SEQ ID NO: 42:
TCTAGCTGACTCGCACAGGGATTCTCACAATAGCCGATATCAGAATTTGT
GTTGAAGGAA (for MASPIN)
and SEQ ID NO: 43:
AACACTTCGTTCGCAGAGCTTTTCAGATTGTGGAATGTTGGATAAGGAAT
TATAGACCTC (for MASPIN);

complementary sequences thereof; and these nucleotide sequences having one or several nucleotides deleted, substituted or added so as to maintain the probe function and wherein the above-mentioned two or more probes have different nucleotide sequences.

The probe carrier of the present invention is a probe carrier having a probe for detecting a gene specific to gastric cancer cells immobilized on a carrier, wherein the probe is an oligonucleotide comprising one nucleotide sequence selected from the group consisting of the following nucleotide sequences SEQ ID NO. 1-SEQ ID NO. 11, SEQ ID NO. 34-SEQ ID NO. 43:

SEQ ID NO: 1:
TTCGACGACACCGTTCGTGGGGTCCCCTGGTGCTTCTATCCTAATACCAT
CGAC (for TFF1)

SEQ ID NO: 2:
TTGAAGTGCCCTGGTGCTTCTTCCCGAACTCTGTGGAAGACTGCCATTAC
TAAGAGAGGC (for TFF2)

SEQ ID NO: 3:
CATTCTGCACGATTTCCGACACCCCCTTGATATCCTTCCCCTTCTGGATG
AGCTCTTCCG (for FABP1)

SEQ ID NO: 4:
GTACGAAACCAACGCCCCGAGGGCTGGTCGCGACTACAGTGCATATTACA
GAC (for CK20)

SEQ ID NO: 5:
CTTGAAGTCCCCGGGCTTCAGGATGACGTGCTGGTTGTCGGGCCGTTTGA
TGATA (for MUC2)

SEQ ID NO: 6:
GGTTGGGGTTGCTCTGATATAGCAGCCCTGGTGTAGTTTCTTCATTTCAG
GAAGACTGAC (for CEA)

SEQ ID NO: 7:
GCAGGGTCTAAAAGCTGGTGTTATTGCTGTTATTGTGGTTGTGGTGATAG
CAGTTGTTGC (for TACSTD1)

SEQ ID NO: 8:
GTAATTTGTAAAGTTGGGTGGATAAGCTATCCCTGTTGCCGGTTCATGGA
TTACTTCTCT (for MASPIN)

SEQ ID NO: 9:
GATGCTCCGGTGCTGACCCAGGCTGAGTGTAAAGCCTCCTACCCTGGAAA
GATTACCAAC (for PRSS4)

SEQ ID NO: 10:
AACCAGACTTACTAACCAATTCCACCCCCCACCAACCCCCTTCTACTGCC
TACTTTAAAA (for GW112)

SEQ ID NO: 11:
CCTGTGGCATCCACGAAACTACCTTCAACTCCATCATGAAGTGTGACGTG
GACATCCGCA (for ACTB)

SEQ ID NO: 34:
ACTGTCGGCATCATGATTGGAGTGCTGGTTGGGGTTGCTCTGATATAGCA
GCCC (for CEA)

SEQ ID NO: 35:
CATCATGATTGGAGTGCTGGTTGGGGTTGCTCTGATATAGCAGCCCTGGT
GTAGTTTCTT (for CEA)

SEQ ID NO: 36:
GATATAGCAGCCCTGGTGTAGTTTCTTCATTTCAGGAAGACTGACAGTTG
TTTTGCTTCT (for CEA)

SEQ ID NO: 37:
TGCTATATCAGAGCAACCCCAACCAGCACTCCAATCATGATGCCGACAGT
GGCC (for CEA)

SEQ ID NO: 38:
GAACTGAGGTTCAACTAACGGAGCTGAGACGCACCTCCCAGAGCCTTGAG
ATAGAACTCC (for CK20)

SEQ ID NO: 39:
TCTGGAGGCCCAACTGATGCAGATTCGGAGTAACATGGAAGGCCAGAACA
ACGAATACCA (for CK20)

SEQ ID NO: 40:
CGGAGGTTTCGTACGCCGGCTGCACCAAGACCGTCCTCATGAATCATTGC
TC (for MUC2)

SEQ ID NO: 41:
TCACGTTACCTTGACACATAGTTTTTCAGTCTATGGGTTTAGTTACTTTA
GATGGCAAGC (for MASPIN)

-continued

SEQ ID NO: 42:
TCTAGCTGACTCGCACAGGGATTCTCACAATAGCCGATATCAGAATTTGT
GTTGAAGGAA (for MASPIN)
and SEQ ID NO: 43:
AACACTTCGTTCGCAGAGCTTTTCAGATTGTGGAATGTTGGATAAGGAAT
TATAGACCTC (for MASPIN);

complementary sequences thereof; and these nucleotide sequences having one or several nucleotides deleted, substituted or added so as to maintain the probe function.

The primer set of the present invention is a primer set for amplifying by PCR a partial region of a gene selected from TFF1, TFF2, FABP1, CK20, CEA, TACSTD1, MASPIN, MUC2 and GW112 which are genes specific to gastric cancer cells, the primer set comprising one selected from the following combinations:

SEQ ID NO: 12:    CCTTTGGAGCAGAGAGGAGGCAAT
and
SEQ ID NO: 13:    TCAGAGCAGTCAATCTGTGTTGTGAGC for amplifying a partial sequence of TFF1;

SEQ ID NO: 14:    ATAACAGGACGAACTGCGGCTTCC
and
SEQ ID NO: 15:    AGCTGATAAGGCGAAGTTTCTTTCTTGG for amplifying a partial sequence of TFF2;

SEQ ID NO: 16:    TCATGAAGGCAATCGGTCTG
and
SEQ ID NO: 17:    CAATGTCACCCAATGTCATGG for amplifying a partial sequence of FABP1;

SEQ ID NO: 18:    ACACGGTGAACTATGGGAGCGATCT
and
SEQ ID NO: 19:    CTTCCAGAAGGCGGCGGTAAGTAG for amplifying a partial sequence of CK20;

SEQ ID NO: 20:    AACTTCTCCTGGTCTCTCAGCT
and
SEQ ID NO: 21:    GCAAATGCTTTAAGGAAGAAG for amplifying a partial sequence of CEA;

SEQ ID NO: 44:    TGCATCTGGAACTTCTCCTGGTCTC
and
SEQ ID NO: 45:    TCACGATGTTGGCTAGGATGGTCT for amplifying a partial sequence of CEA;

SEQ ID NO: 22:    TGCTGGGGTCAGAAGAACAG
and
SEQ ID NO: 23:    TTGAGTTCCCTATGCATCTCA for amplifying a partial sequence of TACSTD1;

SEQ ID NO: 32:    TCCGGGGTAGTTGGCAGAAATACAG
and
SEQ ID NO: 33:    TGCATGTGAAGGAAGAGATGGGAGA for amplifying a partial sequence of MASPIN;

SEQ ID NO: 26:    CCGGGGAGTGCTGTAAGAAG
and
SEQ ID NO: 46:    CTCCTCTTTGCAGCAGGAGC for amplifying a partial sequence of MUC2; and SEQ ID NO: 24:    CAGAAGCCCCAGTAAGCTGTTTAGGA
and
SEQ ID NO: 25:    GCACTTTGTCACTGCCATCAGATTTT for amplifying a partial sequence of GW112.

Another embodiment of the primer set of the present invention is a primer set for amplifying by PCR partial regions of at least two genes selected from TFF1, TFF2, FABP1, CK20, MUC2, CEA, TACSTD1, MASPIN, PRSS4, GW112 and ACTB which are genes specific to gastric cancer cells, the primer set comprising two or more of the following combinations:

SEQ ID NO: 12:    CCTTTGGAGCAGAGAGGAGGCAAT
and
SEQ ID NO: 13:    TCAGAGCAGTCAATCTGTGTTGTGAGC for amplifying a partial sequence of TFF1;

SEQ ID NO: 14:    ATAACAGGACGAACTGCGGCTTCC
and
SEQ ID NO: 15:    AGCTGATAAGGCGAAGTTTCTTTCTTGG for amplifying a partial sequence of TFF2;

SEQ ID NO: 16:    TCATGAAGGCAATCGGTCTG
and
SEQ ID NO: 17:    CAATGTCACCCAATGTCATGG for amplifying a partial sequence of FABP1;

SEQ ID NO: 18:    ACACGGTGAACTATGGGAGCGATCT
and
SEQ ID NO: 19:    CTTCCAGAAGGCGGCGGTAAGTAG for amplifying a partial sequence of CK20;

SEQ ID NO: 26:    CCGGGGAGTGCTGTAAGAAG
and
SEQ ID NO: 27:    GCTCTCGATGTGGGTGTAGG for amplifying a partial sequence of MUC2;

SEQ ID NO: 26:    CGGGGGAGTGCTGTAAGAAG
and
SEQ ID NO: 46:    CTCCTGTTTGCAGCAGGAGC for amplifying a partial sequence of MUC2;

SEQ ID NO: 20:   AACTTCTCCTGGTCTCTCAGCT
and

SEQ ID NO: 21:   GCAAATGCTTTAAGGAAGAAG for amplifying a partial sequence of CEA;

SEQ ID NO: 44:   TGCATCTGGAACTTCTCCTGGTCTC
and

SEQ ID NO: 45:   TCACGATGTTGGCTAGGATGGTCT for amplifying a partial sequence of CEA;

SEQ ID NO: 22:   TGCTGGGGTCAGAAGAACAG
and

SEQ ID NO: 23:   TTGAGTTCCCTATGCATCTCA for amplifying a partial sequence of TACSTD1;

SEQ ID NO: 32:   TCCGGGGTAGTTGGCAGAAATACAG
and

SEQ ID NO: 33:   TGCATGTCAAGGAAGAGATGGGAGA for amplifying a partial sequence of MASPIN;

SEQ ID NO: 28:   CTGGGCACAGTTGCTGTCCC
and

SEQ ID NO: 29:   GGCCACCAGAGTCACGCTGG for amplifying a partial sequence of PRSS4;

SEQ ID NO: 24:   CAGAAGCCCCAGTAAGCTGTTTAGGA
and

SEQ ID NO: 25:   GCACTTTGTCACTGCCATCAGATTTT for amplifying a partial sequence of GW112; and SEQ ID NO: 30:   TCATCACCATTGGCAATGAG
and

SEQ ID NO: 31:   CACTGTGTTGGCGTACAGGT for amplifying a partial sequence of ACTB.

The kit for genetic test of the present invention is a kit for genetic test having a probe carrier mentioned above and a primer set mentioned above, wherein the kit for genetic test is to amplify and detect an oligonucleotide comprising a nucleotide sequence specific to at least one selected from TFF1, TFF2, FABP1, CK20, MUC2, CEA, TACSTD1, MASPIN, PRSS4, GW112 and ACTB which are genes specific to gastric cancer cells.

The gene detection method of the present invention is a method for detecting a gene specific to gastric cancer cells, the method comprising contacting a sample containing a nucleic acid with a probe carrier mentioned above and detecting the presence of a gene in the sample which hybridizes to a respective probe immobilized on the probe carrier.

The method of detecting gastric cancer cells of the present invention is a method for detecting the presence or absence of gastric cancer cells in a sample collected from a patient to be examined and the method comprises determination by immunostaining the presence or absence of a gene product in the sample which shows expression of one or more selected from TFF1, TFF2, FABP1, CK20, MUC2, CEA, TACSTD1, MASPIN, PRSS4, GW112 and ACTB which are genes specific to gastric cancer cells.

The method of detecting gastric cancer cells of the present invention is a method for acquiring information for the prediction of recurrence of postoperative gastric cancer, comprising measuring the expression level of one or more selected from TFF1, TFF2, FABP1, CK20, MUC2, CEA, TACSTD1, MASPIN, PRSS4, GW112 and ACTB which are genes specific to gastric cancer cells in a sample collected from a patient to be examined, and comparing the measured expression level and a predetermined standard expression level of the above-mentioned genes which shows a possibility of recurrence of gastric cancer and taking a case where the measured expression level is not less than the standard expression level as information which shows a possibility of recurrence of gastric cancer, the method comprising the steps of: selecting a nucleotide sequence in accordance with a gene in which the expression level is to be measured from the group consisting of the following nucleotide sequences of SEQ ID NO. 1-SEQ ID NO. 11, SEQ ID NO. 34-SEQ ID NO. 43; and acquiring the information which shows a possibility of recurrence of gastric cancer by detecting the gene expression level to be measured using the selected nucleotide sequence and comparing it with the standard expression level, SEQ ID NO: 1:
TTCGACGACACCGTTCGTGGGGTCCCCTGGTGCTTCTATCCTAATACCAT
CGAC (for TFF1)

SEQ ID NO: 2:
TTGAAGTGCCCTGGTGCTTCTTCCCGAACTCTGTGGAAGACTGCCATTAC
TAAGAGAGGC (for TFF2)

SEQ ID NO: 3:
CATTCTGCACGATTTCCGACACCCCCTTGATATCCTTCCCCTTCTGGATG
AGCTCTTCCG (for FABP1)

SEQ ID NO: 4:
GTACGAAACCAACGCCCCGAGGGCTGGTCGCGACTACAGTGCATATTACA
GAC (for CK20)

SEQ ID NO: 5:
CTTGAAGTCCCCGGGCTTCAGGATGACGTGCTGGTTGTCGGGCCGTTTGA
TGATA (for MUC2)

SEQ ID NO: 6:
GGTTGGGGTTGCTCTGATATAGCAGCCCTGGTGTAGTTTCTTCATTTCAG
GAAGACTGAC (for CEA)

SEQ ID NO: 7:
GCAGGGTCTAAAAGCTGGTGTTATTGCTGTTATTGTGGTTGTGGTGATAG
CAGTTGTTGC (for TACSTD1)

SEQ ID NO: 8:
GTAATTTGTAAAGTTGGGTGGATAAGCTATCCCTGTTGCCGGTTCATGGA
TTACTTCTCT (for MASPIN)

SEQ ID NO: 9:
GATGCTCCGGTGCTGACCCAGGCTGAGTGTAAAGCCTCCTACCCTGGAAA
GATTACCAAC (for PRSS4)

SEQ ID NO: 10:
AACCAGACTTACTAACCAATTCCACCCCCCACCAACCCCCTTCTACTGCC
TACTTTAAAA (for GW112)

SEQ ID NO: 11:
CCTGTGGCATCCACGAAACTACCTTCAACTCCATCATGAAGTGTGACGTG
GACATCCGCA (for ACTB)

SEQ ID NO: 34:
ACTGTCGGCATCATGATTGGAGTGCTGGTTGGGGTTGCTCTGATATAGCA
GCCC (for CEA)

-continued

SEQ ID NO: 35:
CATCATGATTGGAGTGCTGGTTGGGGTTGCTCTGATATAGCAGCCCTGGT
GTAGTTTCTT (for CEA)

SEQ ID NO: 36:
GATATAGCAGCCCTGGTGTAGTTTCTTCATTTCAGGAAGACTGACAGTTG
TTTTGCTTCT (for CEA)

SEQ ID NO: 37:
TGCTATATCAGAGCAACCCCAACCAGCACTCCAATCATGATGCCGACAGT
GGCC (for CEA)

SEQ ID NO: 38:
GAACTGAGGTTCAACTAACGGAGCTGAGACGCACCTCCCAGAGCCTTGAG
ATAGAACTCC (for CK20)

SEQ ID NO: 39:
TCTGGAGGCCCAACTGATGCAGATTCGGAGTAACATGGAACGCCAGAACA
ACGAATACCA (for CK20)

SEQ ID NO: 40:
CGGAGGTTTCGTACGCCGGCTGCACCAAGACCGTCCTCATGAATCATTGC
TC (for MUC2)

SEQ ID NO: 41:
TCACGTTACCTTGACACATAGTTTTTCAGTCTATGGGTTTAGTTACTTTA
GATGGCAAGC (for MASPIN)

SEQ ID NO: 42:
TCTAGCTGACTCGCACAGGGATTCTCACAATAGCCGATATCAGAATTTGT
GTTGAAGGAA (for MASPIN)
and SEQ ID NO: 43:
AACACTTCGTTCGCAGAGCTTTTCAGATTGTGGAATGTTGGATAAGGAAT
TATAGACCTC (for MASPIN).

Another embodiment of the method for acquiring information which is useful for predicting recurrence of gastric cancer of the present invention is a method for acquiring information for the prediction of recurrence of postoperative gastric cancer, the method comprising determining by immunostaining the presence or absence of one or more genes selected from TFF1, TFF2, FABP1, CK20, MUC2, CEA, TACSTD1, MASPIN, PRSS4, GW112 and ACTB which are genes specific to gastric cancer cells in a sample collected from a patient with gastric cancer and taking a case where the expression is detected as information which shows a possibility of recurrence of gastric cancer.

The diagnostic kit used for at least one of detection or diagnosis of gastric cancer of the present invention is a diagnostic kit which comprises a combination of at least one probe selected from probes for detecting TFF1, TFF2, FABP1, CK20, MUC2, CEA, TACATD1, MASPIN, PRSS4, GW112 and ACTB which are genes specific to gastric cancer cells and a primer set for amplifying by PCR a partial region of the above-mentioned gene to be detected by the probe, wherein the combination of the probe and the primer is the following combination:

(Combination for TFF1 Detection)
Combination of a probe for detecting TFF1 consisting of a nucleotide sequence represented by SEQ ID NO: 1 of the sequence listing and a primer set for amplifying TFF1 consisting of nucleotide sequences represented by SEQ ID NOS: 12 and 13 of the sequence listing, (Combination for TFF2 Detection)
Combination of a probe for detecting TFF2 consisting of a nucleotide sequence represented by SEQ ID NO: 2 of the sequence listing and a primer set for amplifying TFF2 consisting of nucleotide sequences represented by SEQ ID NOS: 14 and 15 of the sequence listing, (Combination for FABP1 Detection)
Combination of a probe for detecting FABP1 consisting of a nucleotide sequence represented by SEQ ID NO: 3 of the sequence listing and a primer set for amplifying FABP1 consisting of nucleotide sequences represented by SEQ ID NOS: 16 and 17 of the sequence listing, (Combination for CK20 Detection)
Combination of a probe for detecting CK20 consisting of a nucleotide sequence represented by SEQ ID NO: 4, 38 or 39 of the sequence listing and a primer set for amplifying CK20 consisting of nucleotide sequences represented by SEQ ID NOS: 18 and 19 of the sequence listing, (Combination for MUC2 Detection)
Combination of a probe for detecting MUC2 consisting of a nucleotide sequence represented by SEQ ID NO: 5 of the sequence listing and a primer set for amplifying MUC2 consisting of nucleotide sequences represented by SEQ ID NOS: 26 and 27 of the sequence listing, (Combination for MUC2 Detection)
Combination of a probe for detecting MUC2 consisting of a nucleotide sequence represented by SEQ ID NO: 5 or 40 of the sequence listing and a primer set for amplifying MUC2 consisting of nucleotide sequences represented by SEQ ID NOS: 26 and 46 of the sequence listing, (Combination for CEA Detection)
Combination of a probe for detecting CEA consisting of a nucleotide sequence represented by SEQ ID NO: 6 of the sequence listing and a primer set for amplifying CEA consisting of nucleotide sequences represented by SEQ ID NOS: 20 and 21 of the sequence listing, (Combination for CEA Detection)
Combination of a probe for detecting CEA consisting of a nucleotide sequence represented by SEQ ID NO: 6, 34, 35, 36 or 37 of the sequence listing and a primer set for amplifying CEA consisting of nucleotide sequences represented by SEQ ID NOS: 44 and 45 of the sequence listing, (Combination for TACSTD1 Detection)
Combination of a probe for detecting TACSTD1 consisting of a nucleotide sequence represented by SEQ ID NO: 7 of the sequence listing and a primer set for amplifying TACSTD1 consisting of nucleotide sequences represented by SEQ ID NOS: 22 and 23 of the sequence listing, (Combination for Maspin Detection)
Combination of a probe for detecting MASPIN consisting of a nucleotide sequence represented by SEQ ID NO: 8, 41, 42 or 43 of the sequence listing and a primer set for amplifying MASPIN consisting of nucleotide sequences represented by SEQ ID NOS: 32 and 33 of the sequence listing, (Combination for PRSS4 Detection)
Combination of a probe for detecting PRSS4 consisting of a nucleotide sequence represented by SEQ ID NO: 9 of the sequence listing and a primer set for amplifying PRSS4 consisting of nucleotide sequences represented by SEQ ID NOS: 28 and 29 of the sequence listing, (Combination for GW112 Detection)
Combination of a probe for detecting GW112 consisting of a nucleotide sequence represented by SEQ ID NO: 10 of the sequence listing and a primer set for amplifying GW112 consisting of nucleotide sequences represented by SEQ ID NOS: 24 and 25 of the sequence listing, and (Combination for ACTB Detection)
Combination of a probe for detecting ACTB consisting of a nucleotide sequence represented by SEQ ID NO: 11 of the sequence listing and a primer set for amplifying ACTB consisting of nucleotide sequences represented by SEQ ID NOS: 30 and 31.

The gene diagnosis kit of the present invention is a gene diagnosis kit which has at least one probe selected from the above-mentioned probes and a primer set for amplifying by PCR a partial region of a gene to be detected by the probe, wherein the combination of the probe and the primer set is the combination mentioned above.

The method for predicting recurrence risk of a gastric cancer of the present invention is a method for predicting recurrence risk of a gastric cancer, the method comprising the steps of amplifying by PCR genes in an peritoneal wash of a patient with gastric cancer and performing hybridization to an array on which at least one of the probes described in SEQ ID NOS: 1-11 and 34-43 are immobilized, wherein the combination of the probe and the primer set used for PCR is the combination mentioned above.

In addition, the probe provided by the present invention is a probe for genetic test including at least one probe selected from the following (i) to (xi):

(i) at least one probe for detecting TFF1 gene selected from the group consisting of a nucleotide sequence represented by SEQ ID NO: 1, complementary sequence thereof, and these nucleotide sequences having one or several nucleotides deleted, substituted or added so as to maintain the probe function and a nucleotide sequence which hybridizes with a complementary strand of the nucleotide sequence shown in SEQ ID NO: 1 under stringent conditions, (ii) at least one probe for detecting TFF2 gene selected from the group consisting of a nucleotide sequence represented by SEQ ID NO: 2, a complementary sequence thereof and these nucleotide sequences having one or several nucleotides deleted, substituted or added so as to maintain the probe function and a nucleotide sequence which hybridizes with a complementary strand of the nucleotide sequence shown in SEQ ID NO: 2 under stringent conditions, (iii) at least one probe for detecting FABP1 gene selected from the group consisting of a nucleotide sequence represented by SEQ ID NO: 3, a complementary sequence thereof and these nucleotide sequences having one or several nucleotides deleted, substituted or added so as to maintain the probe function and a nucleotide sequence which hybridizes with a complementary strand of the nucleotide sequence shown in SEQ ID NO: 3 under stringent conditions, (iv) at least one probe for detecting CK20 gene selected from the group consisting of a nucleotide sequence represented by SEQ ID NO: 4, 38 or 39, a complementary sequence thereof and these nucleotide sequences having one or several nucleotides deleted, substituted or added so as to maintain the probe function and a nucleotide sequence which hybridizes with a complementary strand of the nucleotide sequence shown in SEQ ID NO: 4, 38 or 39 under stringent conditions, (v) at least one probe for detecting MUC2 gene selected from the group consisting of a nucleotide sequence represented by SEQ ID NO: 5 or 40, a complementary sequence thereof and these nucleotide sequences having one or several nucleotides deleted, substituted or added so as to maintain the probe function and a nucleotide sequence which hybridizes with a complementary strand of the nucleotide sequence shown in SEQ ID NO: 5 or 40 under stringent conditions, (vi) at least one probe for detecting CEA gene selected from the group consisting of a nucleotide sequence represented by SEQ ID NO: 6, 34, 35, 36 or 37, a complementary sequence thereof and these nucleotide sequences having one or several nucleotides deleted, substituted or added so as to maintain the probe function and a nucleotide sequence which hybridizes with a complementary strand of the nucleotide sequence shown in SEQ ID NO: 6, 34, 35, 36 or 37 under stringent conditions, (vii) at least one probe for detecting TACSTD1 gene selected from the group consisting of a nucleotide sequence represented by SEQ ID NO: 7, a complementary sequence thereof and these nucleotide sequences having one or several nucleotides deleted, substituted or added so as to maintain the probe function and a nucleotide sequence which hybridizes with a complementary strand of the nucleotide sequence shown in SEQ ID NO: 7 under stringent conditions, (viii) at least one probe for detecting MASPIN gene selected from the group consisting of a nucleotide sequence represented by SEQ ID NO: 8, 41, 42 or 43, a complementary sequence thereof and these nucleotide sequences having one or several nucleotides deleted, substituted or added so as to maintain the probe function and a nucleotide sequence which hybridizes with a complementary strand of the nucleotide sequence shown in SEQ ID NO: 8, 41, 42 or 43 under stringent-conditions, (ix) at least one probe for detecting PRSS4 gene selected from the group consisting of a nucleotide sequence represented by SEQ ID NO: 9, a complementary sequence thereof and these nucleotide sequences having one or several nucleotides deleted, substituted or added so as to maintain the probe function and a nucleotide sequence which hybridizes with a complementary strand of the nucleotide sequence shown in SEQ ID NO: 9 under stringent conditions, (x) at least one probe for detecting GW112 gene selected from the group consisting of a nucleotide sequence represented by SEQ ID NO: 10, a complementary sequence thereof and these nucleotide sequences having one or several nucleotides deleted, substituted or added so as to maintain the probe function and a nucleotide sequence which hybridizes with a complementary strand of the nucleotide sequence shown in SEQ ID NO: 10 under stringent conditions, and (xi) at least one probe for detecting ACTB gene selected from the group consisting of a nucleotide sequence represented by SEQ ID NO: 11, a complementary sequence thereof and these nucleotide sequences having one or several nucleotides deleted, substituted or added so as to maintain the probe function and a nucleotide sequence which hybridizes with a complementary strand of the nucleotide sequence shown in SEQ ID NO: 11 under stringent conditions.

According to the present invention, probes, a probe carrier (oligonucleotide microarray) for detecting 11 genes including housekeeping genes useful for detecting cancer cells have been enabled to provide. In addition, a sample treatment method necessary for using these probes, specifically primers ready for multiplex PCR, suitable primer set, PCR condition, suitable hybridization condition using the carrier have been enabled to provide. Further, a gene detection method by using the probe carrier, primer set provided by the present invention has been enabled to provide. This gene detection method has enabled to judge the presence or absence of a very small amount of gastric cancer cells in peritoneal wash, blood, lympha, lymph gland of a patient with gastric cancer and to predict the recurrence. In addition, it has been shown that immunostaining using an antibody for the gene product assumed as a subject of examination in the present invention can also accurately detect the presence or absence of cancer cells.

The detection method of a very small amount of gastric cancer cells by the present invention has been proved not only to have accuracy equivalent or more than the results of cytological diagnosis by well-trained pathologist in hospitals specialized in carcinoma but also have a power for precisely predicting 30% or more of the patient who suffers a recurrence in the negative cases by cytological diagnosis. These recurrence cases which tend to be overlooked in cytological diagnosis can be said as minute metastasis cases bearing comparatively little amount of cancer among metastasis cases in which only an extremely very small amount of gastric cancer cells is only recognized in the peritoneal at the time of an operation.

Utility of postoperative auxiliary therapy in gastric cancer has not been strictly proved, but there is a possibility that it may be proved in the future that prevention of recurrence by postoperative chemotherapy can be expected in such a minute metastasis group if a system for detecting a trace amount of tumor cells is enabled.

As stated above, the present invention enables uniform and correct prediction of recurrence of gastric cancer in hospitals in which pathologist specialized in gastric cancer cannot be allotted and has high potential to lead to improvement in the treatment outcome of the gastric cancer which is the most prevailing cancer in Japan.

Other features and advantages of the present invention will be apparent from the following description taken in conjunction with the accompanying drawings, in which like reference characters designate the same or similar parts throughout the figures thereof.

DETAILED DESCRIPTION OF THE PREFERRED EMBODIMENTS

Figure 1:
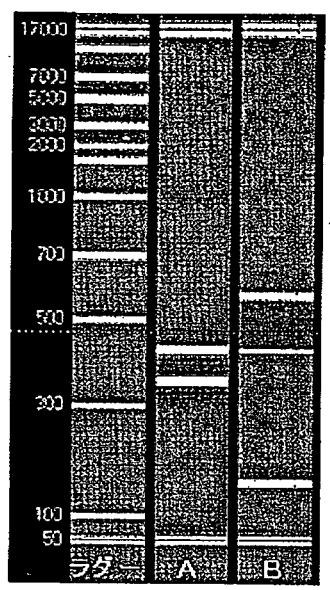
FIG. 1 shows the result of electrophoresis of the PCR products of multiplex PCR.

Preferred embodiments of the present invention will now be described in detail in accordance with the accompanying drawings.

Simultaneous amplification of mRNA transcripted from a plurality of genes and labeling of PCR products by multiplex RT-PCR method have been performed in order to solve the problems 1 and 2 mentioned above. Furthermore, the labeled PCR products were hybridized in an oligonucleotide microarray for quantification and a system for quantifying the expression of a plurality of genes with high sensitivity has been built. The multiplex PCR method is a technique frequently used when a plurality of gene regions are to be amplified at the same time, and known to be effective for polysample SNP analysis. On the other hand, however, it may cause problems that the individually set primers interfere with each other. Therefore, a primer set (combination), sequence designing, PCR condition, etc. which do not cause troubles such as mutual interference when performing amplification at the same time are necessary in the primer set of the present invention which performs multiplex PCR. In addition, as for the genes in the list of an article of Non-Patent Document 2, although specific expression is recognized for five of the genes in gastric cancer cells, the remaining six genes may be also expressed slightly in the cells other than cancer cells (red blood cells, lymphoid cells, detached intraperitoneal mesothelial cells). Therefore, it is preferable that the primers used for multiplex PCR are performed separately for each of these two groups in separate tubes, and that the amplification cycle is optimized.

In the meantime, however, it is also possible to amplify the samples in the same tube for simplicity sake and the like, and in that case, amplification can be performed by setting primers adequately in accordance with the selection of genes to be amplified.

Furthermore, even if multiplex PCR is performed ideally, and the amplification corresponding to expression level is performed, means to detect each of the amplified genes specifically and with a high sensitivity is needed. It is expected that sensitivity is remarkably enhanced and quantifiability is exhibited by hybridizing the fluorescently labeled RT-PCR products on the microarray for detection and measuring fluorescence intensity as compared with a method by electrophoresis/ethidium bromide staining of RT-PCR products. A probe carrier (oligonucleotide microarray) to specifically detect marker genes of the above-mentioned 11 kinds of genes was prepared for predicting existence of free gastric cancer cells from irrigation water of the peritoneal cavity of a patient with gastric cancer and grasping postoperative recurrence risk group precisely. The designing of each gene primer for the above-mentioned multiplex PCR and designing of probes for oligonucleotide microarray are parallelly performed with designing of each primer, and the most optimal PCR primers and probes should be determined in consideration of the results of hybridization. Optimization in the hybridization of PCR products labeled in multiplex RT-PCR and the oligonucleotide microarray is also important.

The mRNA level of each gene in cancer cells varies from sample to sample. Therefore, in order to perform prediction and judgment with high precision, it is essential to establish judgment standard nucleotided on the results of measurement for many samples obtained from facilities which have accepted many patients with gastric cancer and have collected a lot of pathological diagnosis. In other words, establishing an algorithm to judge the presence or absence of free gastric cancer cells from the fluorescence intensity of the amplified genes is necessary.

In order to solve the problem 3 given above, it is necessary to perform not only molecularbiological detection of nucleic acid by microarray as mentioned above but also perform immunostaining in parallel using antibodies for pertinent gene products so as to confirm the presence or absence of free gastric cancer cells in the peritoneal wash.

Specifically, two kinds were excluded from among 11 kinds of genes in the list of an article as Non-Patent Document 2 in preliminary experimental phase of the present invention and TACSTD1 was added as a marker from a newly conducted analysis, thus the object genes were 10 kinds of genes. Furthermore, adding ACTB which was a housekeeping gene, partial sequences having specific sequences to the 11 kinds of genes were picked up and the probe which could detect expression level was designed. The probe sequences designed are probes described in Table 1. In addition, a probe carrier having immobilized probes on the carrier surface was also prepared to perform the detection with high sensitivity using these probes. Because the probes were immobilized in a small area, analytes were accumulated. A highly sensitive and highly accurate detection was enabled because B/F separation was easy.

| Gene name | Sequence (5' → 3') |
|---|---|
| TFF1 | TTCGACGACACCGTTCGTGGGGTCCCCTGGTGCTTCTATCCTAATACCATCGAC (SEQ ID NO: 1) |
| TFF2 | TTGAAGTGCCCTGGTGCTTCTTCCCGAACTCTGTGGAAGACTGCCATTACTAAGAGAGGC (SEQ ID NO: 2) |
| FABP1 | CATTCTGCACGATTTCCGACACCCCCTTGATATCCTTCCCCTTCTGGATGAGCTCTTCCG (SEQ ID NO: 3) |
| CK20 | GTACGAAACCAACGCCCCGAGGGCTGGTCGCGACTACAGTGCATATTACAGAC (SEQ ID NO: 4) |
| CK20 | GAACTGAGGTTCAACTAACGGAGCTGAGACGCACCTCCCAGAGCCTTGAGATAGAACTCC (SEQ ID NO: 38) |
| CK20 | TCTGGAGGCCCAACTGATGCAGATTCGGAGTAACATGGAACGCCAGAACAACGAATACCA (SEQ ID NO: 39) |
| MUC2 | CTTGAAGTCCCCGGGCTTCAGGATGACGTGCTGGTTGTCGGGCCGTTTGATGATA (SEQ ID NO: 5) |
| MUC2 | CGGAGGTTTCGTACGCCGGCTGCACCAAGACCGTCCTCATGAATCATTGCTC (SEQ ID NO: 40) |
| CEA | GGTTGGGGTTGCTCTGATATAGCAGCCCTGGTGTAGTTTCTTCATTTCAGGAAGACTGAC (SEQ ID NO: 6) |
| CEA | ACTGTCGGCATCATGATTGGAGTGCTGGTTGGGGTTGCTCTGATATAGCAGCCC (SEQ ID NO: 34) |
| CEA | CATCATGATTGGAGTGCTGGTTGGGGTTGCTCTGATATAGCAGCCCTGGTGTAGTTTCTT (SEQ ID NO: 35) |
| CEA | GATATAGCAGCCCTGGTGTAGTTTCTTCATTTCAGGAAGACTGACAGTTGTTTTGCTTCT (SEQ ID NO: 36) |
| CEA | TGCTATATCAGAGCAACCCCAACCAGCACTCCAATCATGATGCCGACAGTGGCC (SEQ ID NO: 37) |
| TACSTD1 | GCAGGGTCTAAAAGCTGGTGTTATTGCTGTTATTGTGGTTGTGGTGATAGCAGTTGTTGC (SEQ ID NO: 7) |
| MASPIN | GTAATTTGTAAAGTTGGGTGGATAAGCTATCCCTGTTGCCGGTTCATGGATTACTTCTCT (SEQ ID NO: 8) |
| MASPIN | TCACGTTACCTTGACACATAGTTTTTCAGTCTATGGGTTTAGTTACTTTAGATGGCAAGC (SEQ ID NO: 41) |
| MASPIN | TCTAGCTGACTCGCACAGGGATTCTCACAATAGCCGATATCAGAATTTGTGTTGAAGGAA (SEQ ID NO: 42) |
| MASPIN | AACACTTCGTTCGCAGAGCTTTTCAGATTGTGGAATGTTGGATAAGGAATTATAGACCTC (SEQ ID NO: 43) |
| PRSS4 | GATGCTCCGGTGCTGACCCAGGCTGAGTGTAAAGCCTCCTACCCTGGAAAGATTACCAAC (SEQ ID NO: 9) |
| GW112 | AACCAGACTTACTAACCAATTCCACCCCCCACCAACCCCCTTCTACTGCCTACTTTAAAA (SEQ ID NO: 10) |
| ACTB | CCTGTGGCATCCACGAAACTACCTTCAACTCCATCATGAAGTGTGACGTGGACATCCGCA (SEQ ID NO: 11) |

The sample nucleic acid which is an object to be measured is extremely little in amount and needs labeling with a fluorescent label and the like in some cases, PCR amplification using the sample nucleic acid as a template is necessary, and therefore, primers of that purpose was newly designed in the present invention as well. When genes are individually multiplied, primers in Non-Patent Document 2 specifically act and sufficient amplification can be done, but they are insufficient in the multiplex PCR amplification method of the present invention and therefore, primers functioning in multiplex PCR were newly designed for some genes. The nucleotide sequences of the primers which had been newly designed in the present invention were described in Table 2. In addition, the nucleotide sequences of the primers for all the 11 genes along with the primers described in Non-Patent Document 2 were described in Table 3. The nucleotide lengths of PCR products amplified by the designed primers were also described in Tables 2 and 3.

| Gene name | Forward primer (5' → 3') | Reverse primer (5' → 3') | Nucleotide length (bp) |
|---|---|---|---|
| TFF1 | CCTTTGGAGCAGAGAGGAGGCAAT | TCAGAGCAGTCAATCTGTGTTGTGAGC | 426 |
| TFF2 | ATAACAGGACGAACTGCGGCTTCC | AGCTGATAAGGCGAAGTTTCTTTCTTCGG | 357 |
| FABP1 | TCATGAAGGCAATCGGTCTG | CAATGTCACCCAATGTCATGG | 303 |
| CK20 | ACACGGTGAACTATGGGAGCGATCT | CTTCCAGAAGGCGGCGGTAAGTAG | 975 |
| CEA | AACTTCTCCTGGTCTCTCAGCT | GCAAATGCTTTAAGGAAGAAG | 145 |
| CEA | TGCATCTGGAACTTCTCCTGGTCTC | TCACGATGTTGGCTAGGATGGTCT | 245 |
| MUC2 | CCGGGGAGTGCTGTAAGAAG | CTCCTCTTTGCAGCAGGAGC | 428 |
| TACSTD1 | TGCTGGGGTCAGAAGAACAG | TTGAGTTCCCTATGCATCTCA | 576 |
| MASPIN | TCCGGGGTAGTTGGCAGAAATACAG | TGCATGTCAAGGAAGAGATGGGAGA | 1003 |
| GW112 | CAGAAGCCCCAGTAAGCTGTTTAGGA | GCACTTTGTCACTGCCATCAGATTTT | 950 |

| Gene name | Forward primer (5' → 3') | Reverse primer (5' → 3') | Nucleotide length (bp) |
|---|---|---|---|
| TFF1 | CCTTTGGAGCAGAGAGGAGGCAAT | TCAGAGCAGTCAATCTGTGTTGTGAGC | 426 |
| TFF2 | ATAACAGGACGAACTGCGGCTTCC | AGCTGATAAGGCGAAGTTTCTTTCTTGG | 357 |
| FABP1 | TCATGAAGGCAATCGGTCTG | CAATGTCACCCAATGTCATGG | 303 |
| CK20 | ACACGGTGAACTATGGGAGCGATCT | CTTCCAGAAGGCGGCGGTAAGTAG | 975 |
| MUC2 | CCGGGGAGTGCTGTAAGAAG | GCTCTCGATGTGGGTGTAGG | 506 |
| MUC2 | CCGGGGAGTGCTGTAAGAAG | CTCCTCTTTGCAGCAGGAGC | 428 |
| CEA | AACTTCTCCTGGTCTCTCAGCT | GCAAATGCTTTAAGGAAGAAG | 145 |
| CEA | TGCATCTGGAACTTCTCCTGGTCTC | TCACGATGTTGGCTAGGATGGTCT | 245 |
| TACSTD1 | TGCTGGGGTCAGAAGAACAG | TTGAGTTCCCTATGCATCTCA | 576 |
| MASPIN | TCCGGGGTAGTTGGCAGAAATACAG | TGCATGTCAAGGAAGAGATGGGAGA | 1003 |
| PRSS4 | CTGGGCACAGTTGCTGTCCC | GGCCACCAGAGTCACGCTGG | 574 |
| GW112 | CAGAAGCCCCAGTAAGCTGTTTAGGA | GCACTTTGTCACTGCCATCAGATTTT | 950 |
| ACTB | TCATCACCATTGGCAATGAG | CACTGTGTTGGCGTACAGGT | 155 |

The primer sets described in Table 3 above are designed so that each gene can be surely detected in combination with the probes for detecting each gene described in Table 1. In other words, DNA fragment (PCR product) amplified by each primer set described in Table 3 has a sequence complementary to the probe sequence of the corresponding gene respectively, and can specifically detect each of the genes by hybridization with a probe described in Table 1.

The specific combinations of the primer set and a probe of the present invention include the following.

(i) Combination for TFF1 Detection
Combination of a probe for detecting TFF1 consisting of a nucleotide sequence represented by SEQ ID NO: 1 of the sequence listing and a primer set for amplifying TFF1 consisting of nucleotide sequences represented by SEQ ID NOS: 12 and 13 of the sequence listing;

(ii) Combination for TFF2 Detection
Combination of a probe for detecting TFF2 consisting of a nucleotide sequence represented by SEQ ID NO: 2 of the sequence listing and a primer set for amplifying TFF2 consisting of nucleotide sequences represented by SEQ ID NOS: 14 and 15 of the sequence listing;

(iii) Combination for FABP1 Detection
Combination of a probe for detecting FABP1 consisting of a nucleotide sequence represented by SEQ ID NO: 3 of the sequence listing and a primer set for amplifying FABP1 consisting of nucleotide sequences represented by SEQ ID NOS: 16 and 17 of the sequence listing;

(iv) Combination for CK20 Detection
Combination of a probe for detecting CK20 consisting of a nucleotide sequence represented by SEQ ID NO: 4, 38 or 39 of the sequence listing and a primer set for amplifying CK20 consisting of nucleotide sequences represented by SEQ ID NOS: 18 and 19 of the sequence listing;

(v) Combination for MUC2 Detection
Combination of a probe for detecting MUC2 consisting of a nucleotide sequence represented by SEQ ID NO: 5 of the sequence listing and a primer set for amplifying MUC2 consisting of nucleotide sequences represented by SEQ ID NOS: 26 and 27 of the sequence listing;

(vi) Combination for MUC2 Detection
Combination of a probe for detecting MUC2 consisting of a nucleotide sequence represented by SEQ ID NO: 5 or 40 of the sequence listing and a primer set for amplifying MUC2 consisting of nucleotide sequences represented by SEQ ID NOS: 26 and 46 of the sequence listing;

(vii) Combination for CEA Detection
Combination of a probe for detecting CEA consisting of a nucleotide sequence represented by SEQ ID NO: 6 of the sequence listing and a primer set for amplifying CEA consisting of nucleotide sequences represented by SEQ ID NOS: 20 and 21 of the sequence listing;

(viii) Combination for CEA Detection
Combination of a probe for detecting CEA consisting of a nucleotide sequence represented by SEQ ID NO: 6, 34, 35, 36 or 37 of the sequence listing and a primer set for amplifying CEA consisting of nucleotide sequences represented by SEQ ID NOS: 44 and 45 of the sequence listing;

(ix) Combination for TACSTD1 Detection
Combination of a probe for detecting TACSTD1 consisting of a nucleotide sequence represented by SEQ ID NO: 7 of the sequence listing and a primer set for amplifying TACSTD1 consisting of nucleotide sequences represented by SEQ ID NOS: 22 and 23 of the sequence listing;

(x) Combination for MASPIN Detection
Combination of a probe for detecting MASPIN consisting of a nucleotide sequence represented by SEQ ID NO: 8, 41, 42 or 43 of the sequence listing and a primer set for amplifying MASPIN consisting of nucleotide sequences represented by SEQ ID NOS: 32 and 33 of the sequence listing;

(xi) Combination for PRSS4 Detection
Combination of a probe for detecting PRSS4 consisting of a nucleotide sequence represented by SEQ ID NO: 9 of the sequence listing and a primer set for amplifying PRSS4 consisting of nucleotide sequences represented by SEQ ID NOS: 28 and 29 of the sequence listing;

(xii) Combination for GW112 Detection

Combination of a probe for detecting GW112 consisting of a nucleotide sequence represented by SEQ ID NO: 10 of the sequence listing and a primer set for amplifying GW112 consisting of nucleotide sequences represented by SEQ ID NOS: 24 and 25 of the sequence listing; and (xiii) Combination for ACTB Detection Combination of a probe for detecting ACTB consisting of a nucleotide sequence represented by SEQ ID NO: 11 of the sequence listing and a primer set for amplifying ACTB consisting of nucleotide sequences represented by SEQ ID NOS: 30 and 31.

And at least one combination selected from the group consisting of the above-mentioned (i)-(xiii) may serve as a kit for at least one of detection and diagnosis of gastric cancer. In addition, at least one combination selected from the group consisting of the above-mentioned (i)-(xiii) may serve as a kit for detecting a corresponding gene. In addition, in these kits, probes can be provided as an array arranged on a solid-phase surface.

Furthermore, nucleotided on knowledge of the present inventors that a recurrence risk of a patient with gastric cancer is high when either one of the existence of the 11 kinds of genes described in Table 1 is recognized in peritoneal irrigation solution of the patient with gastric cancer, at least one combination selected from the group consisting of the above-mentioned (i)-(xiii) can be used for the prediction of a recurrence risk of gastric cancer.

Specifically, the method comprises, for example, (i) a step of amplifying by PCR genes in an peritoneal wash of a patient with gastric cancer, (ii) a step of subjecting the amplified product obtained by the above-mentioned step (i) to hybridization reaction with a probe comprising a nucleotide sequence represented by SEQ ID NOS: 1-11 and 34-43 of the sequence listing, and (iii) a step of detecting the presence or absence of the subject gene in the peritoneal wash by detecting a hybrid with the probe from the resultant products of the above-mentioned step (ii), and in addition, the prediction accuracy of the recurrence risk of gastric cancer can be enhanced by setting the combination of a probe and a primer set to at least one combination selected from the group consisting of the above-mentioned (i)-(xiii) in a prediction method of a recurrence risk of gastric cancer wherein the above-mentioned step (i) has a step of performing PCR by using the primer set for amplifying a partial region of a gene which is a detection subject of the probe of the above-mentioned step (ii) by.

In addition, the present inventors have found that when the 11 kinds of the genes in the sample using all of the above-mentioned primer sets, primer sets which can amplify in the same condition can be combined and multiplex PCR can be performed with each primer set and each gene can be more effectively amplified. Examples of the primer set invented by the present invention are shown below.

Group A: TFF1, TFF2, FABP1, CK20, MUC2, CEA
Group B: TACSTD1, MASPIN, PRSS4, GW112, ACTB Further, primer sets TFF1, TFF2, FABP1, CK20, MUC2, CEA, TACSTD1, MASPIN, and ACTB are examples of good primer sets.

The expression level of each gene can be specifically measured by subjecting a DNA amplified by PCR with each of these primer sets and fluorescently labeled to hybridization with a probe carrier developed in the present invention.

For example, in a prediction of a recurrence risk of gastric cancer, assume that the probe to be used by the step (ii) is all of the probes for detecting 11 kinds of genes described in Table 1 and that they are immobilized on a solid phase. If 11 kinds of the above-mentioned genes are present in peritoneal wash in that case, it is preferable that all of these genes are normally amplified in the step (i). Here, amplification of subject genes divided into the groups of primer sets which can be amplified in the same condition in association with a subject gene to be amplified and the corresponding primer sets can enhance the reliability of the results of the subsequent hybridization reaction with the probe. Specifically, for example, peritoneal wash is divided into two groups in the above-mentioned step (i) (first peritoneal wash, second peritoneal wash). As for the first peritoneal wash, genes in the first peritoneal wash are amplified by using primer sets which constitute each of the above-mentioned combinations (i), (ii), (iii), (iv), (v) and (vi). As for the second peritoneal wash, genes in the second peritoneal wash are amplified by using primer sets which constitute each of the above-mentioned combinations (ix) to (xii). Then the mixture of each amplified products are subjected to hybridization reaction with probes on solid phase, for example, probes consisting of the nucleotide sequences represented by SEQ ID NOS: 1-11 or SEQ ID NOS: 34-43 in addition to them. This enables to detect presence or absence of 11 kinds of subject genes to be detected in the peritoneal wash more precisely. That is to say, prediction accuracy of a recurrence risk of gastric cancer can be further enhanced.

In addition, subject genes can be precisely detected without dividing the peritoneal wash into a plurality of groups depending on the kind of the subject genes, and a primer set to be used for PCR in the above-mentioned prediction of recurrence risk of gastric cancer.

For example, the subject genes to be detected are narrowed down to 9 kinds of CEA, TFF1, TFF2, FABP1, CK20, MUC2, MASPIN, ACTB and TACSTD1 and assume that the following probes are used as probes for detecting the genes:

Either one selected from probes for detecting CEA comprising nucleotide sequences represented by SEQ ID NOS: 34 to 37, A probe for detecting TFF1 comprising a nucleotide sequence represented by SEQ ID NO: 1, A probe for detecting TFF2 comprising a nucleotide sequence represented by SEQ ID NO: 2, A probe for detecting FABP1 comprising a nucleotide sequence represented by SEQ ID NO: 3, Either one selected from probes for detecting CK20 comprising a nucleotide sequence represented by SEQ ID NO: 38 or 39, A probe for detecting MUC2 comprising a nucleotide sequence represented by SEQ ID NO: 40, Either one selected from probes for detecting MASPIN comprising nucleotide sequence represented by SEQ ID NOS: 41 to 43, A probe for detecting ACTB comprising a nucleotide sequence represented by SEQ ID NO: 11, A probe for detecting TACSTD1 comprising a nucleotide sequence represented by SEQ ID NO: 7.

And assume that the following primer sets are used as primer sets for amplifying the subject genes:

A primer set for CEA amplification comprising nucleotide sequences represented by SEQ ID NOS: 44 and 45, A primer set for TFF1 detection comprising nucleotide sequences represented by SEQ ID NOS: 12 and 13, A primer set for TFF2 detection comprising nucleotide sequences represented by SEQ ID NOS: 14 and 15, A primer set for FABP1 detection comprising nucleotide sequences represented by SEQ ID NOS: 16 and 17, A primer set for CK20 detection comprising nucleotide sequences represented by SEQ ID NOS: 18 and 19, A primer set for MUC2 detection comprising nucleotide sequences represented by SEQ ID NOS: 26 and 46, A primer set for MASPIN detection comprising nucleotide sequences represented by SEQ ID NOS: 32 and 33, A primer set for ACTB detection comprising nucleotide sequences represented by SEQ ID NOS: 30 and 31, A primer set for TACSTD1 detection comprising nucleotide sequences represented by SEQ ID NOS: 22 and 23.

In this case, amplification of the genes in the peritoneal wash by PCR using each of the above-mentioned primer sets can amplify the subject genes normally by adding all of the 9 kinds of the above-mentioned primer sets to the peritoneal wash and performing PCR in a predetermined condition. Consequently, detection of the subject genes to be detected in the peritoneal wash and, as a result, accuracy of the prediction of a recurrence risk of gastric cancer can be improved.

In addition, it has been confirmed that among the above-mentioned gastric cancer specific genes, immunostaining using an antibody for gene products of MASPIN, CK20, MUC2, TFF1 and FABP1 is extremely effective for identification of presence or absence of free gastric cancer cell in the peritoneal wash. Furthermore, it has turned out that the expression of the marker genes by a probe carrier and the existence of free gastric cancer cells by this immunostaining are in good agreement with each other. What have been normally used for immunostaining till now are only several kinds such as antibody to CEA and therefore, detection of free gastric cancer cells in the peritoneal wash using antibodies to the above-mentioned five kinds of gene products is filed as the present invention.

The present invention is described in more detail hereinafter, but any of the description is an example for preferably carrying out the contents of the present invention and does not limit the other embodiments of the present invention.

The analyte of the present invention, mRNA, is collected from the free cells contained in the peritoneal wash. Usually the peritoneal wash is centrifuged and free cells which are floating components are made to deposit in the shape of pellet and after that total RNA containing mRNA is extracted from the pellet. Various methods are devised as an extracting method of total RNA and provided as a kit by many manufacturers, and any of the kits can be used in the present invention. However, the method for detecting gastric cancer cell specific genes by the present invention is a detection method with an extremely high sensitivity, and the extraction of RNA with purity as high as possible is preferable. Specifically, it is preferable to evade signals derived from non-RNA due to contamination of DNA and the like. As an example of an extraction kit for RNA, ISOGEN marketed by Nippon Gene Co., Ltd. is an extraction kit of extremely high RNA purity. In the extraction of RNA by separation of the organic layer such as ISOGEN and the aqueous layer, attentive collection from the aqueous layer is important, and the handling that made much of extraction accuracy than yield is preferable.

In addition, scrupulous care is necessary for a container used for handling when the amount of the collected RNA is small. For example, when there are minute scratch and the like on the surface of the container, components of RNA are adsorbed to the site and may significantly affect the yield and quality. Usually containers such as one made of polypropylene of around 1 ml are used for the reaction, but it is preferable to take cares such as changing to a new container depending on the circumstances.

The method of checking the collected RNA includes a method of checking by electrophoresis. RNA collected from a human cell and having a good quality free from degradation contains little amount of short nucleic acids lower than 18S, and it is usual that the ratio of 28S to 18S is 1.5 times or more. As for RNA in which fragmentation is predicted including the above, means such as recollection is preferably attempted to a possible extent.

Oligonucleotide probes which specifically detected each of the genes were designed in correspondence to the genes described in Table 1 identified as effective genes for predicting the existence of free gastric cancer cells in the peritoneal wash. As for the designing, they were designed deliberately so that specificity among each of the genes could be maintained and genes described in Table 1 could be detected at the same time. The nucleotide sequences of the designed probes are also shown in Table 1.

The probes described in Table 1 are 50 to 60mer and adjusted so that Tm values and the like are not significantly different among the probes assuming that a plurality of probes are used at the same time for performing hybridization. However, the length of the nucleotide sequence can be changed and used referring to the nucleotide sequence of the subject genes to be detected as long as the specificity is not lost. In addition, double-stranded DNA is labeled and subjected to hybridization in some cases, and the sequence of probe to be used in such a case may be a complementary sequence of the nucleotide sequence shown in Table 1. Further, two or more kinds of the probes selected from these probes can be provided as a probe set. In other words, probes which can detect at least two kinds selected from the genes described in Table 1 as the subject to be detected can constitute the probe set.

Probes for detecting mRNA by the present invention have specificity to each other. In other words, a subject gene to be detected and a probe to detect it correspond strictly in one-on-one and if hybridization of probe can be confirmed, a plurality of probes can be used as a set at the same time. As for the embodiment of the probes, either liquid phase or solid phase can be used, but it is preferable that each of the probes are immobilized on a carrier physically isolated in order to detect hybridization reaction for every probe. In the case of detection using probes immobilized on a minute region of the carrier surface, not only highly sensitive detection is enabled due to the accumulation of the fluorescently labeled cDNA but also highly accurate detection is enabled because B/F separation is easy and it is suitable for using probes effectively.

Any immobilizing method of probes can be applied regardless of binding style including absorption, ionic bond and covalent bond. In order to immobilize probes more strongly, the probes may be chemically modified and bonded using the modified residues to such an extent that hybridization of cDNA amplified from the sample (here, peritoneal wash) mRNA and fluorescently labeled and the probe is not impaired. As the methods often used for chemical modification, a method introducing an amino group to the 5' end, a method introducing a thiol group, and a method modifying with biotin are often used.

As for the carrier, various carriers can be used without restriction regardless of the shape such as planar substrate, beads and fibers. As for materials, metal, glass, plastic, polymer and fiber can be used without particular restriction. Among these, a DNA microarray in which oligonucleotide probes are immobilized on the surface of a glass substrate can be mentioned as a highly sensitive gene detection method which can detect many items at the same time. A DNA microarray is a device for detecting nucleic acids in which a plurality of probes are arranged in a high-density array on the surface of a plane substrate, and it is one of the preferable embodiments used as an embodiment in which probes of the present invention is immobilized on a solid phase carrier to be used as a device for detecting nucleic acids. Various methods normally used for immobilizing probes on the solid-phase carrier can be used. A glass is used as a solid phase and treated with an amino silane coupling agent which can introduce amino groups and maleimide groups are introduced on the surface by EMCS, etc. manufactured by Dojin Chemical Corporation. Furthermore, oligonucleotide probes modified with a thiol group at 5'-end terminal and a maleimide group are allowed to react and the probes can be introduced onto the glass surface entirely by covalent bond. The coupling procedure is described in detail, for example, in Japanese Patent Application Laid-Open No. H11-187900 and can be preferably used in the present invention.

As given in the above-mentioned laid-open publication, when the solid-phase carrier is a planar carrier such as a glass substrate, means for supplying probes on the surface thereof is typically pipetting or pin method and the like. These can be used also in the present invention, but the solution supplying method using an ink-jet method typically represented by bubble jet method or piezomethod can be preferably used in the present invention in order to supply a less amount of probe solution in high density.

A pretreatment method of the sample RNA is performed for two purposes, one for labeling to make the object mRNA in the sample RNA to be spectrophotometrically visualized and another for amplification in order to enhance sensitivity. Labeling is not always needed in the case where there is other means for detecting the hybridization of fluorescent labeled cDNA and a probe after hybridization with a probe has been performed. In addition, amplification is not always necessary when there is a lot of mRNA to be detected in the sample RNA.

The amplification method which is often used when amplification step is needed includes RT-PCR. In the case where multiplex PCR amplifying a plurality of genes at the same time (in reaction of identity liquid) is performed, even when the primers can amplify separately the gene (for example, primers of Publication Information 2), the primers interfere with each other and desired amplification tends not to be possible. New primers which can be used with multiplex PCR reaction have been designed in the present invention in order to solve this problem. The newly-designed primers are shown in Table 2. The nucleotide sequences of 13 kinds of primer sets usable in the present invention are summarized in Table 3 along with the primers designed in Non-Patent Document 2. As for these sequences, the nucleotide sequences are adjusted so that they may keep the uniformity among a plurality of primers similarly as in the nucleotide sequences of probes, addition and deletion of nucleotide sequence are possible without losing specificity as long as it is within the range which does not impair the amplification rate of the PCR reaction.

The labeling step can be easily carried out by using a substrate which has been labeled as an amplified product in the above-mentioned amplification step. In addition to the method of introducing as a substrate, a method of labeling the primer in itself beforehand and a method of binding a label to a specific functional group of in the obtained sample by chemical or enzymatic procedure can be adopted. Because fluorescent substance used as a labeling substance is generally a molecule having a relatively high molecular weight, and when labeling is performed on the substrate of PCR reaction, it may affect amplification efficacy or labeling ratio.

In this regard, when a substrate labeled with, for example, an aminoallyl label or a biotin label, it will affect the PCR reaction comparatively slightly and therefore it is used preferably. Of these, a modified analyte having an aminoallyl can be easily detected by attaching an arbitrary labeling agent (for example, a fluorescent dye) after the PCR reaction ends via the amino group. Cy3 or Cy5 is often used as a labeling agent, and PCR products labeled with Cy3 or Cy5 can be obtained by allowing a Cy3 derivative or a Cy5 derivative having a succinimide group to act on the aminoallyl labeled PCR products.

The primers described in Table 3 can be used for PCR reaction by combining plural kinds thereof and if necessary, suitable primers are combined and can be used for RT-PCR from a sample RNA as a primer set.

Any combination of primers constituting a primer set is possible. Primers performing PCR with the same amplification efficacy are combined or primers evading mutual interference as much as possible are combined in many cases. The constitution of a primer set may be decided in consideration of the expression level of the subject gene to be examined, and if necessary, by judgment standard of interest such as qualitative or quantitative criteria.

For example, as a subject gene to be examined of the present invention, suitable amplification is possible by combining the following genes and subjecting each of them to PCR amplification under a suitable conditions:

As group A: TFF1, TFF2, FABP1, CK20, MUC2, CEA

As group B: TACSTD1, MASPIN, PRSS4, GW112, ACTB

In addition, in consideration of simplicity and the like, amplification reaction can be performed in a single PCR tube. In that case, all of the genes can be amplified at the same time, but, for example, combinations using nine kinds of TFF1, TFF2, FABP1, CK20, MUC2, CEA, TACSTD1, MASPIN, ACTB are one of the good combinations enabling good amplification.

Polymerase enzymes for PCR are supplied by various manufacturers, and any kind of enzyme can be used. For example, AccuPrime of InvitroGen Corporation can be preferably used in the amplification step of the present invention.

In addition, these primer sets and a probe carrier having a constitution in which probes are bound to the carrier can be combined and utilized as a kit for detecting a specific gene. Even only the primer sets can be used as a similar gene detection kit by diluting in a suitable buffer solution.

DNA microarray of which probes hybridize to analytes can be used with a commercially available microarray scanner. Fluorescent intensities corresponding to respective probes can be obtained by scanning. In the case of a DNA microarray, accurate measurement with little fluctuation is enabled by biding a plurality of probes of the same kind to the same probe carrier.

When expression analysis by a DNA microarray is performed, judgment with higher reliability can be achieved by duly standardizing for each probe and analyte RNA and effecting adjustment to enable comparison among the samples. For example, when there is difference in the expression amount of the subject genes or difference in the amplification efficacy of the subject depending on the analyte RNA, the expression amount can be compared with that of a housekeeping gene (for example, ACTB) and the like which is known to express constantly per every cell, which enables correction of the collected amount. Furthermore, in the case where the binding force is different to the subject mRNA to be examined of a constant concentration for each of the probes, quantification by calibration curve is possible. The calibration graph (calibration curve) can be prepared from brightness values for synthetic analyte which is artificially synthesized and has a known concentration and the like, and expression level of the subject gene to be examined contained in the analyte RNA was measured by referring to the value and judgment can be performed in consideration thereof, which enables higher accurate judgment.

After the expression level of each gene is measured by the above-mentioned probe carrier (oligonucleotide microarray), presence or absence of cancer cells and recurrence can be predicted totally judging the obtained brightness values. As a specific judgment method from brightness value, various methods can be used without restriction in particular. The type and number to be incorporated in the judgment are arbitrarily selected and all the genes for which RT-PCR has been performed can be the subject to be measured or one or more genes may be selected and judged.

Because the expression amount of the subject gene to be examined in cancer cells contained in the sample is variable, it is difficult to judge by the expression amount of a single gene. Therefore, it is required to judge totally from the expression amount of a plurality of genes. For example, genes having a high relevance with prognosis can have a large weight while genes having a low relevance with prognosis can have a small weight and a precise judgment can be performed by further taking the summation thereof.

In addition, a method in which a cut-off value of expression amount (expression level) of each gene is predetermined and the number of genes exceeding the cut-off value is counted and the judgment is performed whether it is above or below the predetermined number is effective. On this occasion, setting of the cut-off value and judgment standard can be arbitrarily performed and, for example, there is a method in which the sample in which cancer cells are not present is made a negative control and a certain number of samples are measured to derive the judging value from there. There are a method in which the maximum value and mean value of this negative control are used as a reference and a method in which a numerical value such as variance is added to the reference value and used as a judging value.

In addition, if there is uniformity and stability in the probe carrier, judgment can be performed nucleotided on the absolute brightness. In that case, there is a method in which cases wherein the brightness value exceeds the background by a certain level are counted, etc.

The most important point in establishing the judgment standard is to set an empirical standard by the analysis using real samples in medical institutions. In addition, it is important to get proof of existence of cancer cells by immunostaining method and the like performed on the sample nucleotided on Evidence-nucleotided Medicine demanded in modern medicine. In the present invention, more than 100 cases of true samples (peritoneal wash) of patients with gastric cancer are used to establish the standard, which is described in Examples. In the development of a clinical laboratory kit as in the present invention, it is considered that not an evaluation of a kit by a model experiment but an evaluation with real clinical samples is essential.

In addition, the method of detecting a very small number of gastric cancer cells by the present invention is a detection method extremely highly sensitivity and specific, but it will be a more effective judgment method in combination with clinical findings and the other measured values. It is more effective to totally judge the presence or absence of gastric cancer cells by referring to numerical values such as presence of lymph node metastasis, various carcinoma marker as well as results of cytology usually becoming required in a gastric cancer operation and having a good command of a judgment method in accordance with the situation.

In addition, it is self-evident from Examples that various genes used in the present invention can be used for the detection of gastric cancer cells which got mixed with blood, lympha, lymph gland besides peritoneal wash of a patient with gastric cancer. Because there are many red blood cells, lymphoid cells which serve as the background in blood, lympha, lymph gland contained in the peritoneal wash, and the present method can judge presence of a very small number of gastric cancer cells contained in these cells. Therefore, detection of gastric cancer cells contained in the sample obtained from the peritoneal wash and the like can be achieved by a method using a probe and a primer set of the present invention and a method using immunostaining and the information which is useful for a prediction of postoperative gastric cancer recurrence can be obtained nucleotided on the results. As for the peritoneal wash, blood, lympha, lymph gland, those obtained during operation or sampled before operation can be used. For example, preliminary sampling (biopsy) is possible and specifically an apparatus is inserted into the peritoneal and the sample can be collected by sampling the intraperitoneal liquid.

EXAMPLES

Following is a particular Example and the present invention will be described in detail therewith.

Example 1

Recovery of Total RNA from Cells and Preparation of cDNA (1) Human Gastric Cancer Cell, KATOIII A cell line derived from human gastric cancer, KATOIII (Dainippon Pharmaceuticals Inc.) was cultured to obtain about $1 \times 10^5$ cells. From the cells total RNA was recovered by a conventional method described below. Cells were homogenized in ISOGEN manufactured by Nippon Gene Inc., mixed with a small amount of chloroform and centrifuged at 8,000 rpm for 15 min, and the supernatant was recovered. The supernatant was mixed with an equal volume of isopropanol, incubated at room temperature for 15 min or longer and centrifuged at 15,000 rpm for 15 min, and the total RNA was recovered as a pellet and further precipitated by ethanol (70%).

The reverse transcription reaction was carried out using about 5 µg total RNA, SuperScriptChoice System for cDNA Synthesis manufactured by Invitrogen Corp. and T7-$(dT)_{24}$ primer (Amersham-Pharmacia). In particular the following method was used. The final volume of the mixture was adjusted to 20 µl.

First, total RNA 5 µg was mixed with T7-$(dT)_{24}$ primer and heat denatured. After cooling rapidly, a buffer, DTT, dNTP Mix was added and then SuperScript II RT was added. The reaction solution was incubated at 42° C. for 1 h and rapidly cooled, and 20 µl of the 1st strand solution was recovered. The 1st strand cDNA solution thus obtained was subjected to the 2nd strand cDNA synthesis without purification according to the procedures specified by the kit. That is, after synthesizing the 2nd strand by adding DNA ligase, DNA polymerase and RNase H, the termini were made blunt with T4 DNA polymerase. The cDNA obtained was purified by the conventional method using the phase lock gel manufactured by Eppendorf Co., Ltd. The purified cDNA was dissolved in distilled water at 1 µg/µl.

(2) Cells in Peritoneal Wash During Operation of Gastric Cancer Patients

Gastric cancer patients undergoing the operation were subjected to peritoneal wash according to the standard technique using 100 ml of physiological saline and the peritoneal wash was collected. From the collected peritoneal wash an amount needed for tests in the pathology laboratory was taken and the rest that was the surplus sample, was subjected to the test. Peritoneal free cells were recovered from the peritoneal wash as a pellet of the sediment by centrifuging at 1500 rpm for 10 min at room temperature and removing the supernatant. Recovery of total RNA from the collected cells and cDNA synthesis were carried out in the similar manner to that described in the Example 1 (1) for KATOIII cells.

Further, the recovery of the peritoneal wash from the gastric cancer patients during the operation, and use thereof for research were carried out with the consent of the patients in accordance with the informed consent. The peritoneal washes were collected at the National Cancer Center and 118 cases, for which the prognosis could be determined, were used for the experiments. Conventional cytology was carried out during the operation on the recovered cells, and prognosis after operation of the gastric cancer patients were followed for 2 years or longer and the information such as recurrence or the like were obtained. The clinical data such as 2-year recurrence rate and the like for all the 118 cases are shown in Table 4 below. The results of cytology and immunostaining were obtained from the peritoneal wash of the patients undergoing the operation. As the second antibody in the immunostaining method, SimpleStain MAX-P0 (M) Kit (peroxidase labeled mouse IgG monoclonal antibody derived from goat, as an antibody) was used.

TABLE 4

Clinical data of samples used, etc.

| Sample number | Clinical information, etc. | Cytology | Immunostaining |
|---|---|---|---|
| 1 | Stage 1a | Negative | ND |
| 2 | Stage 1a | Negative | ND |
| 3 | Stage 1a | Negative | ND |
| 4 | Stage 1a | Negative | ND |
| 5 | Stage 1a | Negative | ND |
| 6 | Stage 1a | Negative | ND |
| 7 | Stage 1a | Negative | ND |
| 8 | Stage 1a | Negative | ND |
| 9 | Stage 1a | Negative | ND |
| 10 | Stage 1a | Negative | ND |
| 11 | Stage 1a | Negative | ND |
| 12 | Stage 1a | Negative | ND |
| 13 | Stage 1a | Negative | ND |
| 14 | Stage 1a | Negative | ND |
| 15 | Stage 1a | Negative | ND |
| 16 | Stage 1a | Negative | ND |
| 17 | Stage 1a | Negative | ND |
| 18 | Stage 1a | Negative | ND |
| 19 | Stage 1a | Negative | ND |
| 20 | Stage 1a | Negative | ND |
| 21 | Stage 1a | Negative | ND |
| 22 | Stage 1a | Negative | ND |
| 23 | Stage 1a | Negative | ND |
| 24 | Stage 1a | Negative | ND |
| 25 | Stage 1a | Negative | ND |
| 26 | Stage 1a | Negative | ND |
| 27 | Stage 1a | Negative | ND |
| 28 | Stage 1a | Negative | ND |
| 29 | Stage 1a | Negative | ND |
| 30 | Stage 1a | Negative | ND |
| 31 | Stage 1a | Negative | ND |
| 32 | Stage 1a | Negative | ND |
| 33 | Stage 1a | Negative | ND |
| 34 | Stage 1a | Negative | ND |
| 35 | Stage 1a | Negative | ND |
| 36 | Stage 1a | Negative | ND |
| 37 | Stage 1a | Negative | ND |
| 38 | Stage 1a | Negative | ND |
| 39 | Stage 1a | Negative | ND |
| 40 | Cytology positive | Positive | ND |
| 41 | Cytology positive | Positive | ND |
| 42 | Cytology positive | Positive | ND |
| 43 | Cytology positive | Positive | ND |
| 44 | Cytology positive | Positive | ND |
| 45 | Cytology positive | Positive | ND |
| 46 | Cytology positive | Positive | ND |
| 47 | Cytology positive | Positive | ND |
| 48 | Cytology positive | Positive | ND |
| 49 | Cytology positive | Positive | ND |
| 50 | Cytology positive | Positive | ND |
| 51 | Cytology positive | Positive | ND |
| 52 | Cytology positive | Positive | ND |
| 53 | Cytology positive | Positive | ND |
| 54 | Cytology positive | Positive | ND |
| 55 | Cytology positive | Positive | ND |
| 56 | Cytology positive | Positive | ND |
| 57 | Extra-peritoneal recurrence | Negative | ND |
| 58 | Extra-peritoneal recurrence | Negative | ND |
| 59 | Extra-peritoneal recurrence | Negative | ND |
| 60 | Extra-peritoneal recurrence | Negative | ND |
| 61 | Extra-peritoneal recurrence | Negative | ND |
| 62 | Extra-peritoneal recurrence | Negative | ND |
| 63 | Extra-peritoneal recurrence | Negative | ND |
| 64 | Extra-peritoneal recurrence | Negative | ND |
| 65 | Extra-peritoneal recurrence | Negative | ND |
| 66 | Extra-peritoneal recurrence | Negative | ND |
| 67 | Extra-peritoneal recurrence | Negative | ND |

TABLE 4-continued

Clinical data of samples used, etc.

| Sample number | Clinical information, etc. | Cytology | Immunostaining |
|---|---|---|---|
| 68 | Extra-peritoneal recurrence | Negative | ND |
| 69 | Extra-peritoneal recurrence | Negative | ND |
| 70 | Extra-peritoneal recurrence | Negative | ND |
| 71 | Extra-peritoneal recurrence | Negative | ND |
| 72 | Case of peritoneal recurrence | Negative | ND |
| 73 | Case of peritoneal recurrence | Negative | ND |
| 74 | Case of peritoneal recurrence | Negative | ND |
| 75 | Case of peritoneal recurrence | Negative | ND |
| 76 | Case of peritoneal recurrence | Negative | ND |
| 77 | Case of peritoneal recurrence | Negative | ND |
| 78 | Case of peritoneal recurrence | Negative | ND |
| 79 | Case of peritoneal recurrence | Negative | ND |
| 80 | Case of peritoneal recurrence | Negative | ND |
| 81 | Case of no recurrence | Negative | ND |
| 82 | Case of no recurrence | Negative | ND |
| 83 | Case of no recurrence | Negative | ND |
| 84 | Case of no recurrence | Negative | ND |
| 85 | Case of no recurrence | Negative | ND |
| 86 | Case of no recurrence | Negative | ND |
| 87 | Case of no recurrence | Negative | ND |
| 88 | Case of no recurrence | Negative | ND |
| 89 | Case of no recurrence | Negative | ND |
| 90 | Case of no recurrence | Negative | ND |
| 91 | Case of no recurrence | Negative | ND |
| 92 | Case of no recurrence | Negative | ND |
| 93 | Case of no recurrence | Negative | ND |
| 94 | Case of no recurrence | Negative | ND |
| 95 | Case of no recurrence | Negative | ND |
| 96 | Case of no recurrence | Negative | ND |
| 97 | Case of no recurrence | Negative | ND |
| 98 | Case of no recurrence | Negative | ND |
| 99 | Case of no recurrence | Negative | ND |
| 100 | Case of no recurrence | Negative | ND |
| 101 | Case of no recurrence | Negative | ND |
| 102 | Case of no recurrence | Negative | ND |
| 103 | Case of no recurrence | Negative | ND |
| 104 | Case of no recurrence | Negative | ND |
| 105 | Case of no recurrence | Negative | ND |
| 106 | Case of no recurrence | Negative | ND |
| 107 | Case of no recurrence | Negative | ND |
| 108 | Case of no recurrence | Negative | ND |
| 109 | Case of no recurrence | Negative | ND |
| 110 | Case of no recurrence | Negative | ND |
| 111 | Case of no recurrence | Negative | ND |
| 112 | Case of no recurrence | Negative | ND |
| 113 | Case of immunostaining positive | Positive | Positive |
| 114 | Case of immunostaining positive | Positive | Positive |
| 115 | Case of immunostaining positive | Positive | Positive |
| 116 | Case of immunostaining positive | Positive | Positive |
| 117 | Case of immunostaining positive | Positive | Positive |
| 118 | Case of immunostaining positive | Positive | Positive |

All disease-free patients were followed up at least 2 years. In table 4, cases where recurrences were suspected were judged by three routine imaging techniques (chest X-ray, abdominal ultrasonography, and computerized tomography scanning) and barium contrast enema. ND (not determined) means that there are no data.

Example 2

RT-PCR of Tumor Marker Gene (1) Single PCR

Amplification was confirmed by the primers shown in Table 3 using cDNA of gastric cancer cell KATOIII obtained in Example 1. PCR amplification was carried out by the conventional method using a commercially available kit manufactured by Invitrogen Corp. The composition of the reaction solution for the PCR amplification is shown in Table 5 below.

TABLE 5

Composition of reaction solution

| Component | Composition |
|---|---|
| AccuPrime Taq | 1.0 µl |
| 10x Reaction Buffer | 5.0 µl |
| Template DNA (cDNA solution) | 1.0 µl |
| Forward Primer | 12.5 pmol/each |
| Reverse Primer | 12.5 pmol/each |
| Distilled water | Up to 50 µl |
| Total | 50 µl |

PCR amplification reaction of the prepared reaction solutions was carried out according to the temperature cycle protocol of Table 6 shown below using a commercially available thermal cycler.

TABLE 6

Temperature conditions of PCR amplification reaction

| Step | Temperature | | Incubation time | Number of repeats |
|---|---|---|---|---|
| 1 | | 94° C. | 2 min. | |
| 2 | 94° C. | (denaturation) | 15 sec. | 30 cycles |
| 3 | 60° C. | (annealing) | 45 sec. | |
| 4 | 72° C. | (extension) | 3 min. | |

Each PCR product obtained was electrophoresed by Bioanalyzer-2100 (kits DNA12000) manufactured by Agilent Technologies, Inc. and visualized. Each of the PCR products was composed of a single band and the chain length was in agreement with the length shown in Table 3. This electrophoresis was carried out using DNA12000 manufactured by Agilent Technologies, Inc. and the standard method according to the manual provided from the manufacturer.

Multiplex RT-PCR

Next, PCR was carried out for amplifying and detecting cDNA of the genes described below using total cDNA of KATOIII as a template in a similar manner to Example 2 (1). Amplification of cDNA was carried out by the multiplex PCR method in which a plurality of primers were used in a same reaction solution. As primers, A group and B group described below, and 2 sets of primer sets were used independently to the same sample RNA or cDNA, and PCRs were carried out using different cycle numbers.

A group: TFF1, TFF2, FABP1, CK20, MUC2, CEA
B group: TACSTD1, MASPIN, PRSS4, GW112, ACTB The primes used for amplifying the genes in A group were SEQ ID NO: 12-NO: 21, NO: 26, and NO: 27. The primers used for amplifying the genes in B group were SEQ ID NO: 22-NO: 25, NO: 28-NO: 33.

Each primer was used at the predetermined concentration described below. The composition of the reaction solution is shown in Table 7.

TABLE 7

Composition of reaction solution

| Component | Composition |
|---|---|
| AccuPrime Taq | 1.0 µl |
| 10x Reaction Buffer | 5.0 µl |
| Template DNA (cDNA solution) | 1.0 µl |
| Forward Primer Mix | 12.5 pmol/each |
| Reverse Primer Mix | 12.5 pmol/each |

TABLE 7-continued

Composition of reaction solution

| Component | Composition |
|---|---|
| Distilled water | Up to 50 µl |
| Total | 50 µl |

PCR amplification reaction of the prepared reaction solutions was carried out according to the temperature cycle protocol of Table 8 shown below using a commercially available thermal cycler.

TABLE 8

Temperature conditions of PCR amplification reaction

| Step | Temperature | | Incubation time | Number of repeats |
|---|---|---|---|---|
| 1 | | 94° C. | 2 min. | |
| 2 | 94° C. | (denaturation) | 15 sec. | 30 cycles |
| 3 | 60° C. | (annealing) | 45 sec. | for A group |
| 4 | 72° C. | (extension) | 3 min. | 25 cycles for B group |

The PCR products of A and B groups were electrophoresed in a similar manner to Example 2-(1) using Bioanalyzer-2100 (kit: DNA12000) manufactured by Agilent Technologies, Inc. Results are shown in FIG. 1 below. In every PCR product, a plurality of bans were detected, and it was confirmed that any of the bands had chain length derived from the genes included in each primer set.

Example 3

Production of Chips (1) Washing of Glass Substrate

The glass substrate (size: 25 mm×75 mm×1 mm, made of synthetic quartz, Iiyama Special Glass Inc.) was placed in a heat and alkali resistant rack and immersed in a washing solution for ultrasonic washing, which was prepared at the predetermine concentration. After immersed overnight, the glass substrate was subjected to ultrasonic washing for 20 min. The substrate was taken out, rinsed in pure water lightly and then sonicated in ultra-pure water for 20 min. Next, the substrate was immersed for 10 min in 1N sodium hydroxide solution which was heated to 80° C., rinsed in pure water and washed in ultra-pure water again to obtain the quartz glass substrate for DNA microarray.

(2) Surface Treatment

Silane coupling agent, KBM-603 (Shin-Etsu Silicones Co. Ltd.) was dissolved in pure water at the concentration of 1% and stirred at room temperature for 2 hours. Then, the glass substrate washed as described above was immersed in the silane coupling solution and kept at room temperature for 20 min.

After being lifted from the silane solution and rinsed on the surface with pure water, the glass substrate was dried by blowing streams of nitrogen gas on both sides. The dried substrate was baked for 1 hour in an oven preheated to 120° C. to complete the coupling agent treatment and amino groups were introduced to the surface of the substrate. Next, N-(6-Maleimidocaproyloxy)succinimide (hereinafter abbreviated as EMCS) manufactured by Dojindo Laboratories was dissolved in a mixture of dimethylsulfoxide and ethanol (1:1). The solution was prepared at the final concentration of 0.3 mg/ml.

After the baking was completed, the glass substrate was cooled and immersed in the prepared EMCS solution at room temperature for 2 hours. By this treatment maleimide groups were introduced to the surface of the glass substrate by the reaction between the amino groups which were introduced to the surface by the silane coupling agent and succimide groups of EMCS. The glass substrate lifted from the EMCS solution was washed with the aforementioned solvent in which EMCS was dissolved and further with ethanol and then dried under the nitrogen gas atmosphere.

(3) Probe DNA

Oligonucleotide probes, the 5' termini of which were thiolated, were used as probe DNAs. These probes correspond to the 11 genes described in Table 1. The SEQ ID NOS of probes corresponding to the genes are as follows; The SEQ ID NO: 1 is a probe for detecting the TFF1 gene, NO: 2 is for the TFF2 gene, SEQ ID NO. 3 is for the FABP1 gene, SEQ ID NO: 4 is for the CK20 gene, SEQ ID NO: 5 is for the MUC2 gene, SEQ ID NO: 6 is for the CEA gene, SEQ ID NO: 7 is for the TACSTD1 gene, SEQ ID NO: 8 is for 40th MASPIN gene, SEQ ID NO: 9 is for the PRSS4 gene, SEQ ID NO: 10 is for the GW112 gene and SEQ ID NO: 11 is for the ACTB gene.

(4) Discharge of Probe DNA Solution by BJ Printer and Binding to Substrate

An aqueous solution containing 7.5 mass % of glycerin, 7.5 mass % of thiodiglycol, 7.5 mass % of urea, 1.0 mass % of acetylenol EH (Kawaken Fine Chemicals Co., Ltd.) was prepared. The 11 probes prepared earlier were dissolved in the above mixed solvent at a concentration of 5 μM. The DNA (probe) solution thus obtained was poured into a tank for a bubble jet printer (Commercial name: BJF-850, Canon Inc.), which is installed to the printer head.

Further, the bubble jet printer used here was modified so that printing on a flat board was possible. Still further, this bubble jet printer can spot about 5 picoliter of DNA solution at about 190 μm pitch, by inputting a printing pattern according to the predetermined file preparation method. Also, this printer was able to print 18 spots per one microarray for each probe.

Next, using this modified bubble jet printer, a DNA microarray was prepared by performing the printing operation to one glass substrate. After it is confirmed that printing operation was surely performed, the substrate was kept in a humidified chamber for 30 min to react maleimide groups on the surface of the glass substrate with thiol groups at the termini of the nucleic acid probe.

(5) Washing

After reacting 30 min, the substrate was washed with 10 mM phosphate buffer (pH 7.0) containing 100 mM NaCl to washout DNA solution remaining on the surface to obtain the DNA microarray made of glass substrate on which single stranded DNA was fixed.

Example 4

Multi-Sample Evaluation I (1) Multiplex PCR

Evaluation experiments were carried out using cDNAs, which were recovered in Example 1 (2), from 118 samples of the gastric cancer patients (collected at the National Cancer Center). PCR amplification was carried out by the multiplex PCR method using a plurality of primers in a same reaction solution as in Example 2 (2). As primers, A group and B group described below and 2 sets of primer sets were used for a same sample (cDNA) with different cycle number for PCR amplification. The SEQ ID NO of each primer is the same as shown in Example 2(2). To label the PCR products, 5-(3-aminoallyl) dUTP (manufactured by Ambion Ltd.) was added to the reaction solution for PCR as a substrate. The composition of the reaction solution is in Table 9 shown below.

A group: TFF1, TFF2, FABP1, CK20, MUC2, CEA
B group: TACSTD1, MASPIN, PRSS4, GW112, ACTB

TABLE 9

| Composition of reaction solution | |
|---|---|
| Component | Composition |
| AccuPrime Taq | 0.25 μl |
| 10x Reaction Buffer | 1.0 μl |
| Template DNA (cDNA solution) | 1 μl |
| Forward Primer (F) | 2.5 pmol/each |
| Reverse Primer (R) | 2.5 pmol/each |
| Aminoallyl dUTP | 0.5 nmol/each |
| Distilled water | Up to 10 μl |
| Total | 10 μl |

PCR amplification reaction of the prepared reaction solutions was carried out according to the temperature cycle protocol of Table 10 shown below using a commercially available thermal cycler.

TABLE 10

| Temperature conditions of PCR amplification reaction | | | |
|---|---|---|---|
| Step | Temperature | Incubation time | Number of repeats |
| 1 | 94° C. | 2 min. | |
| 2 | 94° C. (denaturation) | 15 sec. | 30 cycles for A group |
| 3 | 60° C. (annealing) | 45 sec. | 25 cycles for B group |
| 4 | 72° C. (extension) | 3 min. | |

Purification was carried out using QIAquick PCR Purification Kit manufactured by Qiagen Inc. after mixing the crudely purified two PCR products of A group and B group for each template. Purification was carried out according to the procedure of the manual attached to the kit and final elution was performed with 50 μl of distilled water.

(2) Cy3 Label

Cy3 labeling was carried out for obtained aminoallyl labeled PCR products. In particular, the following procedure was used. The purified aminoallyl labeled PCR products obtained in (1) was dried up using a centrifugal concentrator. The dried up PCR product was dissolved completely in 9 μl of 0.2M carbonate buffer (pH 9.0). To the solution, 2 μl of the Cy3 labeling reagent was added and stirred at room temperature in the dark place for 1 hour. Here, Cy3 Mono-reactive NHS ester manufactured by Amersham Bioscience Corp. was used as the Cy3 labeling reagent, which was prepared by dissolving one bottle in the kit in 50 μl of dimethylsulfoxide. After stirring for 1 hour, 2 μl of the Cy3 labeling reagent was added and the mixture was further stirred at room temperature in the dark place for 1 hour. Then, the reaction was stopped by adding 37 μl of distilled water to obtain crude Cy3 labeled PCR product. The crude product was purified, as in (1), using a purification kit, QIAquickPCR Purification Kit manufactured by Qiagen Inc. Final elution was carried out with 50 μl of distilled water.

(3) Hybridization of Microarray

Whole Cy3 labeled PCR product obtained was mixed with buffer and the like to prepare the hybridization solution having the following final concentrations.

<Hybridization Solution>

6×SSPE/10% formamide/0.05% SDS/PCR amplification product solution (Composition of 6×SSPE: NaCl 900 mM, $NaH_2PO_4 \cdot H_2O$ 60 mM, EDTA 6 mM, pH 7.4)

The DNA microarray produced in Example 3 was set in a hybridization device Genomic Solutions Inc. Hybridization Station), and the hybridization reaction was carried out using the hybridization solution described above and according to the procedures and conditions described in Table 11 below.

TABLE 11

| Hybridization procedures and conditions | |
|---|---|
| Operation | Operation procedure and condition |
| Stabilization | 65° C. 3 min (Hybridization solution added after stabilization) |
| Reaction | 92° C. 2 min → 55° C. 4 h |

TABLE 11-continued

| Hybridization procedures and conditions | |
|---|---|
| Operation | Operation procedure and condition |
| Washing | 2×SSC/0.1% SDS at 25° C. |
|  | 2×SSC at 20° C. |
| Rinsing | Surface rinsed with 0.1% SSC |
| Water removal | Spin drying |

After the hybridization reaction was completed, the spin dried DNA microarray was subjected to fluorescent measurements for each probe using a fluorescent detector for DNA microarray (Genepix 4000B, Axon Inc.). Result of the measurement of fluorescent luminance is shown in Table 11.

In calculating the luminance, the background value, which was the fluorescence intensity of the area surrounding the probe (spot) was subtracted from the intensity from each spot to obtain the real measured intensity. From each probe, 18 intensities were obtained, and the mean value was calculated for each probe as the fluorescence intensity.

Tables 12-1 to 12-4 shows the fluorescence intensities of 118 cases and to make a correction for the influence of the scattering of the amount of the template on the intensity, ACTB was amplified at the same time.

TABLE 12-1

| Fluorescence intensities of cases | | | | | | | | | | | |
|---|---|---|---|---|---|---|---|---|---|---|---|
| Sample | Gene name and intensity | | | | | | | | | | |
| number | CEA | TFF1 | TFF2 | FABP1 | CK20 | Muc2 | PRSS4 | GW112 | MASPIN | TACSTD1 | ACTB |
| 1 | 7.8 | 2.1 | 0.7 | 3.2 | 1.2 | 45.2 | 4.9 | 144.6 | 147.9 | 20.6 | 5604.9 |
| 2 | 6.3 | 1.4 | 2.6 | 2.2 | 0.9 | 211.2 | 3.5 | 206.8 | 237.0 | 15.8 | 4573.8 |
| 3 | 11.0 | 14.6 | 2.0 | 1.1 | 0.8 | 209.0 | 8.3 | 38.3 | 43.4 | 12.2 | 4825.9 |
| 4 | 3.2 | 1.0 | 1.3 | 1.5 | 3.4 | 27.3 | 2.1 | 27.4 | 24.2 | 16.9 | 3962.9 |
| 5 | 9.7 | 2.8 | 1.7 | 57.2 | 1.8 | 4.8 | 2.1 | 17.7 | 15.3 | 9.9 | 3655.5 |
| 6 | 15.8 | 20.3 | 2.8 | 3.4 | 3.1 | 34.2 | 6.7 | 14.9 | 15.2 | 14.3 | 3892.2 |
| 7 | 13.4 | 30.4 | 39.8 | 3.9 | 2.2 | 196.7 | 5.9 | 55.2 | 55.3 | 12.8 | 4645.7 |
| 8 | 4.6 | 2.5 | 2.5 | 2.7 | 2.2 | 7.0 | 3.0 | 23.6 | 16.2 | 3.3 | 3090.9 |
| 9 | 13.9 | 2.4 | 11.1 | 3.2 | 3.1 | 109.8 | 6.3 | 328.6 | 355.6 | 11.8 | 3921.0 |
| 10 | 8.1 | 2.6 | 3.1 | 3.7 | 2.3 | 586.3 | 4.6 | 107.9 | 99.7 | 22.8 | 3823.8 |
| 11 | 5.1 | 12.3 | 39.6 | 3.1 | 2.6 | 47.6 | 4.9 | 141.3 | 122.9 | 10.7 | 4533.6 |
| 12 | 11.7 | 3.2 | 38.7 | 5.3 | 2.5 | 26.7 | 6.9 | 38.5 | 37.6 | 8.2 | 3927.1 |
| 13 | 5.5 | 1.7 | 2.2 | 24.7 | 0.4 | 11.5 | 2.8 | 68.9 | 64.8 | 6.1 | 2951.0 |
| 14 | 6.8 | 3.7 | 2.9 | 1.2 | 4.2 | 5.7 | 5.8 | 13.9 | 12.2 | 3.0 | 281.7 |
| 15 | 6.7 | 0.8 | 1.4 | 2.1 | 0.6 | 8.3 | 2.6 | 130.1 | 172.3 | 2.3 | 1872.2 |
| 16 | 19.2 | 1.9 | 3.9 | 2.9 | 1.1 | 9.0 | 8.4 | 1099.4 | 643.5 | 6.0 | 2392.6 |
| 17 | 13.7 | 0.0 | 0.0 | 0.3 | 0.0 | 13.7 | 0.0 | 373.1 | 301.6 | 4.2 | 438.9 |
| 18 | 7.4 | 1.6 | 1.6 | 2.7 | 1.2 | 5.0 | 4.4 | 74.7 | 78.6 | 1.5 | 2028.1 |
| 19 | 2.3 | 35.1 | 10.0 | 37.4 | 1.2 | 84.5 | 4.2 | 23.3 | 23.2 | 1.9 | 1523.4 |
| 20 | 1.0 | 38.1 | 41.6 | 5.6 | 0.0 | 9.0 | 7.7 | 4.2 | 3.4 | 28.0 | 1711.8 |
| 21 | 6.7 | 23.5 | 8.7 | 45.6 | 2.3 | 13.2 | 9.5 | 33.6 | 29.0 | 8.8 | 1450.4 |
| 22 | 7.2 | 14.5 | 25.6 | 2.4 | 2.1 | 2958.4 | 83.0 | 1847.9 | 1024.2 | 20.2 | 2553.5 |
| 23 | 3.1 | 6.2 | 5.9 | 8.1 | 2.8 | 3999.2 | 287.4 | 3721.3 | 2525.2 | 85.2 | 2361.3 |
| 24 | 4.5 | 43.2 | 73.7 | 8.0 | 2.7 | 1379.2 | 455.9 | 2883.2 | 1755.2 | 64.1 | 2268.9 |
| 25 | 5.4 | 52.2 | 60.7 | 0.9 | 2.0 | 25.2 | 5.5 | 10.8 | 10.8 | 2.8 | 2406.6 |
| 26 | 10.4 | 62.0 | 41.8 | 3.8 | 2.3 | 482.2 | 59.4 | 918.2 | 526.0 | 20.7 | 2445.2 |
| 27 | 6.9 | 56.4 | 234.8 | 7.5 | 3.1 | 2398.2 | 296.2 | 4079.4 | 1956.3 | 122.0 | 2242.8 |
| 28 | 4.0 | 84.0 | 1.0 | 4.5 | 0.9 | 196.4 | 3.9 | 4.8 | 0.0 | 19.6 | 2673.2 |
| 29 | 6.1 | 36.1 | 71.1 | 4.2 | 2.7 | 219.4 | 16.6 | 4.7 | 1.6 | 49.3 | 2814.8 |
| 30 | 8.1 | 10.2 | 153.2 | 9.2 | 4.7 | 3696.8 | 336.4 | 3438.3 | 2216.7 | 46.5 | 2487.1 |

TABLE 12-2

Fluorescence intensities of cases

| Sample number | CEA | TFF1 | TFF2 | FABP1 | CK20 | Muc2 | PRSS4 | GW112 | MASPIN | TACSTD1 | ACTB |
|---|---|---|---|---|---|---|---|---|---|---|---|
| 31 | 22.5 | 3.7 | 4.1 | 5.1 | 3.3 | 33.6 | 12.3 | 122.4 | 39.0 | 13.1 | 2282.6 |
| 32 | 17.4 | 36.4 | 60.9 | 6.8 | 5.5 | 315.2 | 35.7 | 266.0 | 96.3 | 18.3 | 2685.1 |
| 33 | 12.5 | 17.4 | 21.7 | 4.5 | 3.5 | 581.5 | 46.1 | 154.4 | 86.3 | 10.4 | 2335.7 |
| 34 | 10.8 | 35.6 | 90.1 | 6.0 | 3.9 | 951.9 | 116.2 | 1612.2 | 676.7 | 16.5 | 2230.3 |
| 35 | 4.1 | 70.7 | 1.8 | 2.5 | 2.3 | 9.4 | 4.5 | 6.3 | 4.1 | 17.7 | 2890.8 |
| 36 | 0.3 | 85.2 | 18.1 | 0.0 | 1.2 | 30.3 | 3.8 | 24.4 | 27.0 | 0.0 | 1279.6 |
| 37 | 5.6 | 57.1 | 3.8 | 3.0 | 2.2 | 61.5 | 2.9 | 10.1 | 8.1 | 7.9 | 2100.9 |
| 38 | 17.9 | 1.4 | 1.8 | 4.1 | 1.5 | 72.5 | 6.8 | 195.4 | 228.0 | 15.2 | 2424.8 |
| 39 | 12.3 | 12.9 | 31.2 | 3.1 | 0.1 | 2170.3 | 25.7 | 327.7 | 239.1 | 24.0 | 2710.1 |
| 40 | 12.5 | 575.4 | 234.6 | 4147.8 | 52.6 | 40.7 | 137.6 | 567.7 | 46.0 | 224.9 | 3650.4 |
| 41 | 29.6 | 1.4 | 1.3 | 1.6 | 1.0 | 2.0 | 1.4 | 116.9 | 121.1 | 138.7 | 3286.6 |
| 42 | 25.6 | 192.5 | 55.7 | 2.4 | 1.4 | 3.3 | 6.6 | 40.2 | 54.7 | 117.2 | 2138.8 |
| 43 | 12.9 | 3191.7 | 3188.2 | 6728.8 | 130.0 | 5078.8 | 903.7 | 177.4 | 22.6 | 929.4 | 4264.9 |
| 44 | 8.4 | 1348.9 | 2874.1 | 3065.3 | 137.1 | 21.8 | 227.7 | 51.7 | 19.4 | 89.3 | 3238.4 |
| 45 | 46.7 | 260.0 | 161.2 | 55.1 | 3.0 | 5.8 | 16.2 | 48.5 | 61.7 | 29.8 | 4234.1 |
| 46 | 14.8 | 92.8 | 20.6 | 73.3 | 155.0 | 3.3 | 14.3 | 6.1 | 6.2 | 43.6 | 2000.3 |
| 47 | 6.5 | 2293.4 | 756.3 | 49.9 | 50.5 | 2718.8 | 1212.7 | 29.8 | 53.8 | 661.8 | 2039.8 |
| 48 | 14.6 | 1148.1 | 957.5 | 298.1 | 3.5 | 107.0 | 16.7 | 140.6 | 107.7 | 72.5 | 3463.0 |
| 49 | 10.7 | 1886.6 | 173.7 | 5.1 | 14.6 | 287.8 | 475.2 | 344.5 | 9.9 | 1099.4 | 5378.9 |
| 50 | 74.3 | 1571.4 | 689.4 | 165.4 | 3.7 | 27.8 | 95.5 | 74.0 | 52.5 | 145.5 | 4691.3 |
| 51 | 106.6 | 361.7 | 215.5 | 37.3 | 2.3 | 12.3 | 3.2 | 39.8 | 42.2 | 7.5 | 1852.6 |
| 52 | 7.8 | 1130.6 | 388.6 | 560.6 | 57.1 | 133.9 | 735.7 | 543.5 | 9.7 | 633.0 | 2789.5 |
| 53 | 10.0 | 37.3 | 1.5 | 39.7 | 158.1 | 190.1 | 33.5 | 4.2 | 7.0 | 91.6 | 2740.7 |
| 54 | 15.5 | 151.4 | 54.7 | 287.6 | 15.4 | 225.0 | 4.8 | 5.2 | 3.8 | 40.1 | 1760.8 |
| 55 | 19.7 | 28.7 | 112.3 | 971.7 | 212.9 | 33.8 | 12.4 | 23.1 | 16.6 | 100.5 | 1948.0 |
| 56 | 5.0 | 47.9 | 91.2 | 28.6 | 1.9 | 2.6 | 2.9 | 232.9 | 136.7 | 2.6 | 724.5 |
| 57 | 5.1 | 1.4 | 48.6 | 2.1 | 1.4 | 9.9 | 2.4 | 165.4 | 212.8 | 6.2 | 3654.5 |
| 58 | 3.5 | 1.2 | 1.5 | 2.0 | 1.9 | 13.5 | 3.7 | 128.8 | 141.5 | 19.7 | 3103.0 |
| 59 | 8.4 | 90.2 | 27.2 | 1230.6 | 848.6 | 26.9 | 437.1 | 308.5 | 408.4 | 139.5 | 3658.1 |
| 60 | 8.0 | 0.0 | 0.4 | 27.4 | 2.1 | 26.7 | 3.8 | 685.8 | 563.1 | 3.0 | 2388.4 |

TABLE 12-3

Fluorescence intensities of cases

| Sample number | CEA | TFF1 | TFF2 | FABP1 | CK20 | Muc2 | PRSS4 | GW112 | MASPIN | TACSTD1 | ACTB |
|---|---|---|---|---|---|---|---|---|---|---|---|
| 61 | 4.5 | 4.1 | 200.3 | 13.9 | 1.1 | 3838.8 | 814.6 | 12032.6 | 8892.0 | 72.1 | 4750.1 |
| 62 | 5.6 | 18.0 | 2.2 | 1.8 | 2.1 | 39.1 | 1.8 | 91.5 | 68.1 | 73.1 | 3943.7 |
| 63 | 7.7 | 1.9 | 3.4 | 24.8 | 1.9 | 10.1 | 3.2 | 138.2 | 151.1 | 1.7 | 1999.8 |
| 64 | 11.4 | 439.3 | 407.0 | 1600.8 | 77.2 | 8.6 | 38.7 | 328.6 | 82.2 | 142.6 | 3381.4 |
| 65 | 16.7 | 4.5 | 3.1 | 5.4 | 3.9 | 6.2 | 3.8 | 238.3 | 305.2 | 6.9 | 2970.8 |
| 66 | 32.2 | 24.3 | 1.8 | 4.6 | 1.6 | 5.0 | 2.0 | 124.7 | 135.4 | 5.2 | 3431.1 |
| 67 | 49.3 | 14.2 | 2.3 | 2.2 | 2.2 | 2.2 | 0.9 | 87.6 | 58.0 | 2.0 | 2212.4 |
| 68 | 87.8 | 57.6 | 3.0 | 98.9 | 6.8 | 68.3 | 2.0 | 23.7 | 15.6 | 7.9 | 1683.3 |
| 69 | 3.6 | 2.0 | 2.7 | 2.9 | 3.2 | 6.1 | 8.9 | 36.5 | 42.5 | 11.9 | 2979.0 |
| 70 | 5.1 | 47.7 | 23.9 | 33.6 | 0.9 | 24.3 | 6.4 | 579.4 | 443.2 | 9.2 | 1660.4 |
| 71 | 5.1 | 41.5 | 71.4 | 45.5 | 1.6 | 7.6 | 2.2 | 101.9 | 103.4 | 1.9 | 1439.3 |
| 72 | 29.9 | 398.7 | 6.1 | 178.0 | 146.3 | 748.9 | 13.0 | 313.3 | 226.2 | 87.5 | 4125.5 |
| 73 | 32.9 | 2.7 | 3.1 | 26.4 | 6.6 | 5.2 | 3.9 | 812.7 | 592.2 | 22.0 | 3201.6 |
| 74 | 33.1 | 33.2 | 40.1 | 1.8 | 1.8 | 27.8 | 3.3 | 82.3 | 91.8 | 14.4 | 3422.7 |
| 75 | 203.0 | 73.6 | 2.3 | 2.5 | 1.8 | 11.6 | 3.6 | 71.7 | 50.5 | 28.9 | 2236.5 |
| 76 | 212.1 | 237.1 | 1.2 | 210.7 | 43.0 | 73.5 | 2.0 | 39.6 | 35.0 | 32.1 | 3133.2 |
| 77 | 29.3 | 5.0 | 5.3 | 6.4 | 4.0 | 112.0 | 6.9 | 797.0 | 658.1 | 30.9 | 3874.9 |
| 78 | 53.6 | 2.5 | 9.2 | 48.0 | 2.2 | 3.7 | 2.6 | 24.5 | 11.6 | 11.7 | 2625.9 |
| 79 | 25.2 | 1.8 | 1.6 | 3.6 | 3.0 | 3.0 | 2.4 | 9.4 | 5.1 | 26.9 | 3899.2 |
| 80 | 6.8 | 98.3 | 43.5 | 37.6 | 3.0 | 7.9 | 3.9 | 103.9 | 107.6 | 3.8 | 614.5 |
| 81 | 1.3 | 1.4 | 0.7 | 1.2 | 0.4 | 24.6 | 2.5 | 15.0 | 10.2 | 32.6 | 3608.6 |
| 82 | 50.5 | 43.1 | 2.8 | 3.8 | 2.4 | 17.0 | 4.1 | 99.9 | 76.1 | 8.8 | 4491.3 |
| 83 | 15.0 | 3.5 | 3.1 | 2.5 | 2.9 | 60.4 | 6.4 | 674.9 | 482.8 | 18.7 | 3616.7 |
| 84 | 14.8 | 1.9 | 1.5 | 2.6 | 1.1 | 84.6 | 7.5 | 235.6 | 165.2 | 2.1 | 3394.1 |
| 85 | 6.7 | 2.2 | 3.1 | 40.1 | 2.6 | 55.5 | 5.1 | 48.9 | 42.6 | 7.3 | 3551.1 |
| 86 | 8.1 | 2.7 | 4.7 | 4.0 | 2.0 | 178.2 | 5.8 | 78.8 | 90.8 | 15.8 | 3676.4 |
| 87 | 14.6 | 4.0 | 5.6 | 5.5 | 3.8 | 35.7 | 6.0 | 194.6 | 212.4 | 4.8 | 3238.7 |
| 88 | 35.7 | 29.9 | 3.5 | 54.1 | 3.3 | 5.7 | 12.4 | 163.7 | 146.5 | 24.6 | 2732.6 |
| 89 | 5.1 | 1.7 | 61.3 | 2.7 | 1.1 | 79.3 | 3.7 | 244.0 | 246.7 | 5.8 | 2864.2 |
| 90 | 7.2 | 1.3 | 1.0 | 1.6 | 1.2 | 5.9 | 6.9 | 147.8 | 63.7 | 10.5 | 3908.3 |

TABLE 12-4

Fluorescence intensities of cases

| Sample number | CEA | TFF1 | TFF2 | FABP1 | CK20 | Muc2 | PRSS4 | GW112 | MASPIN | TACSTD1 | ACTB |
|---|---|---|---|---|---|---|---|---|---|---|---|
| 91 | 3.1 | 7.8 | 3.4 | 3.4 | 2.8 | 6.7 | 3.2 | 14.1 | 16.6 | 5.6 | 1351.8 |
| 92 | 93.2 | 4.4 | 12.6 | 56.4 | 3.6 | 5.6 | 33.9 | 166.2 | 113.1 | 61.0 | 4970.6 |
| 93 | 15.8 | 4.1 | 3.1 | 3.7 | 3.2 | 5.9 | 4.9 | 89.3 | 74.2 | 4.6 | 3856.7 |
| 94 | 16.1 | 3.9 | 4.0 | 9.6 | 4.1 | 6.9 | 29.0 | 286.7 | 403.4 | 16.3 | 4666.8 |
| 95 | 38.4 | 152.5 | 86.0 | 3.1 | 3.0 | 4.8 | 21.4 | 1844.9 | 1187.1 | 17.8 | 1782.2 |
| 96 | 10.1 | 2.1 | 117.3 | 7.1 | 0.9 | 532.1 | 610.6 | 7528.2 | 5207.3 | 30.6 | 4089.0 |
| 97 | 69.4 | 361.6 | 3.8 | 19.9 | 6.7 | 4.7 | 3.6 | 26.7 | 16.7 | 12.6 | 3767.3 |
| 98 | 19.8 | 1.2 | 1.3 | 2.7 | 0.3 | 2.1 | 1.1 | 2.7 | 2.0 | 1.6 | 3612.6 |
| 99 | 7.3 | 1.6 | 2.3 | 1.8 | 1.7 | 5.2 | 3.8 | 22.1 | 24.0 | 2.5 | 3660.5 |
| 100 | 7.0 | 16.9 | 44.2 | 2.0 | 1.9 | 4.6 | 3.4 | 64.8 | 35.4 | 9.6 | 3639.1 |
| 101 | 4.3 | 0.0 | 0.0 | 0.9 | 0.0 | 1.5 | 1.9 | 6.5 | 1.7 | 13.1 | 4273.0 |
| 102 | 5.2 | 0.0 | 12.0 | 0.9 | 0.1 | 2.4 | 0.0 | 49.8 | 49.4 | 11.8 | 2462.5 |
| 103 | 0.0 | 0.0 | 0.0 | 0.0 | 0.0 | 0.0 | 0.0 | 11.5 | 7.3 | 7.3 | 4472.1 |
| 104 | 24.2 | 16.2 | 2.3 | 2.0 | 2.2 | 1.5 | 1.0 | 17.4 | 17.4 | 1.0 | 4187.8 |
| 105 | 33.0 | 14.6 | 2.9 | 3.9 | 2.3 | 24.9 | 6.8 | 560.4 | 572.7 | 11.4 | 2066.8 |
| 106 | 5.3 | 15.4 | 3.1 | 2.9 | 0.9 | 2.6 | 1.8 | 43.7 | 34.4 | 1.5 | 1945.7 |
| 107 | 15.9 | 3.1 | 3.8 | 4.1 | 2.6 | 4.3 | 4.0 | 36.8 | 42.3 | 3.5 | 1173.3 |
| 108 | 3.1 | 40.3 | 118.6 | 18.0 | 0.0 | 0.0 | 2.3 | 8.8 | 10.6 | 8.2 | 2376.4 |
| 109 | 2.7 | 14.8 | 1.3 | 2.2 | 0.9 | 17.8 | 4.6 | 82.4 | 109.3 | 3.5 | 622.0 |
| 110 | 4.9 | 25.9 | 58.1 | 23.5 | 1.3 | 10.0 | 2.6 | 71.4 | 98.9 | 2.6 | 1772.0 |
| 111 | 0.0 | 40.2 | 67.1 | 31.4 | 0.0 | 0.0 | 0.0 | 233.7 | 281.2 | 0.0 | 1934.5 |
| 112 | 4.4 | 37.0 | 107.5 | 32.0 | 0.7 | 1.9 | 3.8 | 388.7 | 285.1 | 2.0 | 1676.6 |
| 113 | 2.1 | 269.5 | 81.3 | 142.8 | 11.4 | 252.5 | 335.8 | 2.3 | 14.8 | 238.3 | 1387.9 |
| 114 | 11.7 | 265.8 | 242.2 | 30.0 | 912.3 | 207.7 | 451.5 | 4.5 | 7.5 | 306.4 | 1881.7 |
| 115 | 12.1 | 114.8 | 104.1 | 24.0 | 2.5 | 937.5 | 29.9 | 174.1 | 124.4 | 37.9 | 1144.6 |
| 116 | 5.1 | 704.5 | 744.6 | 2762.7 | 379.8 | 663.2 | 650.9 | 30.4 | 36.9 | 433.8 | 2645.9 |
| 117 | 6.1 | 899.1 | 746.3 | 704.2 | 18.7 | 1618.4 | 155.2 | 164.3 | 148.4 | 169.7 | 1553.9 |
| 118 | 11.4 | 376.8 | 285.6 | 55.6 | 3.3 | 33.3 | 55.8 | 33.0 | 38.3 | 64.9 | 1291.2 |

To reduce scattering of sample's measured intensities due to the difference in the amount of the template, the standardization by the intensity of ACTB of each sample was carried out. "Standardized intensity" was obtained by dividing the intensity of the each gene by the intensity of ACTB in each sample, and the results are shown in Tables 13-1 to 13-4.

TABLE 13-3

Standardized intensities of cases

| Sample number | CEA | TFF1 | TFF2 | FABP1 | CK20 | Muc2 | PRSS4 | GW112 | MASPIN | TACSTD1 | ACTB |
|---|---|---|---|---|---|---|---|---|---|---|---|
| 61 | 0.94 | 0.86 | 42.16 | 2.92 | 0.23 | 808.14 | 171.50 | 2533.11 | 1871.95 | 15.17 | 1000 |
| 62 | 1.41 | 4.55 | 0.57 | 0.46 | 0.53 | 9.91 | 0.44 | 23.19 | 17.27 | 18.53 | 1000 |
| 63 | 3.85 | 0.95 | 1.70 | 12.39 | 0.93 | 5.05 | 1.61 | 69.10 | 75.56 | 0.84 | 1000 |
| 64 | 3.36 | 129.92 | 120.37 | 473.41 | 22.84 | 2.54 | 11.45 | 97.19 | 24.32 | 42.16 | 1000 |
| 65 | 5.61 | 1.51 | 1.03 | 1.83 | 1.31 | 2.10 | 1.26 | 80.20 | 102.72 | 2.31 | 1000 |
| 66 | 9.39 | 7.07 | 0.51 | 1.34 | 0.45 | 1.46 | 0.58 | 36.35 | 39.45 | 1.51 | 1000 |
| 67 | 22.29 | 6.41 | 1.06 | 0.98 | 0.98 | 1.00 | 0.39 | 39.59 | 26.20 | 0.92 | 1000 |
| 68 | 52.13 | 34.21 | 1.78 | 58.74 | 4.05 | 40.55 | 1.19 | 14.07 | 9.28 | 4.72 | 1000 |
| 69 | 1.22 | 0.69 | 0.92 | 0.96 | 1.06 | 2.06 | 2.99 | 12.27 | 14.26 | 4.00 | 1000 |
| 70 | 3.10 | 28.74 | 14.38 | 20.24 | 0.53 | 14.63 | 3.83 | 348.97 | 266.92 | 5.54 | 1000 |
| 71 | 3.56 | 28.80 | 49.62 | 32.34 | 1.14 | 5.26 | 1.53 | 70.83 | 71.84 | 1.31 | 1000 |
| 72 | 7.25 | 96.65 | 1.48 | 43.14 | 35.47 | 181.53 | 3.15 | 75.94 | 54.83 | 21.22 | 1000 |
| 73 | 10.29 | 0.84 | 0.97 | 8.24 | 2.05 | 1.63 | 1.21 | 253.85 | 184.98 | 6.86 | 1000 |
| 74 | 9.66 | 9.69 | 11.71 | 0.52 | 0.53 | 8.12 | 0.98 | 24.04 | 26.81 | 4.21 | 1000 |
| 75 | 90.78 | 32.90 | 1.02 | 1.10 | 0.80 | 5.18 | 1.62 | 32.05 | 22.59 | 12.93 | 1000 |
| 76 | 67.70 | 75.68 | 0.39 | 67.26 | 13.71 | 23.46 | 0.65 | 12.65 | 11.18 | 10.25 | 1000 |
| 77 | 7.57 | 1.28 | 1.37 | 1.65 | 1.03 | 28.90 | 1.79 | 205.68 | 169.84 | 7.98 | 1000 |
| 78 | 20.40 | 0.96 | 3.50 | 18.29 | 0.83 | 1.42 | 1.01 | 9.31 | 4.43 | 4.45 | 1000 |
| 79 | 6.46 | 0.46 | 0.38 | 0.91 | 0.77 | 0.78 | 0.61 | 2.41 | 1.30 | 6.90 | 1000 |
| 80 | 11.10 | 159.97 | 70.78 | 61.17 | 4.91 | 12.87 | 6.27 | 169.08 | 175.04 | 6.11 | 1000 |
| 81 | 0.36 | 0.38 | 0.18 | 0.32 | 0.10 | 6.83 | 0.68 | 4.15 | 2.82 | 9.04 | 1000 |
| 82 | 11.25 | 9.59 | 0.62 | 0.84 | 0.54 | 3.78 | 0.91 | 22.25 | 16.94 | 1.95 | 1000 |
| 83 | 4.16 | 0.98 | 0.86 | 0.69 | 0.79 | 16.71 | 1.78 | 186.61 | 133.49 | 5.17 | 1000 |
| 84 | 4.37 | 0.57 | 0.43 | 0.77 | 0.32 | 24.94 | 2.22 | 69.41 | 48.67 | 0.61 | 1000 |
| 85 | 1.88 | 0.63 | 0.87 | 11.30 | 0.72 | 15.62 | 1.45 | 13.77 | 12.01 | 2.07 | 1000 |
| 86 | 2.21 | 0.72 | 1.27 | 1.10 | 0.53 | 48.46 | 1.57 | 21.44 | 24.71 | 4.31 | 1000 |
| 87 | 4.51 | 1.25 | 1.73 | 1.69 | 1.16 | 11.02 | 1.85 | 60.08 | 65.58 | 1.48 | 1000 |
| 88 | 13.05 | 10.94 | 1.30 | 19.79 | 1.22 | 2.09 | 4.53 | 59.94 | 53.61 | 9.02 | 1000 |

TABLE 13-3-continued

Standardized intensities of cases

| Sample number | Gene name and standardized intensity (×1000) | | | | | | | | | | |
|---|---|---|---|---|---|---|---|---|---|---|---|
| | CEA | TFF1 | TFF2 | FABP1 | CK20 | Muc2 | PRSS4 | GW112 | MASPIN | TACSTD1 | ACTB |
| 89 | 1.78 | 0.61 | 21.42 | 0.95 | 0.39 | 27.67 | 1.29 | 85.20 | 86.11 | 2.03 | 1000 |
| 90 | 1.84 | 0.32 | 0.26 | 0.40 | 0.31 | 1.51 | 1.78 | 37.81 | 16.29 | 2.70 | 1000 |

TABLE 13-1

Standardized intensities of cases

| Sample number | Gene name and standardized intensity (×1000) | | | | | | | | | | |
|---|---|---|---|---|---|---|---|---|---|---|---|
| | CEA | TFF1 | TFF2 | FABP1 | CK20 | Muc2 | PRSS4 | GW112 | MASPIN | TACSTD1 | ACTB |
| 1 | 1.39 | 0.37 | 0.13 | 0.58 | 0.22 | 8.06 | 0.88 | 25.80 | 26.39 | 3.67 | 1000 |
| 2 | 1.38 | 0.32 | 0.56 | 0.49 | 0.20 | 46.17 | 0.76 | 45.21 | 51.82 | 3.45 | 1000 |
| 3 | 2.28 | 3.04 | 0.42 | 0.22 | 0.17 | 43.32 | 1.72 | 7.94 | 8.99 | 2.53 | 1000 |
| 4 | 0.82 | 0.26 | 0.32 | 0.38 | 0.86 | 6.89 | 0.52 | 6.91 | 6.11 | 4.27 | 1000 |
| 5 | 2.66 | 0.77 | 0.45 | 15.66 | 0.49 | 1.31 | 0.57 | 4.86 | 4.20 | 2.72 | 1000 |
| 6 | 4.05 | 5.22 | 0.73 | 0.88 | 0.79 | 8.78 | 1.72 | 3.83 | 3.91 | 3.68 | 1000 |
| 7 | 2.88 | 6.55 | 8.56 | 0.84 | 0.47 | 42.35 | 1.27 | 11.89 | 11.91 | 2.75 | 1000 |
| 8 | 1.47 | 0.80 | 0.81 | 0.88 | 0.71 | 2.28 | 0.96 | 7.54 | 5.25 | 1.06 | 1000 |
| 9 | 3.54 | 0.60 | 2.83 | 0.81 | 0.79 | 27.99 | 1.62 | 83.81 | 90.69 | 3.00 | 1000 |
| 10 | 2.13 | 0.69 | 0.82 | 0.96 | 0.60 | 153.33 | 1.21 | 28.22 | 26.06 | 5.95 | 1000 |
| 11 | 1.13 | 2.71 | 8.74 | 0.68 | 0.58 | 10.50 | 1.07 | 31.16 | 27.12 | 2.37 | 1000 |
| 12 | 2.99 | 0.82 | 9.87 | 1.34 | 0.64 | 6.80 | 1.76 | 9.81 | 9.57 | 2.08 | 1000 |
| 13 | 1.87 | 0.57 | 0.76 | 8.37 | 0.13 | 3.90 | 0.95 | 23.34 | 21.94 | 2.08 | 1000 |
| 14 | 23.98 | 12.97 | 10.47 | 4.37 | 14.84 | 20.10 | 20.59 | 49.32 | 43.41 | 10.58 | 1000 |
| 15 | 3.55 | 0.45 | 0.74 | 1.10 | 0.30 | 4.45 | 1.37 | 69.47 | 92.04 | 1.21 | 1000 |
| 16 | 8.01 | 0.78 | 1.64 | 1.21 | 0.46 | 3.76 | 3.50 | 459.49 | 268.94 | 2.49 | 1000 |
| 17 | 31.25 | 0.00 | 0.00 | 0.80 | 0.05 | 31.18 | 0.09 | 850.20 | 687.14 | 9.66 | 1000 |
| 18 | 3.67 | 0.81 | 0.78 | 1.33 | 0.60 | 2.46 | 2.17 | 36.84 | 38.76 | 0.72 | 1000 |
| 19 | 1.51 | 23.06 | 6.53 | 24.52 | 0.78 | 55.49 | 2.79 | 15.28 | 15.25 | 1.27 | 1000 |
| 20 | 0.60 | 22.23 | 24.28 | 3.28 | 0.00 | 5.24 | 4.52 | 2.47 | 2.01 | 16.35 | 1000 |
| 21 | 4.63 | 16.19 | 6.02 | 31.41 | 1.59 | 9.11 | 6.57 | 23.20 | 19.96 | 6.05 | 1000 |
| 22 | 2.84 | 5.67 | 10.02 | 0.96 | 0.82 | 1158.58 | 32.49 | 723.69 | 401.10 | 7.89 | 1000 |
| 23 | 1.30 | 2.62 | 2.50 | 3.42 | 1.17 | 1693.61 | 121.69 | 1575.90 | 1069.37 | 36.08 | 1000 |
| 24 | 1.97 | 19.05 | 32.50 | 3.55 | 1.19 | 607.88 | 200.94 | 1270.75 | 773.59 | 28.27 | 1000 |
| 25 | 2.24 | 21.68 | 25.22 | 0.37 | 0.82 | 10.46 | 2.29 | 4.47 | 4.50 | 1.17 | 1000 |
| 26 | 4.24 | 25.37 | 17.10 | 1.57 | 0.94 | 197.19 | 24.30 | 375.50 | 215.12 | 8.46 | 1000 |
| 27 | 3.07 | 25.14 | 104.71 | 3.32 | 1.40 | 1069.29 | 132.06 | 1818.89 | 872.26 | 54.40 | 1000 |
| 28 | 1.50 | 31.42 | 0.37 | 1.68 | 0.35 | 73.46 | 1.46 | 1.80 | 0.00 | 7.32 | 1000 |
| 29 | 2.15 | 12.81 | 25.26 | 1.51 | 0.94 | 77.93 | 5.88 | 1.67 | 0.58 | 17.53 | 1000 |
| 30 | 3.24 | 4.09 | 61.58 | 3.71 | 1.88 | 1486.40 | 135.25 | 1382.47 | 891.30 | 18.69 | 1000 |

TABLE 13-2

Standardized intensities of cases

| Sample number | Gene name and standardized intensity (×1000) | | | | | | | | | | |
|---|---|---|---|---|---|---|---|---|---|---|---|
| | CEA | TFF1 | TFF2 | FABP1 | CK20 | Muc2 | PRSS4 | GW112 | MASPIN | TACSTD1 | ACTB |
| 31 | 9.85 | 1.64 | 1.81 | 2.23 | 1.43 | 14.72 | 5.37 | 53.61 | 17.10 | 5.73 | 1000 |
| 32 | 6.50 | 13.54 | 22.69 | 2.54 | 2.06 | 117.39 | 13.31 | 99.07 | 35.85 | 6.80 | 1000 |
| 33 | 5.37 | 7.46 | 9.30 | 1.91 | 1.51 | 248.96 | 19.74 | 66.10 | 36.93 | 4.45 | 1000 |
| 34 | 4.86 | 15.98 | 40.42 | 2.68 | 1.76 | 426.83 | 52.10 | 722.85 | 303.39 | 7.41 | 1000 |
| 35 | 1.41 | 24.45 | 0.61 | 0.86 | 0.79 | 3.27 | 1.57 | 2.17 | 1.42 | 6.11 | 1000 |
| 36 | 0.26 | 66.58 | 14.13 | 0.00 | 0.97 | 23.66 | 2.97 | 19.09 | 21.06 | 0.00 | 1000 |
| 37 | 2.65 | 27.17 | 1.81 | 1.45 | 1.04 | 29.28 | 1.36 | 4.79 | 3.83 | 3.75 | 1000 |
| 38 | 7.39 | 0.57 | 0.73 | 1.70 | 0.62 | 29.91 | 2.80 | 80.59 | 94.01 | 6.25 | 1000 |
| 39 | 4.54 | 4.74 | 11.50 | 1.13 | 0.02 | 800.80 | 9.47 | 120.93 | 88.21 | 8.85 | 1000 |
| 40 | 3.42 | 157.63 | 64.28 | 1136.28 | 14.41 | 11.16 | 37.69 | 155.51 | 12.60 | 61.62 | 1000 |
| 41 | 9.02 | 0.41 | 0.40 | 0.48 | 0.29 | 0.60 | 0.43 | 35.56 | 36.85 | 42.20 | 1000 |
| 42 | 11.97 | 90.01 | 26.06 | 1.14 | 0.68 | 1.52 | 3.10 | 18.82 | 25.58 | 54.78 | 1000 |
| 43 | 3.02 | 748.38 | 747.55 | 1577.73 | 30.49 | 1190.83 | 211.88 | 41.61 | 5.30 | 217.93 | 1000 |
| 44 | 2.59 | 416.53 | 887.50 | 946.54 | 42.32 | 6.75 | 70.30 | 15.98 | 5.99 | 27.57 | 1000 |
| 45 | 11.03 | 61.41 | 38.08 | 13.02 | 0.71 | 1.37 | 3.83 | 11.45 | 14.57 | 7.04 | 1000 |

TABLE 13-2-continued

Standardized intensities of cases

Gene name and standardized intensity (×1000)

| Sample number | CEA | TFF1 | TFF2 | FABP1 | CK20 | Muc2 | PRSS4 | GW112 | MASPIN | TACSTD1 | ACTB |
|---|---|---|---|---|---|---|---|---|---|---|---|
| 46 | 7.39 | 46.37 | 10.27 | 36.65 | 77.48 | 1.64 | 7.14 | 3.03 | 3.11 | 21.79 | 1000 |
| 47 | 3.20 | 1124.34 | 370.77 | 24.47 | 24.74 | 1332.84 | 594.53 | 14.59 | 26.39 | 324.43 | 1000 |
| 48 | 4.22 | 331.53 | 276.49 | 86.08 | 1.00 | 30.91 | 4.81 | 40.60 | 31.11 | 20.92 | 1000 |
| 49 | 1.98 | 350.74 | 32.30 | 0.94 | 2.72 | 53.51 | 88.34 | 64.04 | 1.84 | 204.40 | 1000 |
| 50 | 15.84 | 334.96 | 146.95 | 35.26 | 0.79 | 5.93 | 20.37 | 15.78 | 11.19 | 31.01 | 1000 |
| 51 | 57.55 | 195.22 | 116.33 | 20.14 | 1.24 | 6.61 | 1.74 | 21.49 | 22.75 | 4.05 | 1000 |
| 52 | 2.79 | 405.29 | 139.32 | 200.97 | 20.47 | 48.00 | 263.76 | 194.83 | 3.47 | 226.94 | 1000 |
| 53 | 3.66 | 13.61 | 0.55 | 14.49 | 57.67 | 69.37 | 12.22 | 3.06 | 2.54 | 33.42 | 1000 |
| 54 | 8.82 | 85.99 | 31.05 | 163.36 | 8.77 | 127.80 | 2.74 | 2.94 | 2.15 | 22.77 | 1000 |
| 55 | 10.12 | 14.72 | 57.66 | 498.82 | 109.31 | 17.37 | 6.38 | 11.86 | 8.50 | 51.59 | 1000 |
| 56 | 6.94 | 66.18 | 125.88 | 39.54 | 2.65 | 3.59 | 3.97 | 321.54 | 188.68 | 3.59 | 1000 |
| 57 | 1.40 | 0.38 | 13.30 | 0.58 | 0.39 | 2.71 | 0.65 | 45.26 | 58.23 | 1.71 | 1000 |
| 58 | 1.12 | 0.38 | 0.49 | 0.64 | 0.62 | 4.34 | 1.19 | 41.51 | 45.60 | 6.35 | 1000 |
| 59 | 2.30 | 24.67 | 7.43 | 336.42 | 231.99 | 7.34 | 10.13 | 84.33 | 111.65 | 38.15 | 1000 |
| 60 | 3.36 | 0.00 | 0.16 | 11.46 | 0.87 | 11.17 | 1.61 | 287.15 | 235.76 | 1.27 | 1000 |

TABLE 13-4

Standardized intensities of cases

Gene name and standardized intensity (×1000)

| Sample number | CEA | TFF1 | TFF2 | FABP1 | CK20 | Muc2 | PRSS4 | GW112 | MASPIN | TACSTD1 | ACTB |
|---|---|---|---|---|---|---|---|---|---|---|---|
| 91 | 2.28 | 5.80 | 2.52 | 2.51 | 2.05 | 4.96 | 2.33 | 10.46 | 12.30 | 4.16 | 1000 |
| 92 | 18.76 | 0.89 | 2.54 | 11.34 | 0.72 | 1.12 | 6.81 | 33.44 | 22.76 | 12.27 | 1000 |
| 93 | 4.10 | 1.07 | 0.80 | 0.95 | 0.84 | 1.52 | 1.26 | 23.15 | 19.24 | 1.19 | 1000 |
| 94 | 3.46 | 0.84 | 0.86 | 2.05 | 0.89 | 1.48 | 6.21 | 61.42 | 86.44 | 3.49 | 1000 |
| 95 | 21.55 | 85.57 | 48.24 | 1.75 | 1.70 | 2.69 | 12.02 | 1035.21 | 666.07 | 9.98 | 1000 |
| 96 | 2.46 | 0.52 | 28.69 | 1.73 | 0.22 | 130.14 | 149.32 | 1841.09 | 1273.48 | 7.49 | 1000 |
| 97 | 18.43 | 95.98 | 1.00 | 5.29 | 1.78 | 1.26 | 0.95 | 7.08 | 4.44 | 3.34 | 1000 |
| 98 | 5.49 | 0.34 | 0.36 | 0.73 | 0.10 | 0.59 | 0.30 | 0.74 | 0.55 | 0.44 | 1000 |
| 99 | 2.00 | 0.44 | 0.64 | 0.50 | 0.45 | 1.41 | 1.03 | 6.03 | 6.55 | 0.67 | 1000 |
| 100 | 1.91 | 4.64 | 12.14 | 0.54 | 0.52 | 1.27 | 0.94 | 17.81 | 9.74 | 2.65 | 1000 |
| 101 | 1.01 | 0.00 | 0.00 | 0.21 | 0.00 | 0.35 | 0.45 | 1.53 | 0.40 | 3.07 | 1000 |
| 102 | 2.11 | 0.00 | 4.89 | 0.38 | 0.04 | 0.98 | 0.00 | 20.22 | 20.07 | 4.78 | 1000 |
| 103 | 0.00 | 0.00 | 0.00 | 0.00 | 0.00 | 0.00 | 0.00 | 2.57 | 1.63 | 1.62 | 1000 |
| 104 | 5.78 | 3.87 | 0.54 | 0.49 | 0.52 | 0.36 | 0.23 | 4.16 | 4.15 | 0.24 | 1000 |
| 105 | 15.98 | 7.08 | 1.41 | 1.91 | 1.11 | 12.06 | 3.28 | 271.13 | 277.12 | 5.51 | 1000 |
| 106 | 2.73 | 7.91 | 1.58 | 1.51 | 0.44 | 1.33 | 0.91 | 22.45 | 17.68 | 0.80 | 1000 |
| 107 | 13.56 | 2.62 | 3.27 | 3.50 | 2.19 | 3.70 | 3.40 | 31.35 | 36.07 | 3.00 | 1000 |
| 108 | 1.30 | 16.98 | 49.91 | 7.59 | 0.00 | 0.00 | 0.98 | 3.69 | 4.48 | 3.46 | 1000 |
| 109 | 4.33 | 23.83 | 2.10 | 3.51 | 1.45 | 28.59 | 7.33 | 132.44 | 175.70 | 5.65 | 1000 |
| 110 | 2.79 | 14.60 | 32.77 | 13.28 | 0.73 | 5.65 | 1.48 | 40.31 | 55.79 | 1.47 | 1000 |
| 111 | 0.00 | 20.78 | 34.67 | 16.23 | 0.00 | 0.00 | 0.00 | 120.81 | 145.37 | 0.00 | 1000 |
| 112 | 2.64 | 22.08 | 64.11 | 19.09 | 0.42 | 1.11 | 2.30 | 231.82 | 170.05 | 1.21 | 1000 |
| 113 | 1.49 | 194.20 | 58.56 | 102.86 | 8.23 | 181.94 | 241.93 | 1.63 | 10.66 | 171.69 | 1000 |
| 114 | 6.23 | 141.26 | 128.71 | 15.93 | 484.83 | 110.35 | 239.92 | 2.37 | 3.97 | 162.83 | 1000 |
| 115 | 10.56 | 100.29 | 90.95 | 20.93 | 2.14 | 819.09 | 26.15 | 152.13 | 108.66 | 33.12 | 1000 |
| 116 | 1.94 | 266.27 | 281.42 | 1044.14 | 143.54 | 250.67 | 245.99 | 11.50 | 13.94 | 163.94 | 1000 |
| 117 | 3.92 | 578.59 | 480.24 | 453.14 | 12.05 | 1041.50 | 99.89 | 105.73 | 95.47 | 109.22 | 1000 |
| 118 | 8.81 | 291.80 | 221.19 | 43.05 | 2.52 | 25.76 | 43.24 | 25.57 | 29.64 | 50.30 | 1000 |

(4) Setting the Threshold from the Data of the Cases of Early Gastric Cancer

The threshold was set based on 39 cases of the Stage Ia at the last stage diagnosis among the 118 cases from which the intensities were obtained. The threshold was defined as "the maximum intensity that is possible for the case of early gastric cancer to demonstrate". When the intensity over the threshold is obtained, it is judged that "a significant expression" is found, or that is, the expression beyond the case of early gastric cancer is recognized. Therefore, it would be possible to measure many cases of early gastric cancer and to choose the maximum intensity as the threshold. However, it is necessary to include a certain level of scattering from the statistical point of view, and setting of a particular threshold was based on the calculation using the following formulas. Further, in the present Example, two methods were used for calculating the threshold.

Threshold (1)=Maximum standardized intensity of cases of early gastric cancer (Stage *Ia*)+Standard deviation of the same Threshold (2)=Mean standardized intensity of cases of early gastric cancer (Stage *Ia*)+Standard deviation of the same×2

Calculated thresholds are shown in Table 14 below.

TABLE 14

Calculated thresholds

Gene name and Threshold (×1000)

|  | CEA | TFF1 | TFF2 | FABP1 | CK20 | Muc2 | PRSS4 | GW112 | MASPIN | TACSTD1 |
|---|---|---|---|---|---|---|---|---|---|---|
| Threshold (1) | 37.17 | 80.01 | 124.90 | 37.83 | 17.15 | 2124.04 | 246.61 | 2302.11 | 1358.31 | 65.05 |
| Threshold (2) | 16.22 | 37.36 | 52.37 | 16.30 | 5.77 | 1080.41 | 112.40 | 1225.95 | 739.20 | 29.42 |

(5) Judging Presence of Gastric Cancer Cells Using Threshold

Using the two thresholds described above, the presence of gastric cancer cells (prediction of recurrence) in all the 118 cases including early gastric cancer was judged. The judgment was carried out by the following two methods.

Judgment Method A:

Standardized intensity of each case (each gene) is compared with the threshold (1) and the number of genes, in which the standardized intensity is above the threshold, is counted. If 2 genes or more out of all the 10 genes are above the threshold, then this is the information (index) suggesting a high possibility of detecting cancer cells which indicate the possibility of recurrence, that is, a high possibility of recurrence.

Judgment Method B:

Standardized intensity of 6 genes (TFF1, TFF2, FABP1, CK20, MASPIN and TACSTD1), which correlate well with the threshold, are compared with the threshold (2), and the number of genes, in which the standardized intensity is above the threshold, is counted. If 2 genes or more out of the 6 genes are above the threshold, then this is the information (index) suggesting a high possibility of detecting cancer cells which indicate the possibility of recurrence, that is, a high possibility of recurrence.

(6) Result of the judgment (includes the number of genes counted) for all the 118 cases and clinical data for each case are shown in Table 15.

TABLE 15

Judgment by two judgment methods

| Sample number | Judgment method A | | Judgment method B | | Clinical information |
|---|---|---|---|---|---|
| | Number of genes | Judgment | Number of genes | Judgment | |
| 1 | 0 | No recurrence | 0 | No recurrence | Stage 1a |
| 2 | 0 | No recurrence | 0 | No recurrence | Stage 1a |
| 3 | 0 | No recurrence | 0 | No recurrence | Stage 1a |
| 4 | 0 | No recurrence | 0 | No recurrence | Stage 1a |
| 5 | 0 | No recurrence | 0 | No recurrence | Stage 1a |
| 6 | 0 | No recurrence | 0 | No recurrence | Stage 1a |
| 7 | 0 | No recurrence | 0 | No recurrence | Stage 1a |
| 8 | 0 | No recurrence | 0 | No recurrence | Stage 1a |
| 9 | 0 | No recurrence | 0 | No recurrence | Stage 1a |
| 10 | 0 | No recurrence | 0 | No recurrence | Stage 1a |
| 11 | 0 | No recurrence | 0 | No recurrence | Stage 1a |
| 12 | 0 | No recurrence | 0 | No recurrence | Stage 1a |
| 13 | 0 | No recurrence | 0 | No recurrence | Stage 1a |
| 14 | 0 | No recurrence | 1 | No recurrence | Stage 1a |
| 15 | 0 | No recurrence | 0 | No recurrence | Stage 1a |
| 16 | 0 | No recurrence | 0 | No recurrence | Stage 1a |
| 17 | 0 | No recurrence | 0 | No recurrence | Stage 1a |
| 18 | 0 | No recurrence | 0 | No recurrence | Stage 1a |
| 19 | 0 | No recurrence | 1 | No recurrence | Stage 1a |
| 20 | 0 | No recurrence | 0 | No recurrence | Stage 1a |
| 21 | 0 | No recurrence | 1 | No recurrence | Stage 1a |
| 22 | 0 | No recurrence | 0 | No recurrence | Stage 1a |
| 23 | 0 | No recurrence | 2 | Recurrence | Stage 1a |
| 24 | 0 | No recurrence | 1 | No recurrence | Stage 1a |
| 25 | 0 | No recurrence | 0 | No recurrence | Stage 1a |
| 26 | 0 | No recurrence | 0 | No recurrence | Stage 1a |
| 27 | 0 | No recurrence | 3 | Recurrence | Stage 1a |
| 28 | 0 | No recurrence | 0 | No recurrence | Stage 1a |
| 29 | 0 | No recurrence | 0 | No recurrence | Stage 1a |
| 30 | 0 | No recurrence | 2 | Recurrence | Stage 1a |
| 31 | 0 | No recurrence | 0 | No recurrence | Stage 1a |
| 32 | 0 | No recurrence | 0 | No recurrence | Stage 1a |
| 33 | 0 | No recurrence | 0 | No recurrence | Stage 1a |
| 34 | 0 | No recurrence | 0 | No recurrence | Stage 1a |
| 35 | 0 | No recurrence | 0 | No recurrence | Stage 1a |
| 36 | 0 | No recurrence | 1 | No recurrence | Stage 1a |
| 37 | 0 | No recurrence | 0 | No recurrence | Stage 1a |
| 38 | 0 | No recurrence | 0 | No recurrence | Stage 1a |

TABLE 15-continued

Judgment by two judgment methods

| Sample number | Judgment method A Number of genes | Judgment method A Judgment | Judgment method B Number of genes | Judgment method B Judgment | Clinical information |
|---|---|---|---|---|---|
| 39 | 0 | No recurrence | 0 | No recurrence | Stage 1a |
| 40 | 2 | Recurrence | 5 | Recurrence | Cytology positive |
| 41 | 0 | No recurrence | 1 | No recurrence | Cytology positive |
| 42 | 1 | No recurrence | 2 | Recurrence | Cytology positive |
| 43 | 5 | Recurrence | 5 | Recurrence | Cytology positive |
| 44 | 4 | Recurrence | 4 | Recurrence | Cytology positive |
| 45 | 0 | No recurrence | 1 | No recurrence | Cytology positive |
| 46 | 1 | No recurrence | 3 | Recurrence | Cytology positive |
| 47 | 5 | Recurrence | 5 | Recurrence | Cytology positive |
| 48 | 3 | Recurrence | 3 | Recurrence | Cytology positive |
| 49 | 2 | Recurrence | 2 | Recurrence | Cytology positive |
| 50 | 2 | Recurrence | 4 | Recurrence | Cytology positive |
| 51 | 2 | Recurrence | 3 | Recurrence | Cytology positive |
| 52 | 6 | Recurrence | 5 | Recurrence | Cytology positive |
| 53 | 1 | No recurrence | 2 | Recurrence | Cytology positive |
| 54 | 2 | Recurrence | 3 | Recurrence | Cytology positive |
| 55 | 2 | Recurrence | 4 | Recurrence | Cytology positive |
| 56 | 2 | Recurrence | 3 | Recurrence | Cytology positive |
| 57 | 0 | No recurrence | 0 | No recurrence | Extraperitoneal recurrence |
| 58 | 0 | No recurrence | 0 | No recurrence | Extraperitoneal recurrence |
| 59 | 2 | Recurrence | 3 | Recurrence | Extraperitoneal Recurrence |
| 60 | 0 | No recurrence | 0 | No recurrence | Extraperitoneal recurrence |
| 61 | 2 | Recurrence | 1 | No recurrence | Extraperitoneal recurrence |
| 62 | 0 | No recurrence | 0 | No recurrence | Extraperitoneal recurrence |
| 63 | 0 | No recurrence | 0 | No recurrence | Extraperitoneal recurrence |
| 64 | 3 | Recurrence | 5 | Recurrence | Extraperitoneal recurrence |
| 65 | 0 | No recurrence | 0 | No recurrence | Extraperitoneal recurrence |
| 66 | 0 | No recurrence | 0 | No recurrence | Extraperitoneal recurrence |
| 67 | 0 | No recurrence | 0 | No recurrence | Extraperitoneal recurrence |
| 68 | 2 | Recurrence | 1 | No recurrence | Extraperitoneal recurrence |
| 69 | 0 | No recurrence | 0 | No recurrence | Extraperitoneal recurrence |
| 70 | 0 | No recurrence | 1 | No recurrence | Extraperitoneal recurrence |
| 71 | 0 | No recurrence | 1 | No recurrence | Extraperitoneal recurrence |
| 72 | 3 | Recurrence | 3 | Recurrence | Peritoneal recurrence |
| 73 | 0 | No recurrence | 0 | No recurrence | Peritoneal recurrence |
| 74 | 0 | No recurrence | 0 | No recurrence | Peritoneal recurrence |
| 75 | 1 | No recurrence | 0 | No recurrence | Peritoneal recurrence |
| 76 | 2 | Recurrence | 3 | Recurrence | Peritoneal recurrence |
| 77 | 0 | No recurrence | 0 | No recurrence | Peritoneal recurrence |
| 78 | 0 | No recurrence | 1 | No recurrence | Peritoneal recurrence |
| 79 | 0 | No recurrence | 0 | No recurrence | Peritoneal recurrence |
| 80 | 2 | Recurrence | 3 | Recurrence | Peritoneal recurrence |
| 81 | 0 | No recurrence | 0 | No recurrence | Recurrence |
| 82 | 0 | No recurrence | 0 | No recurrence | Recurrence |
| 83 | 0 | No recurrence | 0 | No recurrence | Recurrence |
| 84 | 0 | No recurrence | 0 | No recurrence | Recurrence |
| 85 | 0 | No recurrence | 0 | No recurrence | Recurrence |
| 86 | 0 | No recurrence | 0 | No recurrence | Recurrence |
| 87 | 0 | No recurrence | 0 | No recurrence | Recurrence |
| 88 | 0 | No recurrence | 1 | No recurrence | Recurrence |
| 89 | 0 | No recurrence | 0 | No recurrence | Recurrence |
| 90 | 0 | No recurrence | 0 | No recurrence | Recurrence |
| 91 | 0 | No recurrence | 0 | No recurrence | Recurrence |
| 92 | 0 | No recurrence | 0 | No recurrence | Recurrence |
| 93 | 0 | No recurrence | 0 | No recurrence | Recurrence |
| 94 | 0 | No recurrence | 0 | No recurrence | Recurrence |
| 95 | 1 | No recurrence | 1 | No recurrence | Recurrence |
| 96 | 0 | No recurrence | 1 | No recurrence | Recurrence |
| 97 | 1 | No recurrence | 1 | No recurrence | Recurrence |
| 98 | 0 | No recurrence | 0 | No recurrence | Recurrence |
| 99 | 0 | No recurrence | 0 | No recurrence | Recurrence |
| 100 | 0 | No recurrence | 0 | No recurrence | Recurrence |
| 101 | 0 | No recurrence | 0 | No recurrence | Recurrence |
| 102 | 0 | No recurrence | 0 | No recurrence | Recurrence |
| 103 | 0 | No recurrence | 0 | No recurrence | Recurrence |
| 104 | 0 | No recurrence | 0 | No recurrence | Recurrence |
| 105 | 0 | No recurrence | 0 | No recurrence | Recurrence |
| 106 | 0 | No recurrence | 0 | No recurrence | Recurrence |
| 107 | 0 | No recurrence | 0 | No recurrence | Recurrence |
| 108 | 0 | No recurrence | 0 | No recurrence | Recurrence |
| 109 | 0 | No recurrence | 0 | No recurrence | Recurrence |
| 110 | 0 | No recurrence | 0 | No recurrence | Recurrence |

TABLE 15-continued

Judgment by two judgment methods

| Sample number | Judgment method A | | Judgment method B | | Clinical information |
|---|---|---|---|---|---|
| | Number of genes | Judgment | Number of genes | Judgment | |
| 111 | 0 | No recurrence | 0 | No recurrence | Recurrence |
| 112 | 0 | No recurrence | 2 | Recurrence | Recurrence |
| 113 | 3 | Recurrence | 5 | Recurrence | Immunostaining positive |
| 114 | 4 | Recurrence | 4 | Recurrence | Immunostaining positive |
| 115 | 1 | No recurrence | 4 | Recurrence | Immunostaining positive |
| 116 | 5 | Recurrence | 5 | Recurrence | Immunostaining positive |
| 117 | 4 | Recurrence | 5 | Recurrence | Immunostaining positive |
| 118 | 3 | Recurrence | 4 | Recurrence | Immunostaining positive |

In regard to the results described above, the two judgment methods are more closely examined.

(1) Judgment by Judgment Method A

It is natural that there is no judgment of recurrence in the cases of early gastric cancer (stage Ia) because of the nature of the formula for the threshold, and also all the 32 cases of no recurrence have been justly given the no recurrence judgment (0%). On the other hand, in the cases of cytology positive, 12 cases out of 17 cases (71%), and in the cases of immunostaining positive, 5 cases out of 6 cases (83%) were given the recurrence judgment, suggesting the present method provides sufficient judgment at the same level as the cytology of the hospital specialized for cancer. Further, in the cases of recurrence (extraperitoneal recurrence and peritoneal recurrence) which were negative by the cytology, the present method predicted the recurrence of 7 out of 34 cases (21%) confirming that the method of the present invention for detecting cancer cells is highly sensitive and excellent.

(2) Judgment by Judgment Method B

Although false positive judgments were given to 3 out of 39 cases (8%) of the early gastric cancer (stage Ia) and 1 out of 32 cases (3%) of no recurrence, the rate of judgment error was very low. In the cases of recurrence, 15 out of 17 cases (88%) of cytology positive, and all the 6 cases of immunostaining positive (100%) were given the judgment of recurrence, indicating this method is at the same level as the cytology of the hospital specialized for cancer as is the judgment method A. Further, in the cases of recurrence (extraperitoneal recurrence and peritoneal recurrence) which were negative by the cytology, the present method predicted the recurrence of 5 out of 34 cases (14%) confirming that the method of the present invention for detecting cancer cells is highly sensitive and excellent.

The results described above demonstrate that the methods of the present invention for detecting cancer cells can detect gastric cancer cells with higher sensitivity than the conventional cytology does. Especially, among the 34 cases of recurrence where the cytology during the operation was negative, the detection method of the present invention gave the judgment of recurrence in 7 or 5 cases. Therefore, it is demonstrated that the detection method of the present invention for cancer cells give very useful information in predicting the recurrence of gastric cancer.

Example 5

(1) Cells in the Peritoneal Wash During Operation of the Patients of Gastric Cancer During the gastric cancer operations performed in the National Cancer Center, peritoneal wash was carried out on the gastric cancer patients by the normal method using 100 ml of physiological saline, and the irrigation solution was recovered. From the recovered irrigation solution, a portion was withdrawn as the specimen for the pathological diagnosis and the like, and the rest, that was surplus material, was used as the sample for the present study. Further, on using the surplus materials for the present study, the information was given to the particular patients and the study was carried out under the agreement with the patients according to the informed-consent guideline. Some of the recovered samples were not used because they were unsuitable with various reasons, and 47 samples (the number of patients) were used.

The recovered samples were placed into centrifuge tubes and centrifuged at 15,000 rpm at an room temperature, and after the supernatant was removed, the precipitated pellets were recovered as intraperitoneal free cells.

The clinical information of each sample, when the present Example was prepared, is shown in Table 22 below, although some cases are not determined yet because the prognosis observation is not long enough (less than 2 years).

TABLE 22

Clinical information of 47 cases

| Sample number | Judgment at operation | Lymph node metastasis | Cytology |
|---|---|---|---|
| 1 | Progressive cancer | Yes | Negative |
| 2 | Progressive cancer | Yes | Negative |
| 3 | Progressive cancer | Yes | Negative |
| 4 | Early cancer | No | Negative |
| 5 | Progressive cancer | Yes | Negative |
| 6 | Early cancer | No | Negative |
| 7 | Early cancer | No | Negative |
| 8 | Early cancer | No | Negative |
| 9 | Early cancer | No | Negative |
| 10 | Early cancer | No | Negative |
| 11 | Early cancer | No | Negative |
| 12 | Progressive cancer | Yes | Positive |
| 13 | Early cancer | No | Negative |
| 14 | Progressive cancer | No | Negative |
| 15 | Early cancer | No | Negative |
| 16 | Early cancer | No | Negative |
| 17 | Progressive cancer | Yes | Negative |
| 18 | Progressive cancer | Yes | Negative |
| 19 | Early cancer | No | Negative |
| 20 | Progressive cancer | Yes | Positive |
| 21 | Early cancer | No | Negative |
| 22 | Progressive cancer | Yes | Positive |
| 23 | Progressive cancer | Yes | Positive |
| 24 | Early cancer | No | Negative |
| 25 | Progressive cancer | Yes | Negative |
| 26 | Progressive cancer | Yes | Negative |
| 27 | Progressive cancer | Yes | Negative |
| 28 | Early cancer | No | Negative |
| 29 | Progressive cancer | Yes | Negative |
| 30 | Early cancer | No | Negative |
| 31 | Progressive cancer | Yes | Positive |
| 32 | Progressive cancer | Yes | Negative |
| 33 | Progressive cancer | Yes | Negative |
| 34 | Progressive cancer | No | Negative |
| 35 | Progressive cancer | No | Negative |
| 36 | Early cancer | No | Negative |
| 37 | Early cancer | No | Negative |
| 38 | Progressive cancer | Yes | Positive |
| 39 | Progressive cancer | No | Negative |
| 40 | Early cancer | Yes | Negative |
| 41 | Progressive cancer | Yes | Negative |

TABLE 22-continued

Clinical information of 47 cases

| Sample number | Judgment at operation | Lymph node metastasis | Cytology |
|---|---|---|---|
| 42 | Early cancer | No | Negative |
| 43 | Early cancer | No | Negative |
| 44 | Progressive cancer | Yes | Negative |
| 45 | Progressive cancer | Yes | Positive |
| 46 | Progressive cancer | Yes | Negative |
| 47 | Early cancer | No | Negative |

(2) Extraction of Total RNA

To the free cells obtained, 600 μl of ISOGEN (Nippon Gene Ltd.) was added. The mixture was homogenized well, kept for 5 min at room temperature, and mixed with 120 μl of chloroform for further homogenization.

The mixture was centrifuged at 15,000 rpm for 10 min, and the aqueous phase of the supernatant was recovered.

To the recovered aqueous phase, 20 μg of glycogen and 400 μl of isopropanol were added, and the mixture was kept at room temperature for 15 min and then centrifuged at 15,000 rpm for 10 min.

The supernatant was carefully removed by suction without disturbing the pellet-like precipitate at the lower part of the centrifuge tube, and 70% ethanol was added to the precipitate and centrifuged at 15,000 rpm for 10 min. The supernatant was carefully removed by suction without disturbing the pellet-like precipitate at the lower part of the tube, and the precipitate was air dried at room temperature to remove ethanol. Recovered total RNA was dissolved completely with 21 μl of ultra-pure water added.

To prevent attachment of total RNA component to the wall of the tube, the entire total RNA was transferred to a new microtube.

One μl of the recovered total RNA was taken to measure absorbance at 260 nm to determine the concentration of total RNA and yield thereof.

(3) Reverse Transcription Reaction

Ten μg of the recovered total RNA was mixed with ultra-pure water to bring up the volume to 10 μl, and 1 μl of random hexamer solution, the concentration of which was 0.5 μg/μl, (Amersham Bioscience Corp.), was added. The mixture was heated at 65° C. for 10 min and cooled on ice for 2 min or more.

Next, the reverse transcription reaction was carried out using a reverse transcriptase SuperScript II RT kit (Invitrogen Ltd.). To the mixture, following solutions, which were included in the kit, were added: 4 μl of reaction buffer, 2 μl of 0.1M DTT, 1 μl of 10 mM dNTP Mix, and 1 μl of ribonuclease inhibitor (Takara Ltd.). The mixture was stirred briefly and incubated at 37° C. for 2 min, and then 1 μl of SuperScriptII RT was added and the reaction was continued at 37° C. for 1 hour.

By this procedure, the crude purified product of the reverse transcription product (single stranded cDNA) of the mRNA was obtained.

(4) Multiplex PCR

Next, the multiplex PCR was carried out using the single stranded cDNA as a template. The target genes for amplification were total 9 genes: CEA, TFF1, TFF2, FABP1, CK20, Muc2, Maspin, TACSTD1 and ACTB. The amplification reaction was carried out by the multiplex PCR method which allowed amplification of the 9 genes altogether.

The sequence of each primer is shown in Table 24. Further, as in Example 4, AccuPrime enzyme manufactured by Invitrogen Ltd. was used and 5-(3-aminoallyl)-dUTP was added to the reaction solution of PCR to label the PCR product. The composition of the reaction solution is shown in Table 23 below.

TABLE 23

Composition of reaction solution

| Component | Composition |
|---|---|
| AccuPrime Taq | 0.5 μl |
| 10x Reaction Buffer | 2.0 μl |
| Template DNA (Single stranded cDNA solution, crude purified product) | 1 μl |
| Forward Primer(F) | 5.0 pmol/each |
| Reverse Primer(R) | 5.0 pmol/each |
| Aminoallyl dUTP | 1.0 nmol |
| Distilled water | Up to 20 μl |
| Total | 20 μl |

TABLE 24

Sequence of primers for 9 genes

| Gene name | Forward primer (5' → 3') | Reverse primer (5' → 3') | Nucleotide length (bp) |
|---|---|---|---|
| TFF1 | CCTTTGGAGCAGAGAGGAGGCAAT (SEQ ID NO: 12) | TCAGAGCAGTCAATCTGTGTTGTGAGC (SEQ ID NO: 13) | 426 |
| TFF2 | ATAACAGGACGAACTGCGGCTTCC (SEQ ID NO: 14) | AGCTGATAAGGCGAAGTTTCTTTCTTGG (SEQ ID NO: 15) | 357 |
| FABP1 | TCATGAAGGCAATCGGTCTG (SEQ ID NO: 16) | CAATGTCACCCAATGTCATGG (SEQ ID NO: 17) | 303 |
| CK20 | ACACGGTGAACTATGGGAGCGATCT (SEQ ID NO: 18) | CTTCCAGAAGGCGGCGGTAAGTAG (SEQ ID NO: 19) | 975 |
| MUC2 | CCGGGGAGTGCTGTAAGAAG (SEQ ID NO: 26) | CTCCTCTTTGCAGCAGGAGC (SEQ ID NO: 46) | 428 |
| CEA | TGCATCTGGAACTTCTCCTGGTCTC (SEQ ID NO: 44) | TCACGATGTTGGCTAGGATGGTCT (SEQ ID NO: 45) | 245 |

TABLE 24-continued

Sequence of primers for 9 genes

| Gene name | Forward primer (5' → 3') | Reverse primer (5' → 3') | Nucleotide length (bp) |
|---|---|---|---|
| TACSTD1 | TGCTGGGGTCAGAAGAACAG (SEQ ID NO: 22) | TTGAGTTCCCTATGCATCTCA (SEQ ID NO: 23) | 576 |
| MASPIN | TCCGGGGTAGTTGGCAGAAATACAG (SEQ ID NO: 32) | TGCATGTCAAGGAAGAGATGGGAGA (SEQ ID NO: 33) | 1003 |
| ACTB | TCATCACCATTGGCAATGAG (SEQ ID NO: 30) | CACTGTGTTGGCGTACAGGT (SEQ ID NO: 31) | 155 |

PCR amplification reaction of the prepared reaction solutions was carried out according to the temperature cycle protocol of Table 25 shown below using a commercially available thermal cycler.

TABLE 25

Temperature conditions of PCR amplification reaction

| Step | Temperature | | Incubation time | Number of repeats |
|---|---|---|---|---|
| 1 | | 94° C. | 2 min. | |
| 2 | 94° C. | (denaturation) | 15 sec. | 25 cycles |
| 3 | 60° C. | (annealing) | 45 sec. | |
| 4 | 72° C. | (extension) | 3 min. | |

The purification was carried out using QIAquick PCR Purification Kit manufactured by Qiagen Inc. Purification procedure was followed according to the manual of the kit and at the last step, elution from the column was carried out with 50 µl of ultrapure water.

Following steps, from the labeling with Cy3 to the preparation of the hybridization solution, were carried out in a similar manner to Example 4.

(5) Preparation of Microarray

In carrying out the present Example, a microarray was newly prepared. From the 11 genes, which had been specified to be the gastric cancer specific, PRSS4 and GW112 were omitted, and microarrays were prepared for detecting these 9 genes. The method for producing the microarray was the same as the one described in Example 3, and the probes described in Table 26 below were spotted to detect the 9 genes.

TABLE 26

Probe sequence designed for the 9 genes

| Gene name | Sequence (5' → 3') |
|---|---|
| TFF1 | TTCGACGACACCGTTCGTGGGGTCCCCTGGTGCTTCTATCCT AATACCATCGAC (SEQ ID NO: 1) |
| TFF2 | TTGAAGTGCCGTGGTGCTTCTTCCCGAACTCTGTGGAAGACT GCCATTACTAAGAGAGGC (SEQ ID NO: 2) |
| FABP1 | CATTCTGCACGATTTCCGACACCCCCTTGATATCCTTCCCCT TCTGGATGAGCTCTTCCG (SEQ ID NO: 3) |
| CK20 | TCTGGAGGCCCAACTGATGCAGATTCGGAGTAACATGGAACG CCAGAACAACGAATACCA (SEQ ID NO: 39) |
| MUC2 | CGGAGGTTTCGTACGCCGGCTGCACCAAGACCGTCCTCATGA ATCATTGCTC (SEQ ID NO: 40) |

TABLE 26-continued

Probe sequence designed for the 9 genes

| Gene name | Sequence (5' → 3') |
|---|---|
| CEA | TGCTATATCAGAGCAACCCCAACCAGCACTCCAATCATGATG CCGACAGTGGCC (SEQ ID NO: 37) |
| TACSTD1 | GCAGGGTCTAAAAGCTGGTGTTATTGCTGTTATTGTGGTTGT GGTGATAGCAGTTGTTGC (SEQ ID NO: 7) |
| MASPIN | GTAATTTGTAAAGTTGGGTGGATAAGCTATCCCTGTTGCCGG TTCATGGATTACTTCTCT (SEQ ID NO: 8) |
| ACTB | CCTGTGGCATCCACGAAACTACCTTCAACTCCATCATGAAGT GTGACGTGGACATCCGCA (SEQ ID NO: 11) |

(6) Hybridization

The Cy3-labeled amplified sample that was synthesized in Example 5 (4) was hybridized with the microarray produced. The hybridization was carried out, as in Example 4, using the entire amplified and purified sample and with a hybridization device.

The composition of the hybridization solution was similar to that used in Example 4, and the hybridization was carried out according to the predetermined procedure. The condition and procedure of the hybridization are shown in Table 27 below.

TABLE 27

Hybridization procedures and conditions

| Operation | Operation procedure and condition |
|---|---|
| Stabilization | 65° C. 3 min (Hybridization solution added after stabilization) |
| Reaction | 92° C. 2 min → 55° C. 4 h |
| Washing | 2 × SSC/0.1% SDS at 55° C. 2 × SSC at 20° C. |
| Rinsing | Surface rinsed with 0.1% SSC |
| Water removal | Spin drying |

The spin dried microarray was scanned as in Example 4 and fluorescence intensity was measured. In the present Example, the background was not subtracted unlike Example 4 but the intensity, as it was, obtained from the image was used for judgment hereinafter. Intensities obtained for each probe are shown in Table 28 below.

TABLE 28

Fluorescent intensities of cases

Gene name and intensity

| No. | CEA | TFF1 | TFF2 | FABP1 | CK20 | Muc2 | MASPIN | ACTB | TACSTD1 |
|---|---|---|---|---|---|---|---|---|---|
| 1 | 215.5 | 45.4 | 46.5 | 45.8 | 44.5 | 49.4 | 130.7 | 6525.7 | 411.8 |
| 2 | 49.2 | 44.9 | 44.8 | 44.8 | 45.3 | 45.4 | 64.0 | 7284.6 | 68.1 |
| 3 | 78.3 | 66.2 | 51.3 | 52.2 | 58.4 | 63.3 | 52.1 | 6401.3 | 406.8 |
| 4 | 47.4 | 41.3 | 41.5 | 42.2 | 41.8 | 42.3 | 57.5 | 6896.3 | 78.8 |
| 5 | 194.0 | 62.4 | 45.2 | 43.3 | 53.9 | 95.9 | 411.9 | 6868.6 | 308.6 |
| 6 | 50.5 | 45.3 | 45.6 | 46.9 | 46.0 | 45.6 | 73.3 | 6734.7 | 80.9 |
| 7 | 48.3 | 44.6 | 45.2 | 44.8 | 44.4 | 44.9 | 91.1 | 7834.7 | 46.4 |
| 8 | 59.2 | 46.3 | 47.4 | 49.8 | 46.1 | 47.1 | 91.2 | 7158.8 | 206.0 |
| 9 | 46.6 | 45.7 | 44.8 | 46.3 | 46.0 | 45.6 | 45.4 | 7155.4 | 45.3 |
| 10 | 47.7 | 45.7 | 45.9 | 44.6 | 45.3 | 45.8 | 82.7 | 8227.8 | 48.2 |
| 11 | 448.0 | 45.5 | 46.2 | 43.8 | 49.2 | 163.7 | 350.3 | 7122.6 | 256.6 |
| 12 | 1406.8 | 2225.3 | 192.9 | 47.4 | 52.1 | 54.5 | 114.8 | 6388.2 | 284.2 |
| 13 | 46.3 | 44.8 | 43.3 | 43.7 | 44.8 | 45.1 | 60.5 | 6609.3 | 85.8 |
| 14 | 258.4 | 45.5 | 45.5 | 44.2 | 45.1 | 45.7 | 55.7 | 6049.5 | 97.8 |
| 15 | 94.0 | 45.5 | 45.0 | 43.8 | 44.9 | 45.1 | 80.9 | 6376.1 | 59.9 |
| 16 | 1464.5 | 48.4 | 50.3 | 44.0 | 45.5 | 72.8 | 970.5 | 6543.8 | 235.9 |
| 17 | 64.8 | 43.2 | 40.6 | 41.2 | 43.9 | 41.3 | 84.0 | 3733.7 | 111.8 |
| 18 | 51.9 | 43.6 | 42.3 | 42.3 | 44.2 | 42.5 | 129.8 | 6867.4 | 77.7 |
| 19 | 101.6 | 45.0 | 44.7 | 44.2 | 45.1 | 44.8 | 278.1 | 7204.7 | 59.4 |
| 20 | 1001.3 | 54.1 | 46.8 | 44.9 | 49.9 | 46.5 | 1347.8 | 8494.3 | 148.2 |
| 21 | 76.6 | 45.0 | 44.9 | 46.0 | 45.9 | 48.4 | 57.0 | 6846.5 | 70.5 |
| 22 | 16606.1 | 2975.6 | 81.6 | 75.2 | 19786.6 | 10192.4 | 1820.5 | 7634.0 | 8867.7 |
| 23 | 3306.9 | 1367.4 | 187.0 | 1252.9 | 149.1 | 46.8 | 145.0 | 7599.5 | 740.6 |
| 24 | 44.8 | 44.8 | 43.2 | 44.5 | 44.9 | 44.2 | 44.8 | 6835.2 | 201.2 |
| 25 | 42.0 | 41.7 | 42.0 | 41.9 | 42.6 | 42.1 | 49.9 | 5110.8 | 63.8 |
| 26 | 43.0 | 40.4 | 40.7 | 40.8 | 41.7 | 40.5 | 41.2 | 5152.4 | 69.9 |
| 27 | 1189.0 | 690.2 | 46.7 | 39.9 | 54.3 | 39.8 | 62.7 | 6619.3 | 668.5 |
| 28 | 73.5 | 42.9 | 43.6 | 43.3 | 44.4 | 42.9 | 44.6 | 6106.1 | 104.7 |
| 29 | 434.1 | 98.1 | 43.1 | 71.2 | 151.6 | 43.1 | 122.9 | 6459.6 | 1449.8 |
| 30 | 84.1 | 49.6 | 43.2 | 41.9 | 44.2 | 42.5 | 42.6 | 5932.1 | 69.1 |
| 31 | 1207.7 | 85.1 | 81.8 | 68.7 | 45.1 | 44.9 | 59.5 | 6845.0 | 49.1 |
| 32 | 55.7 | 42.5 | 42.6 | 42.5 | 43.4 | 42.7 | 42.4 | 8822.2 | 79.8 |
| 33 | 66.5 | 48.0 | 45.0 | 45.2 | 44.4 | 46.0 | 44.1 | 7677.1 | 111.4 |
| 34 | 54.2 | 44.3 | 45.0 | 43.8 | 44.8 | 43.8 | 44.4 | 7064.6 | 105.4 |
| 35 | 48.3 | 44.0 | 43.7 | 44.1 | 44.0 | 43.8 | 49.4 | 7239.5 | 54.1 |
| 36 | 68.0 | 45.6 | 45.8 | 44.8 | 44.6 | 46.8 | 58.5 | 7778.0 | 259.8 |
| 37 | 44.7 | 44.7 | 43.8 | 42.6 | 44.9 | 43.8 | 44.6 | 7996.5 | 68.2 |
| 38 | 1762.0 | 667.0 | 78.1 | 603.2 | 87.0 | 49.7 | 578.1 | 6864.9 | 4606.5 |
| 39 | 47.7 | 45.9 | 47.8 | 47.1 | 46.2 | 46.9 | 45.5 | 7555.5 | 123.5 |
| 40 | 45.9 | 46.1 | 46.2 | 46.0 | 45.3 | 47.3 | 44.3 | 7968.3 | 86.1 |
| 41 | 407.2 | 46.7 | 47.2 | 45.3 | 51.2 | 134.2 | 275.0 | 7224.3 | 146.5 |
| 42 | 74.8 | 46.4 | 45.6 | 46.0 | 46.6 | 48.6 | 114.2 | 8021.4 | 129.7 |
| 43 | 70.1 | 47.5 | 46.5 | 46.6 | 47.4 | 51.8 | 179.5 | 8035.2 | 70.9 |
| 44 | 49.5 | 50.1 | 48.3 | 49.2 | 49.9 | 49.6 | 48.3 | 8174.3 | 72.9 |
| 45 | 11596.0 | 245.3 | 55.0 | 184.4 | 74.6 | 1455.3 | 146.5 | 8374.5 | 2225.3 |
| 46 | 51.0 | 49.5 | 47.5 | 48.3 | 50.7 | 49.7 | 49.1 | 7738.4 | 99.0 |
| 47 | 50.3 | 49.1 | 48.3 | 49.7 | 50.8 | 48.6 | 48.7 | 7763.6 | 57.8 |

(7) Judgment Method I

Threshold and judgment method were determined based on the data obtained as in Example 4.

In the present Example the threshold for each gene was determined based on "the 20 cases of early gastric cancer without lymph node metastasis". In the present Example, standardization with ACTB was not done and the intensities obtained from the probe of the 8 genes excluding ACTB were used directly for setting the thresholds and the like.

The thresholds were set based on the intensities of the 20 cases that were early gastric cancer without lymph node metastasis out of those of the 47 cases involved in this Example. As in Example 4, the threshold was defined as "the maximum intensity that is possible for the case of early gastric cancer to demonstrate". When the intensity over the threshold is obtained, it is judged that "a significant expression" is found, that is, the expression beyond the case of early gastric cancer is recognized. Therefore, it would be possible to measure many cases of early gastric cancer and to choose the maximum intensity as the threshold. However, it is necessary to include a certain level of scattering from the statistical point of view, and setting of a particular threshold was based on the calculation using the following formula.

Threshold=Mean standardized intensity of cases of early gastric cancer+Standard deviation of the same×2

The thresholds in the calculated standardized intensities are shown in Table 29 below.

TABLE 29

Gene names and thresholds
Gene name and threshold

| CEA | TFF1 | TFF2 | FABP1 | CK20 | MUC2 | Maspin | TACSTD1 |
|---|---|---|---|---|---|---|---|
| 321.1 | 1.9 | 2.0 | 2.1 | 1.9 | 26.8 | 211.8 | 74.8 |

Next, using the thresholds described above, the presence of gastric cancer cells was judged (prediction of recurrence) in all of the 47 cases including early gastric cancer. The judgment was performed according to the method described below.

The standardized intensity of each case (each gene) was compared with the threshold, and the number of genes, in which the standardized intensity is above the threshold, is counted. If two genes or more out of the targeted 8 genes are above the threshold, then it is judged that the cancer cells exist, that is, this is the case of "recurrence". If one gene or none is above the threshold, then there is no cancer cell and it judged that this is the case of no recurrence.

The result of judgment (including the number of genes counted) of all of the 47 cases and the clinical data of each case are shown in Table 30.

TABLE 30

| Sample number | Judgment at operation | Lymph node metastasis | Cytology | Number of positive genes | Judgment |
|---|---|---|---|---|---|
| 1 | Progressive cancer | Yes | Negative | 1 | No recurrence |
| 2 | Progressive cancer | Yes | Negative | 0 | No recurrence |
| 3 | Progressive cancer | Yes | Negative | 5 | Recurrence |
| 4 | Early cancer | No | Negative | 0 | No recurrence |
| 5 | Progressive cancer | Yes | Negative | 3 | Recurrence |
| 6 | Early cancer | No | Negative | 0 | No recurrence |
| 7 | Early cancer | No | Negative | 0 | No recurrence |
| 8 | Early cancer | No | Negative | 1 | No recurrence |
| 9 | Early cancer | No | Negative | 0 | No recurrence |
| 10 | Early cancer | No | Negative | 0 | No recurrence |
| 11 | Early cancer | No | Negative | 1 | No recurrence |
| 12 | Progressive cancer | Yes | Positive | 5 | Recurrence |
| 13 | Early cancer | No | Negative | 0 | No recurrence |
| 14 | Progressive cancer | No | Negative | 0 | No recurrence |
| 15 | Early cancer | No | Negative | 0 | No recurrence |
| 16 | Early cancer | No | Negative | 3 | Recurrence |
| 17 | Progressive cancer | Yes | Negative | 0 | No recurrence |
| 18 | Progressive cancer | Yes | Negative | 0 | No recurrence |
| 19 | Early cancer | No | Negative | 0 | No recurrence |
| 20 | Progressive cancer | Yes | Positive | 4 | Recurrence |
| 21 | Early cancer | No | Negative | 0 | No recurrence |
| 22 | Progressive cancer | Yes | Positive | 8 | Recurrence |
| 23 | Progressive cancer | Yes | Positive | 6 | Recurrence |
| 24 | Early cancer | No | Negative | 0 | No recurrence |
| 25 | Progressive cancer | Yes | Negative | 0 | No recurrence |
| 26 | Progressive cancer | Yes | Negative | 0 | No recurrence |
| 27 | Progressive cancer | Yes | Negative | 4 | Recurrence |
| 28 | Early cancer | No | Negative | 0 | No recurrence |
| 29 | Progressive cancer | Yes | Negative | 4 | Recurrence |
| 30 | Early cancer | No | Negative | 1 | No recurrence |
| 31 | Progressive cancer | Yes | Positive | 4 | Recurrence |
| 32 | Progressive cancer | Yes | Negative | 0 | No recurrence |
| 33 | Progressive cancer | Yes | Negative | 0 | No recurrence |
| 34 | Progressive cancer | No | Negative | 0 | No recurrence |
| 35 | Progressive cancer | No | Negative | 0 | No recurrence |
| 36 | Early cancer | No | Negative | 0 | No recurrence |
| 37 | Early cancer | No | Negative | 0 | No recurrence |
| 38 | Progressive cancer | Yes | Positive | 7 | Recurrence |
| 39 | Progressive cancer | No | Negative | 0 | No recurrence |
| 40 | Early cancer | Yes | Negative | 0 | No recurrence |
| 41 | Progressive cancer | Yes | Negative | 2 | Recurrence |
| 42 | Early cancer | No | Negative | 0 | No recurrence |
| 43 | Early cancer | No | Negative | 0 | No recurrence |
| 44 | Progressive cancer | Yes | Negative | 2 | Recurrence |
| 45 | Progressive cancer | Yes | Positive | 7 | Recurrence |
| 46 | Progressive cancer | Yes | Negative | 1 | No recurrence |
| 47 | Early cancer | No | Negative | 2 | Recurrence |

In examining the result of the judgment above, among the 20 cases of early gastric cancer without lymph node metastasis, only two cases were judged to be "recurrence" (cancer cells are present) and other 18 cases were judged to be "no recurrence". In general, there are statistical data that even in the cases of early gastric cancer without lymph node metastasis, about 10% of the cases will recur in the end, and thus the present judgment of the positive rate of 10% appears to be reasonable.

On the other hand, in the cases with cytology positive, all the seven positive cases were judged to be "recurrence", in complete agreement with the observation of the pathologist. These facts strongly indicate the correctness of the diagnosis by the microarray of the present invention.

While in the cases of progressive cancer with negative cytology, 6 cases out of 19 cases were judged to be "recurrence". These 19 cases were negative in cytology during the operation, that is, the possibility of recurrence was not recognized in these cases. However, there are statistical data suggesting that there will be recurrence in about 30% of these cases, and the result of the present judgment of about 30% positive rate appears to be reasonable. The judgment of recurrence of the present invention is judging the recurrence until two years after the operation. Since the present embodiment was carried out for less than two years, the correctness of the present judgment on these cases can not be determined in a strict sense. However, the statistical data strongly support the judgment method of the present invention and it can be concluded that this judgment method is a promising one.

(8) Judgment Method II

Next, the judgment was determined based on the standard of the absolute luminance of each probe.

Among the luminance data on Table 28, the intensities of the 8 genes excluding ACTB which expressed regardless of the kind of genes were used to "convert the intensity of each gene to a point", and the point of the genes were added up in each case, and the judgment was determined according to the sum of the point. The method of converting each gene to the point is shown in Table 31 below.

TABLE 31

| Gene name | Intensity | | | |
|---|---|---|---|---|
| | 67 or below | 67 to 90 | 90 to 135 | 135 or above |
| TACSTD1 | 0 point | 0 point | 0 point | 4 points |
| Other than TACSTD1 | 0 point | 1 point | 2 points | 4 points |

The points in each case are added up according to the standard described above. When 2 of the genes in a case become positive, that is, the points of the case are 8 points or more, then the judgment given to the case is "recurrence", and the cases with 7 points or less are judged to be "no recurrence".

The clinical information of each case, total points, and the result of the judgment are given in Table 32 below.

TABLE 32

| Sample number | Judgment at operation | Lymph node metastasis | Cytology | Total score | Judgment |
|---|---|---|---|---|---|
| 1 | Progressive cancer | Yes | Negative | 10 | Recurrence |
| 2 | Progressive cancer | Yes | Negative | 0 | No recurrence |
| 3 | Progressive cancer | Yes | Negative | 5 | No recurrence |
| 4 | Early cancer | No | Negative | 0 | No recurrence |
| 5 | Progressive cancer | Yes | Negative | 14 | Recurrence |
| 6 | Early cancer | No | Negative | 1 | No recurrence |
| 7 | Early cancer | No | Negative | 2 | No recurrence |
| 8 | Early cancer | No | Negative | 6 | No recurrence |
| 9 | Early cancer | No | Negative | 0 | No recurrence |
| 10 | Early cancer | No | Negative | 1 | No recurrence |
| 11 | Early cancer | No | Negative | 16 | Recurrence |
| 12 | Progressive cancer | Yes | Positive | 18 | Recurrence |
| 13 | Early cancer | No | Negative | 0 | No recurrence |
| 14 | Progressive cancer | No | Negative | 4 | No recurrence |
| 15 | Early cancer | No | Negative | 3 | No recurrence |
| 16 | Early cancer | No | Negative | 13 | Recurrence |
| 17 | Progressive cancer | Yes | Negative | 1 | No recurrence |
| 18 | Progressive cancer | Yes | Negative | 2 | No recurrence |
| 19 | Early cancer | No | Negative | 6 | No recurrence |
| 20 | Progressive cancer | Yes | Positive | 12 | Recurrence |
| 21 | Early cancer | No | Negative | 1 | No recurrence |
| 22 | Progressive cancer | Yes | Positive | 26 | Recurrence |
| 23 | Progressive cancer | Yes | Positive | 28 | Recurrence |
| 24 | Early cancer | No | Negative | 4 | No recurrence |
| 25 | Progressive cancer | Yes | Negative | 0 | No recurrence |
| 26 | Progressive cancer | Yes | Negative | 0 | No recurrence |
| 27 | Progressive cancer | Yes | Negative | 12 | Recurrence |
| 28 | Early cancer | No | Negative | 1 | No recurrence |
| 29 | Progressive cancer | Yes | Negative | 17 | Recurrence |
| 30 | Early cancer | No | Negative | 1 | No recurrence |
| 31 | Progressive cancer | Yes | Positive | 7 | No recurrence |
| 32 | Progressive cancer | Yes | Negative | 0 | No recurrence |
| 33 | Progressive cancer | Yes | Negative | 0 | No recurrence |
| 34 | Progressive cancer | No | Negative | 0 | No recurrence |
| 35 | Progressive cancer | No | Negative | 0 | No recurrence |
| 36 | Early cancer | No | Negative | 5 | No recurrence |
| 37 | Early cancer | No | Negative | 0 | No recurrence |
| 38 | Progressive cancer | Yes | Positive | 22 | Recurrence |
| 39 | Progressive cancer | No | Negative | 0 | No recurrence |
| 40 | Early cancer | Yes | Negative | 0 | No recurrence |
| 41 | Progressive cancer | Yes | Negative | 14 | Recurrence |
| 42 | Early cancer | No | Negative | 3 | No recurrence |
| 43 | Early cancer | No | Negative | 5 | No recurrence |
| 44 | Progressive cancer | Yes | Negative | 0 | No recurrence |
| 45 | Progressive cancer | Yes | Positive | 25 | Recurrence |
| 46 | Progressive cancer | Yes | Negative | 0 | No recurrence |
| 47 | Early cancer | No | Negative | 0 | No recurrence |

In examining the result of the judgment above, among the 20 cases of early gastric cancer without lymph node metastasis, only two cases were judged to be "recurrence" (cancer cells are present) and other 18 cases were judged to be "no recurrence". In general, there are statistical data that even in the cases of early gastric cancer without lymph node metastasis, about 10% of the cases will recur in the end, and thus the present judgment of the positive rate of 10% appears to be reasonable.

On the other hand, in the cases of positive cytology, 6 cases out of seven positive cases were judged to be "recurrence". Although only one case was different from the observation of the pathologist, the correctness of the diagnosis by the microarray of the present invention was strongly indicated.

While in the cases of progressive cancer with negative cytology, 5 cases out of 19 cases were judged to be "recurrence". These 19 cases were negative in cytology during the operation, that is, the possibility of recurrence was not recognized in these cases. However, there are statistical data suggesting that there will be recurrence in about 30% of these cases, and the result of the present judgment of about 30% positive rate appears to be reasonable. The judgment of recurrence of the present invention is judging the recurrence until two years after the operation. Since the present embodiment was carried out for less than two years, the correctness of the present judgment on these cases can not be determined in a strict sense. However, the statistical data strongly support the judgment method of the present invention and it can be concluded that this judgment method is a promising one.

Example 6

Detection of Individual Genes by Single PCR and by Microarray

PCR amplifications were carried out using cDNA of the gastric cancer cells KATOIII obtained in Example 1 as a template and primers for CEA shown below.

```
Forward primer for CEA:
                                    (SEQ ID NO: 20)
AACTTCTCCTGGTCTCTCAGCT Reverse primer for CEA:
                                    (SEQ ID NO: 21)
GCAAATGCTTTAAGGAAGAAG
```

PCR amplification was carried out according to the conventional method using a kit of ExTaq enzyme provided by Takara Ltd. In the amplification reaction, fluorescent labeling substrate Cy3dUTP manufactured by Amersham Pharmacia Ltd. was used for labeling. The composition of the PCR reaction solution is shown in Table 33 below.

TABLE 33

Composition of reaction solution

| Component | Composition |
|---|---|
| Ex Taq (Takara) (5 U/μl) | 1.0 μl |
| 10× Reaction Buffer | 5.0 μl |
| Template DNA (KATOIII) | 0.5 μl |
| Forward Primer(F) | 100 pmol/each |
| Reverse Primer(R) | 100 pmol/each |
| Cy3dUTP (1 mM) | 1.0 μl |
| Distilled water | Up to 50 μl |
| Total | 50 μl |

PCR amplification reaction of the prepared reaction solutions was carried out according to the temperature cycle protocol of Table 34 shown below using a thermal cycler.

TABLE 34

Temperature conditions of PCR amplification reaction

| Step | Temperature | Incubation time | Number of repeats |
|---|---|---|---|
| 1 | 94° C. | 2 min. | |
| 2 | 94° C. (denaturation) | 15 sec. | 25 cycles |
| 3 | 65° C. (annealing) | 45 sec. | |
| 4 | 72° C. (extension) | 3 min. | |

Entire PCR product obtained, 50 μl, was purified using the DNA purification kit QIAquick manufactured by Qiagen Inc.

Extraction from the kit was carried out using 50 μl of EB buffer included in the kit. The PCR product obtained was analyzed by electrophoresis as in Example 2 (1) and confirmed to be consisted of a single band of a chain length, 145 bp that was described in Table 3.

Twenty μl of the PCR product obtained was hybridized to the microarray. Preparation of the hybridization solution, temperature condition, luminance measurement and the like were carried out as in Example 4 (3). Also the microarray used was the same microarray used in Example 4 (3).

The intensity measured using the probe for CEA detection was 15,740.

The present Example has proven that the PCR product amplified by the primer for CEA, which is disclosed in the present invention, is detected by the probe for CEA detection on the microarray.

Similar test experiments were carried out for all other combinations of primer/probe and it is confirmed that the PCR products, which were amplified by the primers disclosed in the present invention, can be detected by the probes disclosed in the present invention.

Comparative Example 1

Comparison of Sensitivity with that of Electrophoresis

To examine the sensitivity of the probe carrier produced by the present invention, a comparative experiment was carried out between the probe carrier and electrophoresis. In the comparative experiment, the multiplex PCR products obtained in Example 4-(1) were used. A group and B group of the multiplex PCR products were mixed and purified with a purification kit to obtain about 50 μl of purified PCR products, which were used for the present comparative experiment. Electrophoresis was carried out using a bioanalyzer 2100 (name of the kit: DNA12000) manufactured by Agilent Technologies Inc, and 1 μl out of 50 μl of purified PCR products obtained was subjected to electrophoresis according to the manual provided from the manufacturer.

Figure 2:
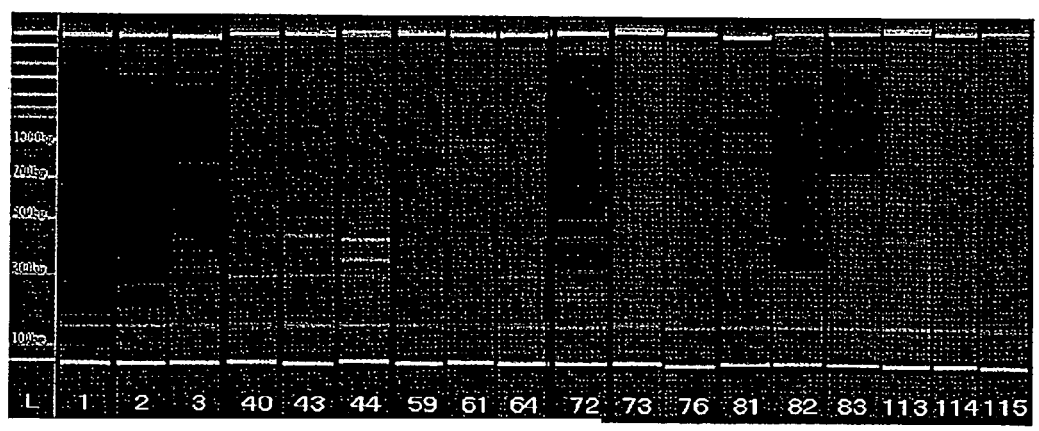
FIG. 2 shows the results of electrophoresis of 18 cases.
Figure 3A:
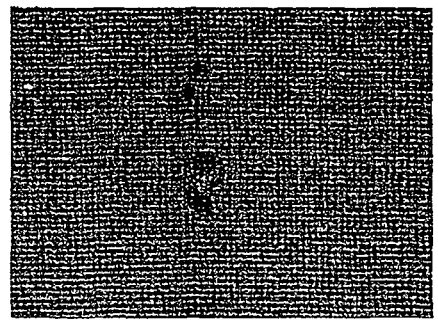
FIGS. 3A, 3B and 3C show the result of electrophoresis of multiplex PCR products.
Figure 3B:
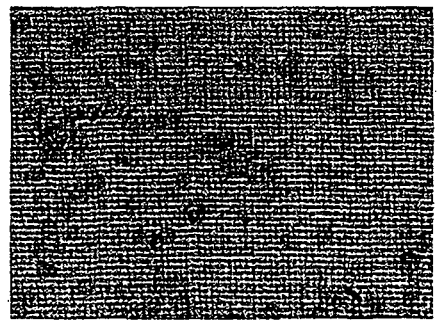
Figure 3C:
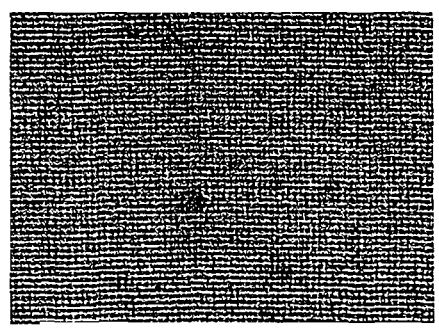
Figure 4A:
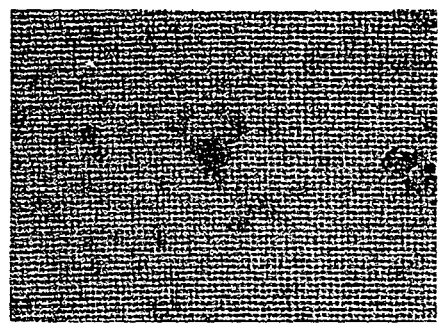
FIGS. 4A, 4B and 4C show the result of electrophoresis of multiplex PCR products.
Figure 4B:
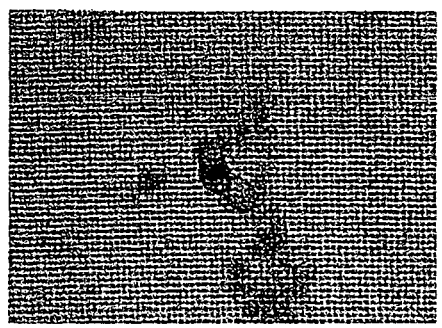
Figure 4C:
Figure 5A:
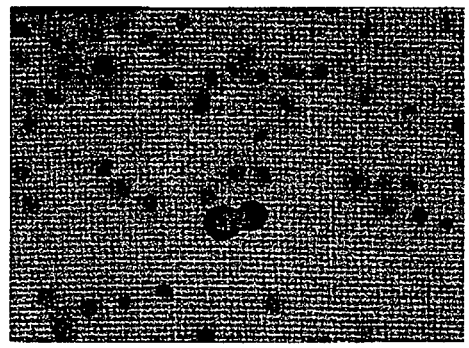
FIGS. 5A, 5B and 5C show the result of electrophoresis of multiplex PCR products.
Figure 5B:
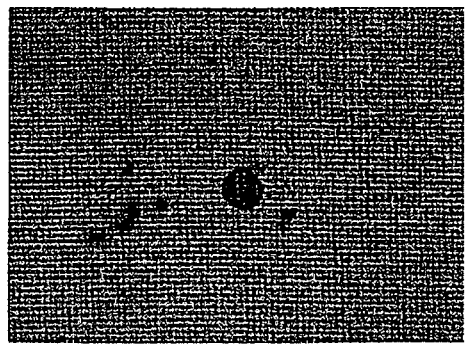
Figure 5C:
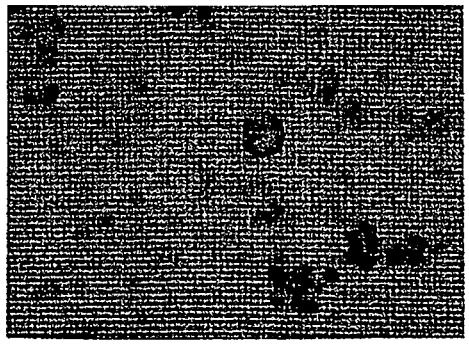
Figure 6A:
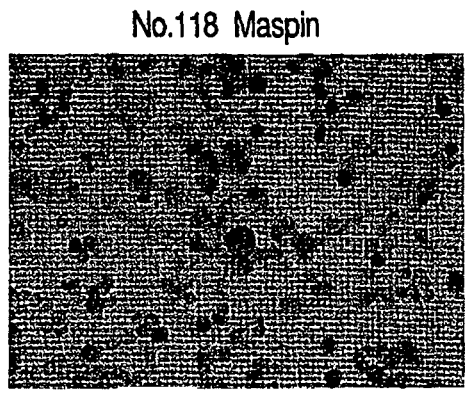
FIGS. 6A, 6B and 6C shows the result of electrophoresis of multiplex PCR products.
Figure 6B:
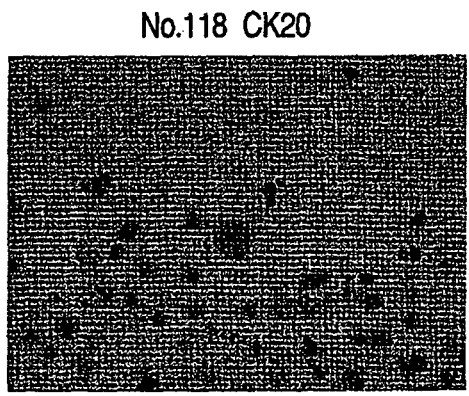
Figure 6C:
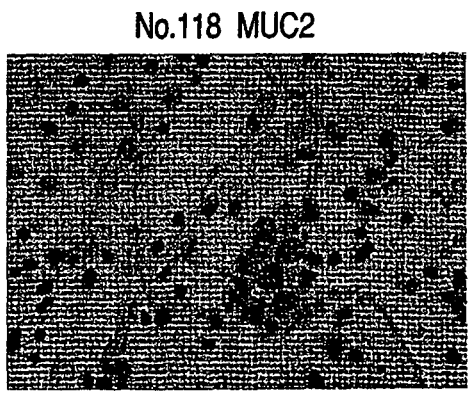
Figure 7:
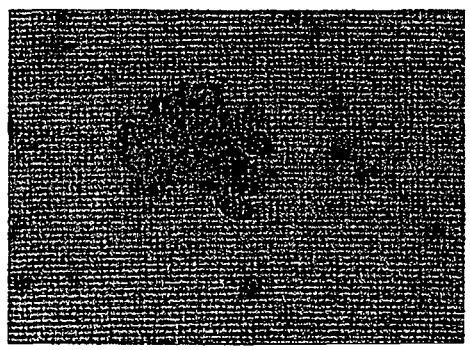
FIG. 7 shows the result of electrophoresis of multiplex PCR products.

The samples subjected to the electrophoresis were 18 samples representing the respective cases among the 118 samples of Example 4. In particular, used are: sample No. 1, 2 and 3 as the case of early gastric cancer (Stage Ia); sample No. 40, 43 and 44 as the positive cases of cytology; sample No. 59, 61 and 64 as the cases of extraperitoneal recurrence; sample No. 72, 73 and 76 as the cases of peritoneal recurrence; Sample No. 81, 82 and 83 as the cases of no recurrence; and sample No. 113, 114, and 115 as the cases of immunostaining positive. Result of the electrophoresis is shown in FIG. 2.

Examination of the result of the electrophoresis revealed a band of ACTB, the house keeping gene, at about 155 bp in all the cases. In the 3 cases (No. 40, 43 and 44) that were positive in cytology, bands derived from PCR products other than ACTB were confirmed suggesting that the detection of these genes is possible by electrophoresis. However, in other cases of recurrence excluding early gastric cancer, bands other than ACTB are hardly recognized. In the microarray analyses using the same sample could detect the presence of the PCR products (expression of these genes) indicating that the detection by the microarray of the present invention is extremely sensitive method.

Comparative Example 2

Detection by Immunostaining

Among the 118 samples which were collected at the National Cancer Center and used in the Examples described above, the 6 samples from No. 113 to No. 118 were subjected to cell observation by immunostaining, and found to be positive as shown in Table 4. The immunostaining was carried out according to the standard method. The representative immunostaining images are shown in FIGS. 3A to 7 below. The numbers in the figures are sample numbers in Table 4, and the genes names are the name of the antibody used for staining. Immunostaining is a highly specific method for detecting cancer cells, and the positive in the immunostaining indicates the cells are cancer cells for sure. Among the 6 positive cases of immunostaining, 5 cases by the judgment method A and all the 6 cases by the judgment method B are also shown strongly to be cancer cells in the expression level of the genes. That is, the detection method of the present invention for cancer cells is as accurate as the immunostaining method, indicating this method has high sensitivity and accuracy. It is also indicated that cancer cells can be detected for sure by detecting the expression of the genes which is the subject of the detection in the present invention.

The present invention is not limited to the above embodiments and various changes and modifications can be made within the spirit and scope of the present invention. Therefore to apprise the public of the scope of the present invention, the following claims are made.

What is claimed is:

1. A kit for conducting at least one of detection and diagnosis of gastric cancer, comprising:
- an array consisting of eleven probes immobilized on a solid support, the eleven probes being used for detecting eleven target genes; and
- a plurality of primer sets for amplifying by PCR a partial region of each of the eleven target genes,
- wherein the eleven target genes consist of:
  - ten genes specific to gastric cancer cells selected from the group consisting of: trefoil factor 1 (TFF1); trefoil factor 2 (TFF2); fatty acid binding protein 1, liver (FABP1); cytokeratins 20 (CK20); mucin 2 (MUC2); carcinoembryonic antigen (CEA); tumor-associated calcium signal transducer 1 (TACSTD1); maspin (MASPIN); protease, serine, 4, (PRSS4); and olfactomedin 4 (GW112); and
  - beta-actin (ACTB) which is a housekeeping gene and with which expression amounts of the other genes are compared, and
- wherein the kit comprises each of the following eleven combinations, each comprising one of the eleven probes and one of the plurality of primer sets:

(Combination for detecting TFF1):
Combination of a probe for detecting TFF1 consisting of a nucleotide sequence of SEQ ID NO: 1 of the sequence listing and a primer set for amplifying TFF1 consisting of nucleotide sequences of SEQ ID NOS: 12 and 13 of the sequence listing, (Combination for detecting TFF2):
Combination of a probe for detecting TFF2 consisting of a nucleotide sequence of SEQ ID NO: 2 of the sequence listing and a primer set for amplifying TFF2 consisting of nucleotide sequences of SEQ ID NOS: 14 and 15 of the sequence listing, (Combination for detecting FABP1):
Combination of a probe for detecting FABP1 consisting of a nucleotide sequence of SEQ ID NO: 3 of the sequence listing and a primer set for amplifying FABP1 consisting of nucleotide sequences of SEQ ID NOS: 16 and 17 of the sequence listing, (Combination for detecting CK20):
Combination of a probe for detecting CK20 consisting of a nucleotide sequence of SEQ ID NO: 4 of the sequence listing and a primer set for amplifying CK20 consisting of nucleotide sequences of SEQ ID NOS: 18 and 19 of the sequence listing, (Combination for detecting MUC2):
Combination of a probe for detecting MUC2 consisting of a nucleotide sequence of SEQ ID NO: 5 of the sequence listing and a primer set for amplifying MUC2 consisting of nucleotide sequences of SEQ ID NOS: 26 and 27 of the sequence listing, (Combination for detecting CEA):
Combination of a probe for detecting CEA consisting of a nucleotide sequence of SEQ ID NO: 6 of the sequence listing and a primer set for amplifying CEA consisting of nucleotide sequences of SEQ ID NOS: 20 and 21 of the sequence listing, (Combination for detecting TACSTD1):
Combination of a probe for detecting TACSTD1 consisting of a nucleotide sequence of SEQ ID NO: 7 of the sequence listing and a primer set for amplifying TACSTD1 consisting of nucleotide sequences of SEQ ID NOS: 22 and 23 of the sequence listing, (Combination for detecting MASPIN):
Combination of a probe for detecting MASPIN consisting of a nucleotide sequence of SEQ ID NO: 8 of the sequence listing and a primer set for amplifying MASPIN consisting of nucleotide sequences of SEQ ID NOS: 32 and 33 of the sequence listing,
(Combination for detecting PRSS4):
Combination of a probe for detecting PRSS4 consisting of a nucleotide sequence of SEQ ID NO: 9 of the sequence listing and a primer set for amplifying PRSS4 consisting of nucleotide sequences of SEQ ID NOS: 28 and 29 of the sequence listing,
(Combination for detecting GW112):
Combination of a probe for detecting GW112 consisting of a nucleotide sequence of SEQ ID NO: 10 of the sequence listing and a primer set for amplifying GW112 consisting of nucleotide sequences of SEQ ID NOS: 24 and 25 of the sequence listing,
(Combination for detecting ACTB):
Combination of a probe for detecting ACTB consisting of a nucleotide sequence of SEQ ID NO: 11 of the sequence listing and a primer set for amplifying ACTB consisting of nucleotide sequences of SEQ ID NOS: 30 and 31.

2. A kit for conducting at least one of detection and diagnosis of gastric cancer, comprising:
an array consisting of nine probes immobilized on a solid support, the nine probes being used for detecting nine target genes; and
a plurality of primer sets for amplifying by PCR a partial region of each of the nine target genes,
wherein the nine target genes consist of:
eight genes specific to gastric cancer cells selected from the group consisting of: trefoil factor 1 (TFF1); trefoil factor 2 (TFF2); fatty acid binding protein 1, liver (FABP1); cytokeratins 20 (CK20); mucin 2 (MUC2); carcinoembryonic antigen (CEA); tumor-associated calcium signal transducer 1 (TACSTD1); and maspin (MASPIN); and
beta-actin (ACTB) which is a housekeeping gene and with which expression amounts of the other genes are compared, and
wherein the kit comprises each of the following nine combinations, each comprising one of the nine probes and one of the plurality of primer sets:
(Combination for detecting TFF1):
Combination of a probe for detecting TFF1 consisting of a nucleotide sequence of SEQ ID NO: 1 of the sequence listing and a primer set for amplifying TFF1 consisting of nucleotide sequences of SEQ ID NOS: 12 and 13 of the sequence listing,
(Combination for detecting TFF2):
Combination of a probe for detecting TFF2 consisting of a nucleotide sequence of SEQ ID NO: 2 of the sequence listing and a primer set for amplifying TFF2 consisting of nucleotide sequences of SEQ ID NOS: 14 and 15 of the sequence listing,
(Combination for detecting FABP1):
Combination of a probe for detecting FABP1 consisting of a nucleotide sequence of SEQ ID NO: 3 of the sequence listing and a primer set for amplifying FABP1 consisting of nucleotide sequences of SEQ ID NOS: 16 and 17 of the sequence listing,
(Combination for detecting CK20):
Combination of a probe for detecting CK20 consisting of a nucleotide sequence of SEQ ID NO: 39 of the sequence listing and a primer set for amplifying CK20 consisting of nucleotide sequences of SEQ ID NOS: 18 and 19 of the sequence listing,
(Combination for detecting MUC2):
Combination of a probe for detecting MUC2 consisting of a nucleotide sequence of SEQ ID NO: 40 of the sequence listing and a primer set for amplifying MUC2 consisting of nucleotide sequences of SEQ ID NOS: 26 and 46 of the sequence listing,
(Combination for detecting CEA):
Combination of a probe for detecting CEA consisting of a nucleotide sequence of SEQ ID NO: 37 of the sequence listing and a primer set for amplifying CEA consisting of nucleotide sequences of SEQ ID NOS: 44 and 45 of the sequence listing,
(Combination for detecting TACSTD1):
Combination of a probe for detecting TACSTD1 consisting of a nucleotide sequence of SEQ ID NO: 7 of the sequence listing and a primer set for amplifying TACSTD1 consisting of nucleotide sequences of SEQ ID NOS: 22 and 23 of the sequence listing,
(Combination for detecting MASPIN):
Combination of a probe for detecting MASPIN consisting of a nucleotide sequence of SEQ ID NO: 8, 41, 42 or 43 of the sequence listing and a primer set for amplifying MASPIN consisting of nucleotide sequences of SEQ ID NOS: 32 and 33 of the sequence listing,
(Combination for detecting ACTB):
Combination of a probe for detecting ACTB consisting of a nucleotide sequence of SEQ ID NO: 11 of the sequence listing and a primer set for amplifying ACTB consisting of nucleotide sequences of SEQ ID NOS: 30 and 31.

3. A gene inspection kit for eleven target genes, the eleven target genes consisting of:
ten genes specific to gastric cancer cells selected from the group consisting of: trefoil factor 1 (TFF1); trefoil factor 2 (TFF2); fatty acid binding protein 1, liver (FABP1); cytokeratins 20 (CK20); mucin 2 (MUC2); carcinoembryonic antigen (CEA); tumor-associated calcium signal transducer 1 (TACSTD1), maspin (MASPIN); protease, serine, 4, (PRSS4); and olfactomedin 4 (GW112); and
beta-actin (ACTB) which is a housekeeping gene and with which expression amounts of the other genes are compared,
wherein the gene inspection kit comprises each of the eleven combinations listed below, each comprising (i) one of eleven probes for inspection of the eleven target genes and (ii) one of a plurality of primer sets for amplifying by PCR a partial region of each of the eleven target genes, and
wherein the gene inspection kit comprises a probe carrier to be used for detecting oligonucleotides which were amplified by PCR by using the plurality of primer sets, the probe carrier consisting of the eleven probes immobilized on a carrier:
(Combination for detecting TFF1):
Combination of a probe for detecting TFF1 consisting of a nucleotide sequence of SEQ ID NO: 1 of the sequence listing and a primer set for amplifying TFF1 consisting of nucleotide sequences of SEQ ID NOS: 12 and 13 of the sequence listing,
(Combination for detecting TFF2):
Combination of a probe for detecting TFF2 consisting of a nucleotide sequence of SEQ ID NO: 2 of the sequence listing and a primer set for amplifying TFF2 consisting of nucleotide sequences of SEQ ID NOS: 14 and 15 of the sequence listing,
(Combination for detecting FABP1):
Combination of a probe for detecting FABP1 consisting of a nucleotide sequence of SEQ ID NO: 3 of the sequence listing and a primer set for amplifying FABP1 consisting of nucleotide sequences of SEQ ID NOS: 16 and 17 of the sequence listing, (Combination for detecting CK20):
Combination of a probe for detecting CK20 consisting of a nucleotide sequence of SEQ ID NO: 4 of the sequence listing and a primer set for amplifying CK20 consisting of nucleotide sequences of SEQ ID NOS: 18 and 19 of the sequence listing,
(Combination for detecting MUC2):
Combination of a probe for detecting MUC2 consisting of a nucleotide sequence of SEQ ID NO: 5 of the sequence listing and a primer set for amplifying MUC2 consisting of nucleotide sequences of SEQ ID NOS: 26 and 27 of the sequence listing,
(Combination for detecting CEA):
Combination of a probe for detecting CEA consisting of a nucleotide sequence of SEQ ID NO: 6 of the sequence listing and a primer set for amplifying CEA consisting of nucleotide sequences of SEQ ID NOS: 20 and 21 of the sequence listing,
(Combination for detecting TACSTD1):
Combination of a probe for detecting TACSTD1 consisting of a nucleotide sequence of SEQ ID NO: 7 of the sequence listing and a primer set for amplifying TACSTD1 consisting of nucleotide sequences of SEQ ID NOS: 22 and 23 of the sequence listing,
(Combination for detecting MASPIN):
Combination of a probe for detecting MASPIN consisting of a nucleotide sequence of SEQ ID NO: 8 of the sequence listing and a primer set for amplifying MASPIN consisting of nucleotide sequences of SEQ ID NOS: 32 and 33 of the sequence listing,
(Combination for detecting PRSS4):
Combination of a probe for detecting PRSS4 consisting of a nucleotide sequence of SEQ ID NO: 9 of the sequence listing and a primer set for amplifying PRSS4 consisting of nucleotide sequences of SEQ ID NOS: 28 and 29 of the sequence listing,
(Combination for detecting GW112):
Combination of a probe for detecting GW112 consisting of a nucleotide sequence of SEQ ID NO: 10 of the sequence listing and a primer set for amplifying GW112 consisting of nucleotide sequences of SEQ ID NOS: 24 and 25 of the sequence listing,
(Combination for detecting ACTB):
Combination of a probe for detecting ACTB consisting of a nucleotide sequence of SEQ ID NO: 11 of the sequence listing and a primer set for amplifying ACTB consisting of nucleotide sequences of SEQ ID NOS: 30 and 31.

4. A gene detection kit for eleven target genes, the eleven target genes consisting of:
 ten genes specific to gastric cancer cells selected from the group consisting of: trefoil factor 1 (TFF1); trefoil factor 2 (TFF2); fatty acid binding protein 1, liver (FABP1); cytokeratins 20 (CK20), mucin 2 (MUC2); carcinoembryonic antigen (CEA); tumor-associated calcium signal transducer 1 (TACSTD1); maspin (MASPIN), protease, serine, 4, (PRSS4); and olfactomedin 4 (GW112); and
 beta-actin (ACTB) which is a housekeeping gene and with which expression amounts of the other genes are compared,
 wherein the gene detection kit comprises each of the eleven combinations listed below, each comprising (i) one of eleven probes for detecting the eleven target genes and (ii) one of a plurality of primer sets for amplifying by PCR a partial region of each of the eleven target genes, and
 wherein the gene detection kit comprises a probe carrier, the probe carrier consisting of the eleven probes immobilized on a carrier:
(Combination for detecting TFF1):
Combination of a probe for detecting TFF1 consisting of a nucleotide sequence of SEQ ID NO: 1 of the sequence listing and a primer set for amplifying TFF1 consisting of nucleotide sequences of SEQ ID NOS: 12 and 13 of the sequence listing,
(Combination for detecting TFF2):
Combination of a probe for detecting TFF2 consisting of a nucleotide sequence of SEQ ID NO: 2 of the sequence listing and a primer set for amplifying TFF2 consisting of nucleotide sequences of SEQ ID NOS: 14 and 15 of the sequence listing,
(Combination for detecting FABP1):
Combination of a probe for detecting FABP1 consisting of a nucleotide sequence of SEQ ID NO: 3 of the sequence listing and a primer set for amplifying FABP1 consisting of nucleotide sequences of SEQ ID NOS: 16 and 17 of the sequence listing,
(Combination for detecting CK20):
Combination of a probe for detecting CK20 consisting of a nucleotide sequence of SEQ ID NO: 4 of the sequence listing and a primer set for amplifying CK20 consisting of nucleotide sequences of SEQ ID NOS: 18 and 19 of the sequence listing,
(Combination for detecting MUC2):
Combination of a probe for detecting MUC2 consisting of a nucleotide sequence of SEQ ID NO: 5 of the sequence listing and a primer set for amplifying MUC2 consisting of nucleotide sequences of SEQ ID NOS: 26 and 27 of the sequence listing,
(Combination for detecting CEA):
Combination of a probe for detecting CEA consisting of a nucleotide sequence of SEQ ID NO: 6 of the sequence listing and a primer set for amplifying CEA consisting of nucleotide sequences of SEQ ID NOS: 20 and 21 of the sequence listing,
(Combination for detecting TACSTD1):
Combination of a probe for detecting TACSTD1 consisting of a nucleotide sequence of SEQ ID NO: 7 of the sequence listing and a primer set for amplifying TACSTD1 consisting of nucleotide sequences of SEQ ID NOS: 22 and 23 of the sequence listing,
(Combination for detecting MASPIN):
Combination of a probe for detecting MASPIN consisting of a nucleotide sequence of SEQ ID NO: 8 of the sequence listing and a primer set for amplifying MASPIN consisting of nucleotide sequences of SEQ ID NOS: 32 and 33 of the sequence listing,
(Combination for detecting PRSS4):
Combination of a probe for detecting PRSS4 consisting of a nucleotide sequence of SEQ ID NO: 9 of the sequence listing and a primer set for amplifying PRSS4 consisting of nucleotide sequences of SEQ ID NOS: 28 and 29 of the sequence listing,
(Combination for detecting GW112):
Combination of a probe for detecting GW112 consisting of a nucleotide sequence of SEQ ID NO: 10 of the sequence listing and a primer set for amplifying GW112 consisting of nucleotide sequences of SEQ ID NOS: 24 and 25 of the sequence listing,
(Combination for detecting ACTB):
Combination of a probe for detecting ACTB consisting of a nucleotide sequence of SEQ ID NO: 11 of the sequence listing and a primer set for amplifying ACTB consisting of nucleotide sequences of SEQ ID NOS: 30 and 31.

5. A gene inspection kit for nine target genes, the nine target genes consisting of:

eight genes specific to gastric cancer cells selected from the group consisting of: trefoil factor 1 (TFF1); trefoil factor 2 (TFF2); fatty acid binding protein 1, liver (FABP1); cytokeratins 20 (CK20); mucin 2 (MUC2); carcinoembryonic antigen (CEA), tumor-associated calcium signal transducer 1 (TACSTD1); and maspin (MASPIN); and beta-actin (ACTB) which is a housekeeping gene and with which expression amounts of the other genes are compared, wherein the gene inspection kit comprises each of the nine combinations listed below, each comprising (i) one of nine probes for inspection of the nine target genes and (ii) one of a plurality of primer sets for amplifying by PCR a partial region of each of the nine target genes, and wherein the gene inspection kit comprises a probe carrier to be used for detecting oligonucleotides which were amplified by PCR by using the plurality of primer sets, the probe carrier consisting of the nine probes immobilized on a carrier:

(Combination for detecting TFF1):
Combination of a probe for detecting TFF1 consisting of a nucleotide sequence of SEQ ID NO: 1 of the sequence listing and a primer set for amplifying TFF1 consisting of nucleotide sequences of SEQ ID NOS: 12 and 13 of the sequence listing, (Combination for detecting TFF2):
Combination of a probe for detecting TFF2 consisting of a nucleotide sequence of SEQ ID NO: 2 of the sequence listing and a primer set for amplifying TFF2 consisting of nucleotide sequences of SEQ ID NOS: 14 and 15 of the sequence listing, (Combination for detecting FABP1):
Combination of a probe for detecting FABP1 consisting of a nucleotide sequence of SEQ ID NO: 3 of the sequence listing and a primer set for amplifying FABP1 consisting of nucleotide sequences of SEQ ID NOS: 16 and 17 of the sequence listing, (Combination for detecting CK20):
Combination of a probe for detecting CK20 consisting of a nucleotide sequence of SEQ ID NO: 39 of the sequence listing and a primer set for amplifying CK20 consisting of nucleotide sequences of SEQ ID NOS: 18 and 19 of the sequence listing, (Combination for detecting MUC2):
Combination of a probe for detecting MUC2 consisting of a nucleotide sequence of SEQ ID NO: 40 of the sequence listing and a primer set for amplifying MUC2 consisting of nucleotide sequences of SEQ ID NOS: 26 and 46 of the sequence listing, (Combination for detecting CEA):
Combination of a probe for detecting CEA consisting of a nucleotide sequence of SEQ ID NO: 37 of the sequence listing and a primer set for amplifying CEA consisting of nucleotide sequences of SEQ ID NOS: 44 and 45 of the sequence listing, (Combination for detecting TACSTD1):
Combination of a probe for detecting TACSTD1 consisting of a nucleotide sequence of SEQ ID NO: 7 of the sequence listing and a primer set for amplifying TACSTD1 consisting of nucleotide sequences of SEQ ID NOS: 22 and 23 of the sequence listing, (Combination for detecting MASPIN):
Combination of a probe for detecting MASPIN consisting of a nucleotide sequence of SEQ ID NO: 8, 41, 42 or 43 of the sequence listing and a primer set for amplifying MASPIN consisting of nucleotide sequences of SEQ ID NOS: 32 and 33 of the sequence listing, (Combination for detecting ACTB):
Combination of a probe for detecting ACTB consisting of a nucleotide sequence of SEQ ID NO: 11 of the sequence listing and a primer set for amplifying ACTB consisting of nucleotide sequences of SEQ ID NOS: 30 and 31.

6. A gene detection kit for nine target genes, the nine target genes consisting of:

eight genes specific to gastric cancer cells selected from the group consisting of: trefoil factor 1 (TFF1); trefoil factor 2 (TFF2); fatty acid binding protein 1, liver (FABP1); cytokeratins 20 (CK20), mucin 2 (MUC2); carcinoembryonic antigen (CEA); tumor-associated calcium signal transducer 1 (TACSTD1); and maspin (MASPIN); and beta-actin (ACTB) which is a housekeeping gene and with which expression amounts of the other genes are compared, wherein the gene detection kit comprises each of the nine combinations listed below, each comprising (i) one of nine probes for detecting the nine target genes and (ii) one of a plurality of primer sets for amplifying by PCR a partial region of each of the nine target genes, and wherein the gene detection kit comprises a probe carrier, the probe carrier consisting of the nine probes immobilized on a carrier:

(Combination for detecting TFF1):
Combination of a probe for detecting TFF1 consisting of a nucleotide sequence of SEQ ID NO: 1 of the sequence listing and a primer set for amplifying TFF1 consisting of nucleotide sequences of SEQ ID NOS: 12 and 13 of the sequence listing, (Combination for detecting TFF2):
Combination of a probe for detecting TFF2 consisting of a nucleotide sequence of SEQ ID NO: 2 of the sequence listing and a primer set for amplifying TFF2 consisting of nucleotide sequences of SEQ ID NOS: 14 and 15 of the sequence listing, (Combination for detecting FABP1):
Combination of a probe for detecting FABP1 consisting of a nucleotide sequence of SEQ ID NO: 3 of the sequence listing and a primer set for amplifying FABP1 consisting of nucleotide sequences of SEQ ID NOS: 16 and 17 of the sequence listing, (Combination for detecting CK20):
Combination of a probe for detecting CK20 consisting of a nucleotide sequence of SEQ ID NO: 39 of the sequence listing and a primer set for amplifying CK20 consisting of nucleotide sequences of SEQ ID NOS: 18 and 19 of the sequence listing, (Combination for detecting MUC2):
Combination of a probe for detecting MUC2 consisting of a nucleotide sequence of SEQ ID NO: 40 of the sequence listing and a primer set for amplifying MUC2 consisting of nucleotide sequences of SEQ ID NOS: 26 and 46 of the sequence listing, (Combination for detecting CEA):
Combination of a probe for detecting CEA consisting of a nucleotide sequence of SEQ ID NO: 37 of the sequence listing and a primer set for amplifying CEA consisting of nucleotide sequences of SEQ ID NOS: 44 and 45 of the sequence listing, (Combination for detecting TACSTD1):
Combination of a probe for detecting TACSTD1 consisting of a nucleotide sequence of SEQ ID NO: 7 of the sequence listing and a primer set for amplifying TACSTD1 consisting of nucleotide sequences of SEQ ID NOS: 22 and 23 of the sequence listing,
(Combination for detecting MASPIN):
Combination of a probe for detecting MASPIN consisting of a nucleotide sequence of SEQ ID NO: 8, 41, 42 or 43 of the sequence listing and a primer set for amplifying MASPIN consisting of nucleotide sequences of SEQ ID NOS: 32 and 33 of the sequence listing,
(Combination for detecting ACTB):
Combination of a probe for detecting ACTB consisting of a nucleotide sequence of SEQ ID NO: 11 of the sequence listing and a primer set for amplifying ACTB consisting of nucleotide sequences of SEQ ID NOS: 30 and 31.

7. The kit according to claim 1, wherein the primers consisting of the nucleotide sequences of SEQ ID NOS: 12 to 21, 26, and 27 are provided as a first mixture, and the primers consisting of the nucleotide sequences of SEQ ID NOS: 28 to 33 are provided as a second mixture.

8. The kit according to claim 2, wherein all of the primers are provided as a mixture.

9. The kit according to claim 3, wherein the primers consisting of the nucleotide sequences of SEQ ID NOS: 12 to 21, 26, and 27 are provided as a first mixture, and the primers consisting of the nucleotide sequences of SEQ ID NOS: 28 to 33 are provided as a second mixture.

10. The kit according to claim 4, wherein the primers consisting of the nucleotide sequences of SEQ ID NOS: 12 to 21, 26 and 27 are provided as a first mixture, and the primers consisting of the nucleotide sequences of SEQ ID NOS: 28 to 33 are provided as a second mixture.

11. The kit according to claim 5, wherein all of the primers are provided as a mixture.

12. The kit according to claim 6, wherein all of the primers are provided as a mixture.

* * * * *